(12) United States Patent
Seshimo et al.

(10) Patent No.: US 7,955,777 B2
(45) Date of Patent: Jun. 7, 2011

(54) COMPOUND, ACID GENERATOR, RESIST COMPOSITION AND METHOD OF FORMING RESIST PATTERN

(75) Inventors: Takehiro Seshimo, Kawasaki (JP); Yoshiyuki Utsumi, Kawasaki (JP); Yoshitaka Komuro, Kawasaki (JP); Keita Ishiduka, Kawasaki (JP); Akiya Kawaue, Kawasaki (JP); Kyoko Ohshita, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 129 days.

(21) Appl. No.: 12/327,549

(22) Filed: Dec. 3, 2008

(65) Prior Publication Data
US 2009/0162787 A1 Jun. 25, 2009

(30) Foreign Application Priority Data
Dec. 5, 2007 (JP) ................. 2007-315239

(51) Int. Cl.
*G03F 7/00* (2006.01)
*G03F 7/004* (2006.01)

(52) U.S. Cl. ................ 430/270.1; 430/311; 430/905; 562/41; 562/44

(58) Field of Classification Search ............ 430/270.1, 430/913, 905, 311; 562/41, 44
See application file for complete search history.

(56) References Cited

U.S. PATENT DOCUMENTS

| | | | |
|---|---|---|---|
| 5,945,517 A | 8/1999 | Nitta et al. | |
| 6,153,733 A | 11/2000 | Yukawa et al. | |
| 6,180,313 B1 | 1/2001 | Yukawa et al. | |
| 7,122,294 B2 * | 10/2006 | Lamanna | 430/280.1 |
| 7,301,047 B2 | 11/2007 | Yoshida et al. | |
| 7,323,287 B2 | 1/2008 | Iwai et al. | |
| 7,745,097 B2 * | 6/2010 | Hada et al. | 430/270.1 |
| 2007/0100158 A1 | 5/2007 | Harada et al. | |
| 2007/0100159 A1 | 5/2007 | Yoshida et al. | |
| 2007/0122750 A1 | 5/2007 | Yamaguchi et al. | |

FOREIGN PATENT DOCUMENTS

| | | | |
|---|---|---|---|
| JP | H09-208554 | | 8/1997 |
| JP | H11-035551 | | 2/1999 |
| JP | H11-035552 | | 2/1999 |
| JP | H11-035573 | | 2/1999 |
| JP | H11-322707 | | 11/1999 |
| JP | 2003-241385 | | 8/2003 |
| JP | 2006162735 A | * | 6/2006 |
| KR | 10-2007-0045969 | | 5/2007 |
| WO | WO 2004-074242 | | 9/2004 |

OTHER PUBLICATIONS

Machine translation of JP 2006-162735 (no date).*
Office Action issued in counterpart Korean Patent Application No. 10-2008-0068190, dated Dec. 9, 2009.

* cited by examiner

*Primary Examiner* — Amanda C. Walke
(74) *Attorney, Agent, or Firm* — Knobbe, Martens, Olson & Bear, LLP

(57) ABSTRACT

There are provided a compound represented by a general formula (b1-1) shown below suitable as an acid generator for a resist composition, a compound represented by a general formula (I) shown below suitable as a precursor for the compound represented by the general formula (b1-1), an acid generator, a resist composition, and a method of forming a resist pattern.

[Chemical Formula 1]

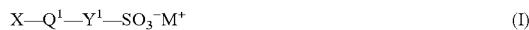

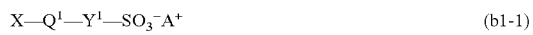

(wherein, $Y^1$ represents a bivalent linking group or a single bond; $Y^1$ represents an alkylene group which may contain a substituent group or a fluorinated alkylene group which may contain a substituent group; X represents an aromatic cyclic group of 5 to 30 carbon atoms which contains a fluorine atom and may contain a substituent group; $M^+$ represents an alkali metal ion; and $A^+$ represents an organic cation.).

14 Claims, No Drawings

COMPOUND, ACID GENERATOR, RESIST COMPOSITION AND METHOD OF FORMING RESIST PATTERN

TECHNICAL FIELD

The present invention relates to a novel compound suitable as an acid generator for a resist composition, a compound suitable as a precursor of the novel compound, an acid generator, a resist composition containing the acid generator, and a method of forming a resist pattern using the resist composition. This application claims priority from Japanese Patent Application No. 2007-315239 filed on Dec. 5, 2007, the disclosure of which is incorporated by reference herein.

BACKGROUND ART

Lithography techniques include processes in which, for example, a resist film formed from a resist material is formed on top of a substrate, the resist film is selectively exposed with irradiation such as light, an electron beam or the like through a mask in which a predetermined pattern has been formed, and then a developing treatment is conducted, thereby forming a resist pattern of the prescribed shape in the resist film. Resist materials in which the exposed portions change to become soluble in a developing solution are termed positive materials, whereas resist materials in which the exposed portions change to become insoluble in the developing solution are termed negative materials.

In recent years, in the production of semiconductor elements and liquid crystal display elements, advances in lithography techniques have led to rapid progress in the field of miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are starting to be introduced in mass production of semiconductor elements. Furthermore, research is also being conducted into lithography techniques that use $F_2$ excimer lasers, electron beams (EB), extreme ultraviolet radiation (EUV) and X-rays.

Resist materials are required to have lithography properties such as high sensitivity to the aforementioned light source and enough resolution to reproduce patterns with very fine dimensions. As resist materials which fulfill the aforementioned requirements, there is used a chemically-amplified resist containing a base resin that displays changed alkali solubility under action of acid, and an acid generator that generates acid upon exposure. For example, a chemically-amplified positive resist includes a resin in which the alkali solubility increases under action of an acid as a base resin and an acid generator, and when an acid is generated from the acid generator upon exposure in the formation of a resist pattern, the exposed portions are converted to a soluble state in an alkali developing solution.

Until recently, polyhydroxystyrene (PHS) or derivative resins (PHS-based resins) in which the hydroxyl groups have been protected with acid dissociable, dissolution inhibiting groups, which exhibit a high degree of transparency relative to KrF excimer laser (248 nm), have been used as the base resin of chemically-amplified resists. However, because PHS-based resins contain aromatic rings such as benzene rings, their transparency is inadequate for light with a wavelength shorter than 248 nm, such as light of 193 nm. Accordingly, chemically-amplified resists that use a PHS-based resin as the base resin have a disadvantage in that they have low resolution in processes that use, for example, light of 193 nm. As a result, resins (acrylic resins) that contain structural units derived from (meth)acrylate esters within the main chain are now widely used as base resins for resists that use ArF excimer laser lithography, as they exhibit excellent transparency in the vicinity of 193 nm. In the case of a positive resist, as the base resin, those which have a structural unit derived from (meth)acrylate ester including an aliphatic polycyclic group-containing, tertiary alkyl ester-type acid dissociable, dissolution inhibiting group, such as a structural unit derived from 2-alkyl-2-adamantyl(meth)acrylate, are mainly used (for example, see Patent Document 1).

Here, the term "(meth)acrylate ester" is a generic term that includes either or both of the acrylate ester having a hydrogen atom bonded with the α-position and the methacrylate ester having a methyl group bonded with the α-position. The term "(meth)acrylate" is a generic term that includes either or both of the acrylate having a hydrogen atom bonded with the α-position and the methacrylate having a methyl group bonded with the α-position. The term "(meth)acrylic acid" is a generic term that includes either or both of the acrylic acid having a hydrogen atom bonded with the α-position and the methacrylic acid having a methyl group bonded with the α-position.

As an acid generator used in a chemically-amplified resist, a large variety of acid generators are proposed, and examples thereof include onium salt-based acid generators such as iodonium salts and sulfonium salts.

[Patent Document 1] Japanese Unexamined Patent Application, First Publication No. 2003-241385.

DISCLOSURE OF THE INVENTION

Problems to be Solved by the Invention

As an anion moiety of the onium salt-based acid generators described above, a perfluoroalkylsulfonate ion has generally been used. It is considered that a perfluoroalkyl chain included in such an anion moiety preferably be a long chain in order to suppress the diffusion of an acid after exposure. However, a perfluoroalkyl chain of 6 to 10 carbon atoms is persistent (hardly-degradable), therefore a nonafluorobutane sulfonate ion or the like has been used instead, because it can be handled more safely in terms of bioaccumulation potential. For these reasons, a novel compound more suitable as an acid generator for a resist composition is required.

The present invention takes the above circumstances into consideration, with an object of providing a novel compound suitable as an acid generator for a resist composition, a compound suitable as a precursor of the novel compound, an acid generator, a resist composition, and a method of forming a resist pattern.

Means for Solving the Problems

To achieve the above object, the present invention employs the following constitutions.

A first aspect of the present invention is a compound (hereinafter referred to as compound (I)) represented by a general formula (I) shown below.

[Chemical Formula 1]

$$X-Q^1-Y^1-SO_3^-M^+ \quad (I)$$

(wherein, $Q^1$ represents a bivalent linking group or a single bond; $Y^1$ represents an alkylene group which may contain a substituent group, or a fluorinated alkylene group which may contain a substituent group; X represents an aromatic cyclic group of 5 to 30 carbon atoms which contains a fluorine atom and may contain a substituent group; and M⁺ represents an alkali metal ion.)

A second aspect of the present invention is a compound (hereinafter, referred to as compound (B1)) represented by a general formula (b1-1) shown below.

[Chemical Formula 2]

X—Q¹—Y¹—SO₃⁻A⁺    (b1-1)

(wherein, Q¹ represents a bivalent linking group or a single bond; Y¹ represents an alkylene group which may contain a substituent group, or a fluorinated alkylene group which may contain a substituent group; X represents an aromatic cyclic group of 5 to 30 carbon atoms which contains a fluorine atom and may contain a substituent group; and A⁺ represents an organic cation.)

A third aspect of the present invention is an acid generator composed of the compound (B1) according to the second aspect.

A fourth aspect of the present invention is a resist composition including a base component (A) which displays changed solubility in an alkali developing solution under action of acid, and an acid generator component (B) which generates an acid upon exposure, wherein the acid generator component (B) includes an acid generator (B1) composed of a compound represented by a general formula (b1-1) shown below.

[Chemical Formula 3]

X—Q¹—Y¹—SO₃⁻A⁺    (b1-1)

(wherein, Q¹ represents a bivalent linking group or a single bond; Y¹ represents an alkylene group which may contain a substituent group, or a fluorinated alkylene group which may contain a substituent group; X represents an aromatic cyclic group of 5 to 30 carbon atoms which contains a fluorine atom and may contain a substituent group; and A⁺ represents an organic cation.)

A fifth aspect of the present invention is a method of forming a resist pattern, which includes forming a resist film on a substrate using a resist composition according to the fourth aspect of the present invention; exposing the resist film; and developing the resist film with an alkali to form a resist pattern.

In the present specification and claims, the term "alkyl group" is a concept containing a linear, branched, and cyclic monovalent saturated hydrocarbon group, unless another specific definition is provided.

Also, the term "alkylene group" is a concept containing a linear, branched, and cyclic bivalent saturated hydrocarbon group, unless another specific definition is provided.

The term "lower alkyl group" means an alkyl group of 1 to 5 carbon atoms.

The term "halogenated alkyl group" means a group in which a part or all of hydrogen atoms in an alkyl group are substituted with a halogen atoms, and examples of the halogen atom include a fluorine atom, a chlorine atom, a bromine atom, and an iodine atom.

The term "aliphatic" is a relative concept used in relation to the term "aromatic", and is defined as a group or compound that contains no aromaticity.

The term "structural unit" means a monomer unit that contributes to the formation of a resin component (polymer).

The term "exposure" is used as a general concept involving irradiation with any form of radiation.

Effects of the Invention

According to the present invention, there can be provided a novel compound suitable as an acid generator for a resist composition, a compound suitable as a precursor of the novel compound, an acid generator, a resist composition, and a method of forming a resist pattern.

Best Mode for Carrying out the Invention

<<Compound (I)>>

The compound (I) according to the first aspect of the present invention is represented by the general formula (I).

In the formula (I), Q¹ represents a bivalent linking group or a single bond; Y¹ represents an alkylene group which may contain a substituent group, or a fluorinated alkylene group which may contain a substituent group; X represents an aromatic cyclic group of 5 to 30 carbon atoms which contains a fluorine atom and may contain a substituent group; and M⁺ represents an alkali metal ion.

In the formula (I), Q¹ represents a bivalent linking group or single bond.

Example of the bivalent linking group for Q¹ include an alkylene group, and a group which contains a hetero atom (hereinafter, referred to as hetero atom-containing linking group).

The term "hetero atom" in the hetero atom-containing linking group means an atom other than a carbon atom and hydrogen atom, and examples thereof include an oxygen atom, a sulfur atom, and a nitrogen atom.

The alkylene group for Q¹ may be linear or branched. The number of carbon atoms in the alkylene group is preferably 1 to 12, more preferably 1 to 5, and still more preferably 1 to 3.

Specific examples of the alkylene group include a methylene group [—CH₂—]; an alkylmethylene group such as —CH(CH₃)—, —CH(CH₂CH₃)—, —C(CH₃)₂—, —C(CH₃)(CH₂CH₃)—, —C(CH₃)(CH₂CH₂CH₃)—, and —C(CH₂CH₃)₂—; an ethylene group [—CH₂CH₂—]; an alkylethelene group such as —CH(CH₃)CH₂—, —CH(CH₃)CH(CH₃)—, —C(CH₃)₂CH₂—, —CH(CH₂CH₃)CH₂—, and —CH(CH₂CH₂CH₃)CH₂—; a trimethylene group (n-propylene group) [—CH₂CH₂CH₂—]; an alkyltrimethylene group such as —CH(CH₃)CH₂CH₂—, and —CH₂CH(CH₃)CH₂—; tetramethylene group [—CH₂CH₂CH₂CH₂—]; an alkyltetramethylene group such as —CH(CH₃)CH₂CH₂CH₂—, and —CH₂CH(CH₃)CH₂CH₂—; and a pentamethylene group [—CH₂CH₂CH₂CH₂CH₂—].

Examples of the hetero atom-containing linking group include nonhydrocarbon-based hetero atom-containing linking groups such as an oxygen atom (ether linkage; —O—), a sulfur atom (thioether linkage; —S—), a —NH— linkage (wherein, H may be substituted with a substituent group such as an alkyl group, an acyl group, or the like), an ester linkage (—C(═O)—O—), an amide linkage (—C(═O)—NH—), a carbonyl group (—C(═O)—), or a carbonate linkage (—O—C(═O)—O—); and a combination of the nonhydrocarbon-based hetero atom-containing linking groups with the aforementioned alkylene groups. Examples of the above combination include a group of —R⁹¹—O—, and a group of —R⁹²—O—C(═O)— (wherein, R⁹¹ and R⁹² each independently represents an alkylene group). In the above groups of —R⁹¹—O— and —R⁹²—O—C(═O)—, as the alkylene group for R⁹¹ and R⁹², the same alkylene groups as those described in the bivalent linking group for Q¹ described above can be mentioned.

Of these, the aforementioned Q¹ is preferably a bivalent linking group which contains an ester linkage and/or ether linkage. Of these, the aforementioned Q¹ is more preferably an ester linkage, an ether linkage, a group of —R⁹¹—O—, a group of R⁹¹—O—C(═O)— (wherein, R⁹¹ and R⁹² each independently preferably an alkylene group of 1 to 3 carbon atoms) or a combination thereof, still more preferably a combination thereof, and most preferably a combination of an ester linkage with a group of —$R^{91}$—O—, and a combination of an ether linkage with a group of —$R^{92}$—O—C(=O)—.

In the formula (I), $Y^1$ represents an alkylene group which may contain a substituent group, or a fluorinated alkylene group which may contain a substituent group.

$Y^1$ is preferably linear or branched, and the number of carbon atoms in $Y^1$ is preferably 1 to 6, more preferably 1 to 5, and still more preferably 1 to 4.

Suitable examples of $Y^1$ include —$CF_2$—, —$CF_2CF_2$—, —$CF_2CF_2CF_2$—, $CF(CF_3)CF_2$—, —$CF(CF_2CF_3)$—, —$C(CF_3)_2$—, —$CF_2CF_2CF_2CF_2$—, $CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—; —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

Of these, Y1 is more preferably a fluorinated alkylene group, and still more preferably a fluorinated alkylene group in which a carbon atom bonded with the adjacent sulfur atom is fluorinated. Examples of such fluorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—; —$CH_2CF_2$—, —$CH_2CH_2CF_2$—, —$CH_2CF_2CF_2$—; $CH_2CH_2CH_2CF_2$—, —$CH_2CH_2CF_2CF_2$—, and —$CH_2CF_2CF_2CF_2$—.

Of these, —$CF_2$—, —$CF_2CF_2$—, —$CF_2CF_2CF_2$—, or —$CH_2CF_2CF_2$— is preferable, —$CF_2$—, —$CF_2CF_2$—, or —$CF_2CF_2CF_2$— is more preferable, and —$CF_2$— is still more preferable.

The alkylene group or fluorinated alkylene group for $Y^1$ may each contain a substituent group. Examples of the substituent group include an alkyl group, an alkoxy group, a halogen atom, a halogenated alkyl group, a hydroxyl group, and an oxygen atom (=O).

The alkyl group for the substituent group is preferably a lower alkyl group of 1 to 5 carbon atoms, and more preferably a methyl group, an ethyl group, a propyl group, an n-butyl group, or a tert-butyl group.

The alkoxy group for the substituent group is preferably an alkoxy group of 1 to 5 carbon atoms, and more preferably a methoxy group, an ethoxy group, an n-propoxy group, an iso-propoxy group, an n-butoxy group, or a tert-butoxy group, and still more preferably a methoxy group or an ethoxy group.

Examples of the halogen atom for the substituent group include a fluorine atom, a chlorine atom, a bromine atom, and an iodine atom. Of these, a fluorine atom is preferable.

Examples of the halogenated alkyl group for the substituent group include groups in which a part or all of the hydrogen atoms in the above alkyl group are substituted with the above halogen atoms.

In the formula (I), $M^+$ represents an alkyl metal ion.

Examples of alkali metal ions for $M^+$ include a sodium ion, a lithium ion, and a potassium ion. Of these, a sodium ion or a lithium ion is preferable.

In the formula (I), X means an aromatic cyclic group of 5 to 30 carbon atoms which contains a fluorine atom and may contain a substituent group.

The cyclic group in X may contain a substituent group. Examples of the substituent group include an alkyl group, an alkoxy group, a halogen atom, a halogenated alkyl group, a hydroxyl group, and an oxygen atom (=O). Specific examples of the substituent group include those described as the substituent groups which the alkylene group or the fluorinated alkylene group for $Y^1$ may contain.

Also, as the substituent group, a —COOR", a —OC(=O)R", a hydroxyalkyl group, and a cyano group can be mentioned. The aforementioned R" each represents a hydrogen atom, or a linear, branched or cyclic alkyl group of 1 to 15 carbon atoms.

In the case that R" is a linear or branched alkyl group, R" preferably has 1 to 10 carbon atoms, more preferably 1 to 5 carbon atoms, and still more preferably a methyl group or an ethyl group.

In the case that R" is a cyclic alkyl group, the number of carbon atoms is preferably 3 to 15, more preferably 4 to 12, and most preferably 5 to 10. Specific examples of the cyclic alkyl group for R" include groups in which one or more hydrogen atoms have been removed from a monocycloalkane or a polycycloalkane such as a bicycloalkane, tricycloalkane or tetracycloalkane, in which a fluorine atom or a fluorinated alkyl group may or may not be included as a substituent group. Specific examples include groups in which at least one hydrogen atom has been removed from a monocycloalkane such as cyclopentane or cyclohexane; and groups in which at least one hydrogen atom has been removed from a polycycloalkane such as adamantane, norbornane, isobornane, tricyclodecane or tetracyclododecane.

As the hydroxyalkyl group for the aforementioned substituent group, groups in which at least one hydrogen atom of the alkyl group described as the substituent group in $Y^1$ is substituted with a hydroxyl group can be mentioned.

The aromatic cyclic group of 5 to 30 carbon atoms which contain a fluorine atom for X is a group in which a part or all of hydrogen atoms in the aromatic cyclic group are substituted with fluorine atoms, and is preferably a group in which all of hydrogen atoms in the aromatic cyclic group are substituted with fluorine atoms. When all hydrogen atoms in the aromatic cyclic group are substituted with fluorine atoms, lithography properties can be improved in the case that an acid generator for which the compound (I) is used as the precursor are used in a resist composition. Also, the solubility in a resist solvent can be improved.

The number of carbon atoms in the aromatic cyclic group for X is 5 to 30, preferably 5 to 20, more preferably 6 to 15, and still more preferably 6 to 12. Here, the number of the carbon atoms described above does not include the number of carbon atoms in the substituent group.

As the aromatic cyclic group for X, a group containing an aromatic hydrocarbon ring in which the ring skelton of the aromatic ring consists of carbon atoms, a group containing an aromatic heterocyclic ring in which the ring skelton of the aromatic ring contains hetero atoms other than carbon atoms can be mentioned.

Specific examples thereof include an aryl group in which one hydrogen atom has been removed from an aromatic hydrocarbon ring, such as a phenyl group, a biphenyl group, a fluorenyl group, a naphthyl group, an anthryl group, and a phenanthryl group; and heteroaryl groups in which a part of the carbon atoms which constitutes the ring(s) of the aforementioned aryl groups are substituted with heteroatoms such as an oxygen atom, a sulfur atom, and a nitrogen atom. Of these, an aryl group in which one hydrogen atom has been removed from an aromatic hydrocarbon ring is preferable, and a phenyl group or a naphthyl group is more preferable.

Of these, X in the general formula (I) is most preferably a phenyl group in which all of hydrogen atoms in the aromatic cyclic group are substituted with fluorine atoms, because lithography properties can be more improved in the case that an acid generator produced from the compound (I) as a precursor is used in a resist composition.

In the present invention, the compound (I) is preferably a compound represented by a general formula (I-11) shown below.

[Chemical Formula 4]

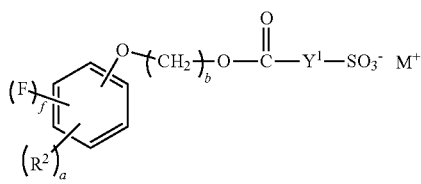
(I-11)

(In the formula, $Y^1$ and $M^+$ are as defined above; $R^2$ represents an alkyl group, an alkoxy group, a halogen atom (excluding a fluorine atom), a halogenated alkyl group, a hydroxyl group, an oxygen atom (=O), —COOR", —OC(=O)R", a hydroxyalkyl group, or a cyano group; a represents an integer of 0 to 2; b represents an integer of 0 to 5; f represents an integer of 1 to 5; and $1 \leq (a+f) \leq 5$.)

$Y^1$ is preferably a group of —[C($C^5$)($C^6$)]$_c$— (wherein, $R^5$ and $R^6$ each independently represents a fluorine atom or a fluorinated alkyl group. c represents an integer of 1 to 3). In $Y^1$, c is most preferably 1. The fluorinated alkyl group for $R^5$ and $R^6$ is preferably a linear or branched alkyl group. Also, the fluorinated alkyl group is preferably a perfluoroalkyl group. The number of carbon atoms in the fluorinated alkyl group is preferably 1 to 5, and most preferably 1. Both of $R^5$ and $R^6$ are most preferably fluorine atoms.

Examples of $R^2$ include the same atoms and groups as those described in the explanation of the substituent group which the cyclic group for the aforementioned X may contain.

a is most preferably 0.

b is preferably 1 to 4, more preferably 1 or 2, and most preferably 2.

f is preferably 2 to 5, and most preferably 5.

The compound (I) is a novel compound.

The compound (I) is useful as a precursor in a method of manufacturing a compound (B1) described below.

<Method of Manufacturing Compound (I)>

There is no particular restrictions on the method of manufacturing the compound (I) according to the first aspect of the present invention, and for example, in case of manufacturing the compound represented by the above general formula (I-11), a method is preferably used which includes a step of dehydrating/condensating a compound (I-3) represented by a general formula (I-3) shown below and a compound (I-4) represented by a general formula (I-4) shown below in the presence of an acidic catalyst to obtain the compound (I).

[Chemical Formula 5]

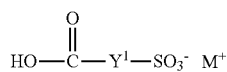
(I-3)

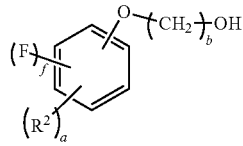
(I-4)

In the above formula (I-3), $Y^1$ and $M^+$ are the same as $Y^1$ and $M^+$ described above in the formula (I).

In the above formula (I-4), $R^2$, a, b, and f are respectively the same as $R^2$, a, b, and f described above in the formula (I-11).

Each of the compounds (I-3) and (I-4) may be a commercially available compound, or may be a compound obtained by a synthesis.

There is no particular restrictions on the method of manufacturing the compound (I-3), and for example, the compound (I-3) can be synthesized by steps of: treating a compound (I-1) represented by a general formula (I-1) shown below with alkali to obtain a compound (I-2) represented by a general formula (I-2) shown below (hereinafter referred to as step (i)); and heating the compound (I-2) in the presence of an acid to obtain the compound (I-3) (hereinafter referred to as step (ii)).

[Chemical Formula 6]

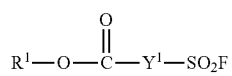
(I-1)

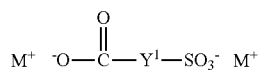
(I-2)

(In the formula, $R^1$ represents an alkyl group of 1 to 5 carbon atoms; and $Y^1$ and $M^+$ are as defined above.)

In the step (i), a commercially available compound can be used as the compound (I-1).

In the step (i), the alkali treatment can be performed, for example, by heating the compound (I-1) in the presence of an alkal, and as a specific example thereof, the alkali treatment can be performed by dissolving the compound (I-1) in a solvent such as water and tetrahydrofuran, adding an alkali into the solution, and then heating the solution.

As the alkali, sodium hydroxide, potassium hydroxide, and lithium hydroxide can be mentioned.

The amount of the alkali used is preferably 1 to 5 mol, and more preferably 2 to 4 mol, relative to 1 mol of the compound (I-1).

The heating temperature is preferably approximately 20 to 120° C., and more preferably approximately 50 to 100° C. The heating time is preferably usually 0.5 to 12 hours, and more preferably 1 to 5 hours, although it differs depending on conditions such as the heating temperature.

After the aforementioned alkali treatment, the neutralization may further be performed. The neutralization can be performed by adding an acid such as a hydrochloric acid, a sulfuric acid, or a p-toluenesulfonic acid in the reaction solution obtained after the aforementioned alkali treatment. Here, it is preferable that the neutralization be performed so that the reaction solution after addition of the acid has a pH of 6 to 8.

After the reaction, the compound (I-2) in the reaction solution may be isolated and purified. Conventional methods can be used for the isolation and purification, and for example, concentration, solvent extraction, distillation, crystallization, recrystallization, chromatography, or the like can be used alone, or two or more types can be used in combination.

The step (ii) can be performed by dissolving the compound (I-2) in a solvent such as acetonitrile, methyl ethyl ketone, or the like, and heating the solution after addition of an acid.

In the step (ii), an acid which exhibits stronger acidity than the compound (I-3) is used as the acid. Examples of the acid include p-toluenesulfonic acid, sulfuric acid, hydrochloric acid, and the like.

The amount of the acid used is preferably 0.5 to 3 mol. and more preferably 1 to 2 mol. relative to 1 mol of the compound (I-2).

The heating temperature is preferably approximately 20 to 150° C., and more preferably approximately 50 to 120° C. The heating time is usually preferably 0.5 to 12 hours, and more preferably 1 to 5 hours, although it differs depending on conditions such as the heating temperature.

After the reaction, the compound (I-3) in the reaction solution may be isolated and purified. Conventional methods can be used for the isolation and purification, and for example, concentration, solvent extraction, distillation, crystallization, recrystallization, chromatography, or the like can be used alone, or two or more types can be used in combination.

The dehydration/condensation reaction can be performed, for example, by dissolving the compounds (I-3) and (I-4) in an aprotic organic solvent such as dichloroethane, benzene, toluene, ethylbenzene, chlorobenzene, acetonitrile, and N,N-dimethylformamide, and then stirring the solution obtained in the presence of an acidic catalyst.

In the dehydration/condensation reaction described above, it is preferable to use an aromatic-based organic solvent such as toluene, xylene, or chlorobenzene as the organic solvent, because it improves the yield, purity, and the like of the compound (I) obtained.

The reaction temperature of dehydration/condensation reaction is preferably 20° C. to 200° C., and more preferably 50° C. to 150° C. The reaction time is usually preferably 1 to 30 hours, and more preferably 3 to 30 hours, although it differs depending on conditions such as the reactivity of the compounds (I-3) and (I-4), the reaction temperature, or the like.

There is no particular restrictions on the amount of the compound (I-3) used in the dehydration/condensation reaction. Usually, the amount is preferably approximately 0.2 mol to 3 mol. more preferably approximately 0.5 to 2 mol. and most preferably approximately 0.75 to 1.5 mol. relative to 1 mol of the compound (I-4).

Examples of the acidic catalyst include an organic acid such as p-toluenesulfonic acid; and an inorganic acid such as sulfuric acid, hydrochloric acid, or the like. One type of these acidic catalysts may be used alone, or two or more types may be used in combination.

The amount of the acidic catalyst used in the dehydration/condensation reaction may be a catalyst amount, and usually approximately within a range of 0.001 to 5 mol. relative to 1 mol of the compound (I-4).

The dehydration/condensation reaction may be performed while removing water thus generated in the reaction by using a dean-stark apparatus or the like. This enables the reaction time to be shortened.

Also, in the dehydration/condensation reaction, a dehydration agent such as 1,1'-carbonyldiimidazole or N,N'-dicyclohexylcarbodiimide may be concomitantly used.

In the case of using the dehydration agent, the amount of the dehydration agent used is usually preferably within a range of 0.2 to 5 mol. and more preferably within a range of 0.5 to 3 mol. relative to 1 mol of the compound (I-4).

The structure of the compound obtained by the above method can be confirmed by a general organic analysis method such as a $^1$H-nuclear magnetic resonance (NMR) spectrum method, a $^{19}$F-NMR spectrum method, an infrared resonance (IR) spectrum method, a mass spectrometry (MS) method, an element analysis method, and an X-ray crystallographic analysis method.

<<Compound (B1)>>

The compound (B1) according to the second aspect of the present invention is represented by the general formula (b1-1).

In the formula (b1-1), $Q^1$, $Y^1$, and X are the same, respectively, as $Q^1$, $Y^1$, and X described in the general formula (I).

In the compound (B1), $Q^1$ is preferably a bivalent linking group containing an ester linkage or ether linkage.

There is no particular restriction on the organic cation for $A^+$, and those which have conventionally been known as cation moieties in onium salt-based acid generators can be used by being arbitrarily selected. Specifically, a cation moiety represented by general formulae (b'-1), (b'-2), (b-5), or (b-6) can be suitably used.

[Chemical Formula 7]

(b'-1)

(b'-2)

(In the formula, $R^{1''}$ to $R^{3''}$, $R^{5''}$, and $R^{6''}$ each independently represents an aryl group or an alkyl group; two of $R^{1''}$ to $R^{3''}$ may mutually be bonded to form a ring together with the sulfur atom in the formula; and at least one of $R^{1''}$ to $R^{3''}$ represents an aryl group, and at least one of $R^{5''}$ and $R^{6''}$ represents an aryl group.)

[Chemical Formula 8]

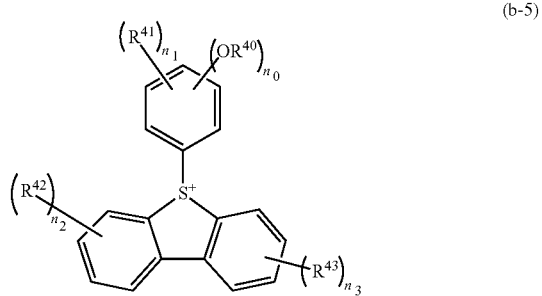

(b-5)

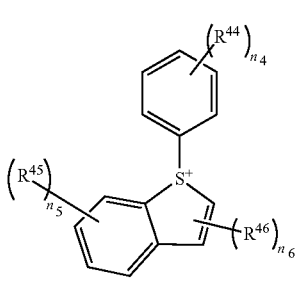

(b-6)

(In the formula, $R^{40}$ represents a hydrogen atom or an alkyl group; $R^{41}$ represents an alkyl group, an acetyl group, a carboxy group, or a hydroxyalkyl group; $R^{42}$ to $R^{46}$ each independently represents an alkyl group, an acetyl group, an alkoxy group, a carboxy group, or a hydroxyalkyl group; $n_0$ to $n_5$ each independently represents an integer of 0 to 3, with the proviso that $n_0+n_1$ is 5 or less; and $n_6$ represents an integer of 0 to 2.)

In the formula (b'-1), $R^{1\prime\prime}$ to $R^{3\prime\prime}$ each independently represents an aryl group or an alkyl group. Two of $R^{1\prime\prime}$ to $R^{3\prime\prime}$ may be mutually bonded to form a ring together with the sulfur atom in the formula.

Also, at least one of $R^{1\prime\prime}$ to $R^{3\prime\prime}$ represents an aryl group. Two or more of $R^{1\prime\prime}$ to $R^{3\prime\prime}$ are preferably aryl groups, and all of $R^{1\prime\prime}$ to $R^{3\prime\prime}$ are most preferably aryl groups.

There is no particular restrictions on the aryl group for $R^{1\prime\prime}$ to $R^{3\prime\prime}$, and examples thereof include a non-substituted aryl group of 6 to 20 carbon atoms; a substituted aryl group in which a part or all of hydrogen atoms in the above non-substituted aryl group are substituted with an alkyl group, an alkoxy group, an alkoxyalkyloxy group, an alkoxycarbonylalkyloxy group, a halogen atom, a hydroxyl group, or the like; and a group of —$(R^{4\prime})$—C(=O)—$R^{5\prime}$. Here, $R^{4\prime}$ represents an alkylene group of 1 to 5 carbon atoms. $R^{5\prime}$ represents an aryl group. As the aryl group for $R^{5\prime}$, the same aryl groups as those described above in $R^{1\prime\prime}$ to $R^{3\prime\prime}$ can be mentioned.

The non-substituted aryl group is preferably an aryl group of 6 to 10 carbon atoms, because it can be synthesized inexpensively. Specific examples thereof include a phenyl group and a naphthyl group.

The alkyl group for the substituent group in the substituted aryl group for $R^{1\prime\prime}$ to $R^{3\prime\prime}$ is preferably an alkyl group of 1 to 5 carbon atoms, and most preferably a methyl group, an ethyl group, a propyl group, an n-butyl group, and a tert-butyl group.

The alkoxy group for the substituent group in the substituted aryl group for $R^{1\prime\prime}$ to $R^{3\prime\prime}$ is preferably an alkoxy group of 1 to 5 carbon atoms, and most preferably a methoxy group, an ethoxy group, an n-propoxy group, an iso-propoxy group, an n-butoxy group, and a tert-butoxy group.

The halogen atom for the substituent group in the substituted aryl group for $R^{1\prime\prime}$ to $R^{3\prime\prime}$ is preferably a fluorine atom.

Examples of the alkoxyalkyloxy group for the substituent group in the substituted aryl group for $R^{1\prime\prime}$ to $R^{3\prime\prime}$ include groups represented by a general formula: —O—C($R^{47}$)($R^{48}$)—O—$R^{49}$ (wherein, $R^{47}$ and $R^{48}$ each independently represents a hydrogen atom, or a linear or branched alkyl group; and $R^{49}$ represents an alkyl group).

The alkyl group for $R^{47}$ and $R^{48}$ preferably has 1 to 5 carbon atoms, and may be either linear or branched. As the alkyl group, an ethyl group or a methyl group is preferable, and a methyl group is most preferable.

At least one of $R^{47}$ and $R^{48}$ is preferably a hydrogen atom. Particularly, it is preferable that one of $R^{47}$ and $R^{48}$ be a hydrogen atom, and the other be a hydrogen atom or a methyl group.

The alkyl group for $R^{49}$ preferably has 1 to 15 carbon atoms, and may be linear, branched, or cyclic.

The linear or branched alkyl group for $R^{49}$ preferably has 1 to 5 carbon atoms, and examples thereof include a methyl group, an ethyl group, a propyl group, an n-butyl group, and a tert-butyl group.

The cyclic alkyl group for $R^{49}$ preferably has 4 to 15 carbon atoms, more preferably has 4 to 12 carbon atoms, and most preferably 5 to 10 carbon atoms. Specific examples of the cyclic alkyl group for $R^{49}$ include groups in which one or more hydrogen atoms have been removed from a monocycloalkane or a polycycloalkane such as a bicycloalkane, tricycloalkane or tetracycloalkane, in which an alkyl group of 1 to 5 carbon atoms, a fluorine atom, or a fluorinated alkyl group of 1 to 5 carbon atoms may or may not be included as a substituent group. Specific examples of monocycloalkanes include cyclopentane and cyclohexane. Specific examples of polycycloalkanes include adamantane, norbornane, isobornane, tricyclodecane, and tetracyclododecane. Of these, a group in which one or more hydrogen atoms have been removed from adamantane is preferable.

Examples of the alkoxycarbonylalkyloxy group for the substituent group in the substituted aryl group for $R^{1\prime\prime}$ to $R^{3\prime\prime}$ include groups represented by a general formula: —O—$R^{50}$—C(=O)—O—$R^{51}$ (wherein, $R^{50}$ represents a linear or branched alkylene group, and $R^{51}$ represents a tertiary alkyl group).

The linear or branched alkylene group for $R^{50}$ preferably has 1 to 5 carbon atoms, and examples thereof include a methylene group, an ethylene group, a trimethylene group, a tetramethylene group, and a 1,1-dimethylethylene group.

Examples of the tertiary alkyl group for $R^{51}$ include a 2-methyl-2-adamantyl group, 2-ethyl-2-adamantyl group, 1-methyl-1-cyclopentyl group, 1-ethyl-1-cyclopentyl group, 1-methyl-1-cyclohexyl group, 1-ethyl-1-cyclohexyl group, 1-(1-adamantyl)-1-methylethyl group, 1-(1-adamantyl)-1-methylpropyl group, 1-(1-adamantyl)-1-methylbutyl group, 1-(1-adamantyl)-1-methylpentyl group, 1-(1-cyclopentyl)-1-methylethyl group, 1-(1-cyclopentyl)-1-methylpropyl group, 1-(1-cyclopentyl)-1-methylbutyl group, 1-(1-cyclopentyl)-1-methylpentyl group, 1-(1-cyclohexyl)-1-methylethyl group, 1-(1-cyclohexyl)-1-methylpropyl group, 1-(1-cyclohexyl)-1-methylbutyl group, 1-(1-cyclohexyl)-1-methylpentyl group, tert-butyl group, tert-pentyl group, and tert-hexyl group.

It is preferable that the aryl group for $R^{1\prime\prime}$ to $R^{3\prime\prime}$ each independently be a phenyl group or a naphthyl group.

There is no restriction on the alkyl groups for $R^{1\prime\prime}$ to $R^{3\prime\prime}$. Examples thereof include a linear, branched, or cyclic alkyl group of 1 to 10 carbon atoms. The number of carbon atoms is preferably 1 to 5, in terms of excellent resolution. Specific examples include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group. Of these, a methyl group is preferable, because it excels in resolution, and can be synthesized inexpensively.

In the case that two of $R^{1\prime\prime}$ to $R^{3\prime\prime}$ are mutually bonded to form a ring together with the sulfur atom, it is preferable to form a 3- to 10-membered ring including the sulfur ion, and it is more preferable to form a 5- to 7-membered ring including the sulfur ion.

In the case that two of $R^{1\prime\prime}$ to $R^{3\prime\prime}$ are mutually bonded to form a ring together with the sulfur atom, the other one of $R^{1\prime\prime}$ to $R^{3\prime\prime\prime}$ is preferably an aryl group. As the aryl group, the same aryl groups as those described above in the aryl group for $R^{1\prime\prime\prime}$ to $R^{3\prime\prime\prime}$ can be mentioned.

Specific examples of the cation moiety represented by the formula (b'-1) include triphenylsulfonium, (3,5-dimethylphenyl)diphenylsulfonium, (4-(2-adamantoxymethyloxy)-3,5-dimethylphenyl)diphenylsulfonium, (4-(2-adamantoxymethyloxy)phenyl)diphenylsulfonium, (4-(tert-butoxycarbonylmethyloxy)phenyl)diphenylsulfonium, (4-(tert-butoxycarbonylmethyloxy)-3,5-dimethylphenyl) diphenylsulfonium, (4-(2-methyl-2-adamantyloxycarbonylmethyloxy)phenyl) diphenylsulfonium, (4-(2-methyl-2-adamantyloxycarbonylmethyloxy)-3,5-dimethylphenyl) diphenylsulfonium, tri(4-methylphenyl)sulfonium, dimethyl (4-hydroxynaphthyl)sulfonium, monophenyldimethylsulfonium, diphenylmonomethylsulfonium, (4-methylphenyl)diphenylsulfonium, (4-methoxyphenyl)diphenylsulfonium, tri(4-tert-butyl)phenylsulfonium, diphenyl(1-(4-methoxy)naphthyl)sulfonium, di(1-naphthyl) phenylsulfonium, 1-phenyltetrahydrothiophenium, 1-(4-methylphenyl)tetrahydrothiophenium, 1-(3,5-dimethyl-4-hydroxyphenyl)tetrahydrothiophenium, 1-(4-methoxynaphthalene-1-yl)tetrahydrothiophenium, 1-(4-ethoxynaphthalene-1-yl)tetrahydrothiophenium, 1-(4-n-butoxynaphthalene-1-yl)tetrahydrothiophenium, 1-phenyltetrahydrothiopyranium, 1-(4-hydroxyphenyl)tetrahydrothiopyranium, 1-(3,5-dimethyl-4-hydroxyphenyl) tetrahydrothiopyranium, and 1-(4-methylphenyl)tetrahydrothiopyranium.

In the formula (b'-2), $R^{5\prime\prime\prime}$ and $R^{6\prime\prime\prime}$ each independently represents an aryl group or an alkyl group. At least one of $R^{5\prime\prime\prime}$ and $R^{6\prime\prime\prime}$ represents an aryl group. Both of $R^{5\prime\prime\prime}$ and $R^{6\prime\prime\prime}$ preferably represent aryl groups.

As the aryl groups for $R^{5\prime\prime\prime}$ and $R^{6\prime\prime\prime}$, the same aryl groups as those for $R^{1\prime\prime\prime}$ to $R^{3\prime\prime\prime}$ can be mentioned.

As the alkyl groups for $R^{5\prime\prime\prime}$ and $R^{6\prime\prime\prime}$, the same alkyl groups as those for $R^{1\prime\prime\prime}$ to $R^{3\prime\prime\prime}$ can be mentioned.

Of these, it is most preferable that both of $R^{5\prime\prime\prime}$ and $R^{6\prime\prime\prime}$ be phenyl groups.

Specific examples of the cation moiety represented by the formula (b'-2) include diphenyliodonium and bis(4-tert-butylphenyl)iodonium.

The alkyl group for $R^{40}$ to $R^{46}$ in the formulae (b-5) and (b-6) is preferably an alkyl group of 1 to 5 carbon atoms, more preferably a linear or branched alkyl group, and still more preferably a methyl group, an ethyl group, a propyl group, an isopropyl group, an n-butyl group, or a tert-butyl group.

The alkoxy group for $R^{42}$ to $R^{46}$ in the formula (b-5) and (b-6) is preferably an alkoxy group of 1 to 5 carbon atoms, more preferably a linear or branched alkoxy group, and particularly preferably a methoxy group or an ethoxy group.

The hydroxyalkyl group for $R^{41}$ to $R^{46}$ in the formula (b-5) and (b-6) is preferably a group in which one or more hydrogen atoms in the alkyl group for $R^{41}$ to $R^{46}$ are substituted with hydroxy groups, and examples thereof include a hydroxymethyl group, a hydroxyethyl group, and a hydroxypropyl group.

$n_0$ is preferably 0 or 1.

$n_1$ is preferably 0 to 2.

It is preferable that $n_2$ and $n_3$ each be independently 0 or 1, and it is more preferable that they be 0.

$n_4$ is preferably 0 to 2, and more preferably 0 or 1.

$n_5$ is preferably 0 or 1, and more preferably 0.

$n_6$ is preferably 0 or 1.

In the present invention, $A^+$ is preferably a cation moiety represented by the formula (b'-1) or (b-5), more preferably a cation moiety represented by formula (b'-1-1) to (b'-1-10), and (b-5-1) to (b-5-4) as shown below, and still more preferably a cation moiety which contains a triphenyl skelton, such as a cation moiety represented by formulae (b'-1-1) to (b'-1-8).

In the formula (b'-1-9) and (b'-1-10), $R^8$ and $R^9$ each independently represents a phenyl group which may contain a substituent group; a naphthyl group which may contain a substituent group; an alkyl group of 1 to 5 carbon atoms which may contain a substituent group; an alkoxy group; or a hydroxyl group.

u represents an integer of 1 to 3, and is most preferably 1 or 2.

[Chemical Formula 9]

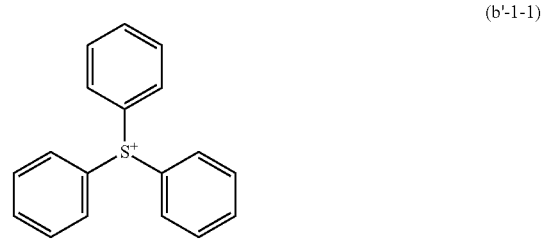

(b'-1-1)

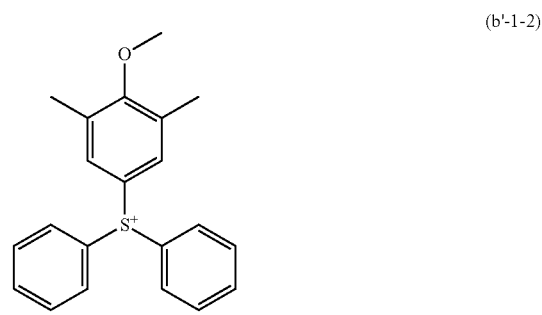

(b'-1-2)

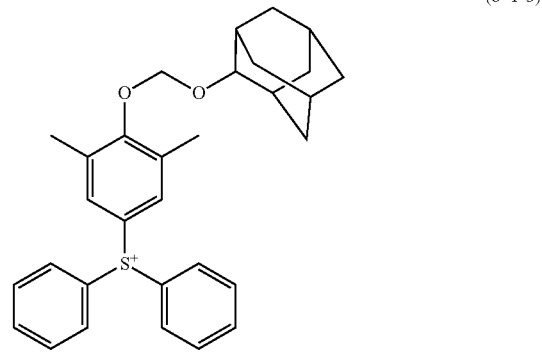

(b'-1-3)

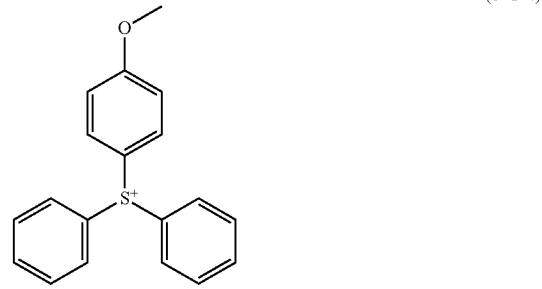

(b'-1-4)

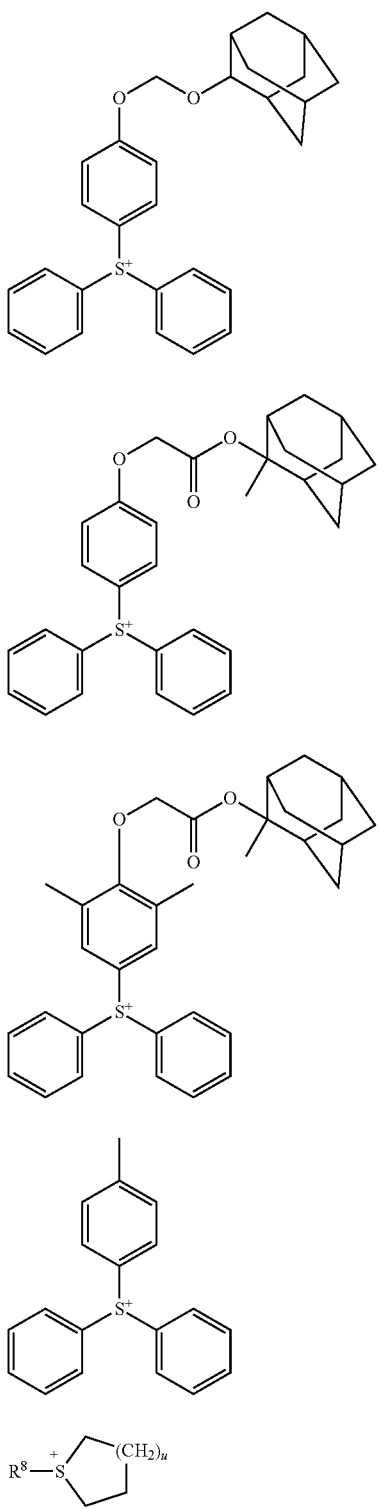
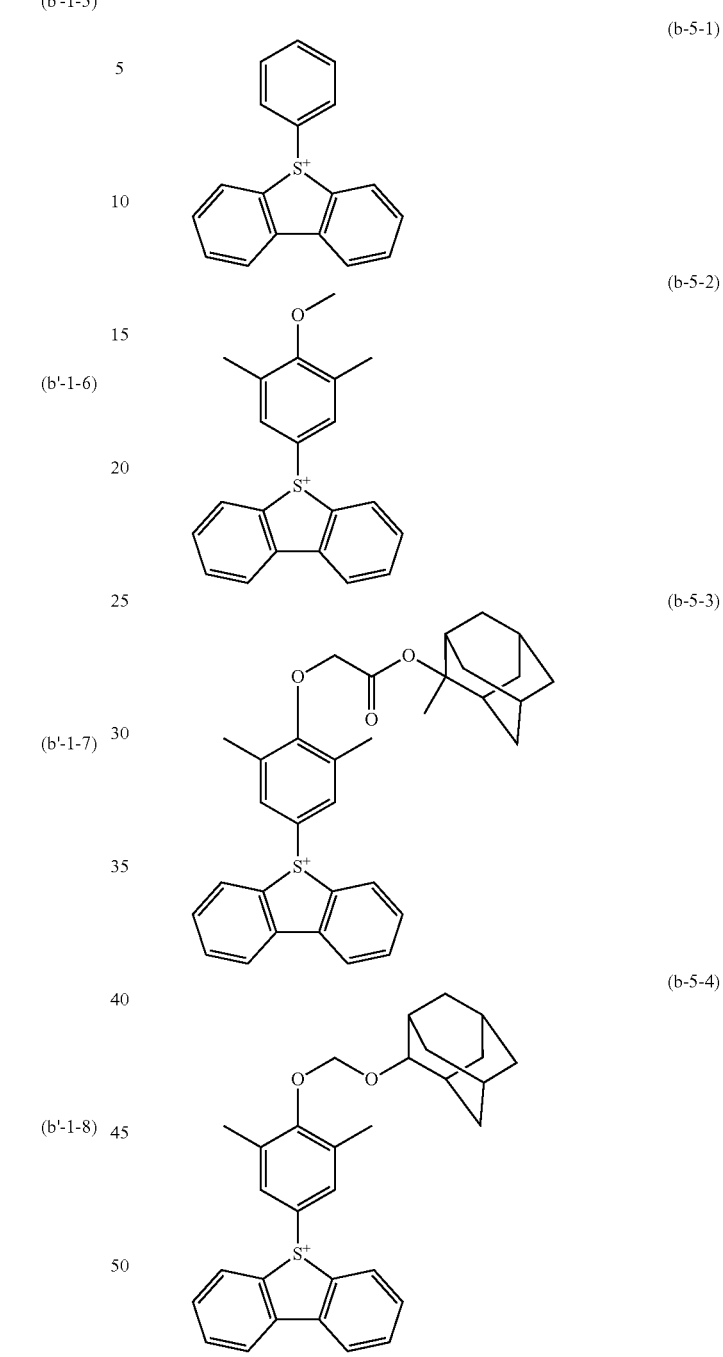

In the present invention, the compound (B1) is particularly preferably a compound which contains an anion moiety represented by the general formula (I-11) and a cation moiety represented by the formula (b'-1-1).

There is no particular restrictions on the method of manufacturing the compound (B1), and for example, the compound (B1) can be manufactured by reacting the aforementioned compound (I) with a compound (II) represented by a general formula (II) shown below.

[Chemical Formula 11]

$$A^+Z^- \quad (II)$$

(In the formula, $A^+$ is as defined above; and $Z^-$ represents a low-nucleophilic halogen ion, an ion which is capable of forming an acid exhibiting a lower acidity than the compound (I), $BF_4^-$, $AsF_6^-$, $SbF_6^-$, $PF_6^-$ or $ClO_4^-$.)

As the low-nucleophilic halogen ion for $Z^-$, a bromine ion and a chlorine ion can be mentioned.

Examples of the ion which are capable of forming an acid exhibiting a lower acidity than the compound (I) for $Z^-$ include a p-toluenesulfonate ion, a methanesulfonate ion, a benzenesulfonate ion, and a trifluoromethanesulfonate ion.

The compound (I) can be reacted with the compound (II), for example, by dissolving these compounds in a solvent such as water, dichloromethane, acetonitrile, methanol, chloroform, or methylene chloride, and stirring the solution obtained.

The reaction temperature is preferably 0 to 150° C., and more preferably 0 to 100° C. Usually, the reaction time is preferably 0.5 to 10 hours, and more preferably 1 to 5 hours, although it differs depending on the reactivity of the compound (I) and compound (II), the reaction temperature, or the like.

Usually, it is preferable that the amount of the compound (II) used in the above reaction be approximately 0.5 to 2 mol. relative to 1 mol of the compound (I).

The structure of the compound obtained by the above method can be confirmed by a general organic analysis method such as a $^1$H-nuclear magnetic resonance (NMR) spectrum method, a $^{19}$F-NMR spectrum method, an infrared resonance (IR) spectrum method, a mass spectrometry (MS) method, an element analysis method, and an X-ray crystallographic analysis method.

The compound (B1) is a novel compound which is available as an acid generator, and can be blended in a resist compound as an acid generator.

<<Acid Generator>>

The acid generator according to the third aspect of the present invention is composed of the compound (B1) described in the second aspect.

The acid generator is useful as an acid generator for a chemically-amplified resist composition, for example, as an acid generator component (B) of the resist composition according to the fourth aspect of the present invention, which is described below.

<<Resist Composition>>

A resist composition according to the fourth aspect of the present invention includes a base component (A) which displays changed solubility in an alkali developing solution under action of an acid (hereinafter, referred to as component (A)), and an acid generator component (B) which generates an acid upon exposure (hereinafter, referred to as component (B)), wherein the component (B) comprises an acid generator (B1) composed of the compound represented by the general formula (b1-1).

In a resist film formed by using the resist composition, an acid is generated from the component (B) when a selective exposure is conducted in the formation of the resist pattern, and the component (A) changes solubility in an alkali developing solution under action of acid thus generated from the component (B). As a result, whereas the exposed portions of the resist film change solubility in an alkali developing solution, the unexposed portions do not change solubility in an alkali developing solution. Therefore, if the resist composition is a positive resist composition, the exposed portions are dissolved to be removed by a developing treatment with alkali, thereby forming a resist pattern. On the other hand, if the resist composition is a negative resist composition, the unexposed portions are dissolved to be removed by a developing treatment with alkali, thereby forming a resist pattern.

The resist composition of the present invention may be a negative resist composition or a positive resist composition.

<Component (A)>

As the component (A), one kind of organic compound used as a base component for a chemically-amplified resist can be used alone, or two or more of them can be used in combination.

Here, the term "base component" means an organic compound which has a film-forming performance, and the molecular weight thereof is preferably 500 or more. When the molecular weight of the organic compound is 500 or more, the film-forming performance can be improved, and a nano-level resist pattern can easily be formed.

The organic compounds whose molecular weight is 500 or more can be classified broadly into a low molecular weight organic compound whose molecular weight is within a range from 500 to less than 2000 (hereinafter, referred to as low molecular weight compound), and a resin (polymer material) whose molecular weight is 2000 or more. As the low molecular weight compound, a non-polymer is usually used. In the case of using a resin (polymer, copolymer), the polystyrene equivalent molecular weight determined by gel permeation chromatography (GPC) is used as "molecular weight". Hereinafter, in the case of merely using the term "resin", it means a resin with a molecular weight of 2000 or more.

As the component (A), a resin which changes the solubility in an alkali solution under action of acid can be used, and also a low molecular weight compound which changes the solubility in an alkali solution under action of acid can be used.

In the case that the resist composition of the present invention is a negative resist composition, a resin soluble in an alkali developing solution is used as the component (A), and a cross-linking agent is blended with the negative resist composition.

In the negative resist composition, when acid is generated from the component (B) upon exposure, the action of this acid causes cross-linking reaction between the alkali-soluble resin and the cross-linking agent, and the cross-linked portion becomes poorly-soluble in an alkali developing solution. Therefore, in the formation of a resist pattern, when a resist film obtained by applying the negative resist composition on the substrate is subjected to selective exposure, the exposed area becomes poorly-soluble in an alkali developing solution, while the unexposed area remains soluble in the alkali developing solution, and hence a resist pattern can be formed by a developing treatment with an alkali.

A resin (hereinafter referred to as alkali-soluble resin) which is soluble in an alkali developing solution before exposure and changes to be insoluble after exposure is usually used as the component (A) of the negative resist composition.

As the alkali-soluble resin, it is preferable to use a resin having a structural unit derived from at least one of an α-(hydroxyalkyl)acrylic acid and a lower alkyl ester of α-(hydroxyalkyl)acrylic acid, because it enables formation of a satisfactory resist pattern with minimal swelling. Here, the term "α-(hydroxyalkyl) acrylic acid" represents one or both of an acrylic acid in which a hydrogen atom is bonded with the carbon atom at the α-position with which the carboxyl group bonded, and an α-hydroxyalkylacrylic acid in which a hydroxyalkyl group (preferably a hydroxyalkyl group of 1 to 5 carbon atoms) is bonded with the carbon atom at the α-position.

As a cross-linking agent, usually, an amino-based cross-linking agent such as a glycoluril that contains a methylol group or an alkoxymethyl group is preferable, because it enables an excellent resist pattern with minimal swelling to be formed. The blend quantity of the cross-linking agent is preferably within a range from 1 to 50 parts by weight, relative to 100 parts by weight of the alkali-soluble resin.

If the resist composition of the present invention is a positive resist composition, a base component which exhibits increased solubility in an alkali developing solution under action of acid can be used as the component (A). The component (A) is hardly-soluble in an alkali developing solution before exposure, and when an acid is generated from the component (B) upon exposure, the component (A) increases solubility in an alkali solution under action of acid. Therefore, in the formation of a resist pattern, when a resist film obtained by applying the positive resist composition on the substrate is subjected to selective exposure, the exposed area becomes soluble in an alkali, while the unexposed area remains insoluble in alkali, and hence a resist pattern can be formed by a developing treatment with an alkali.

In the resist composition of the present invention, the component (A) is preferably a base component which exhibits increased solubility in an alkali developing solution under action of acid. That is, the resist composition of the present invention is preferably a positive resist composition.

The component (A) may be a resin component (A1) which displays increased solubility in an alkali developing solution under action of acid (hereinafter, sometimes referred to as component (A1)), may be a low molecular weight compound (A2) which displays increased solubility in an alkali developing solution under action of acid (hereinafter, sometimes referred to as component (A2)), or may be a mixture of components (A1) and (A2). Of these, the component (A) preferably includes the component (A1).

[Component (A1)]

As the component (A1), one kind can be used alone selected from resin components (base resins) used as base components for a chemically-amplified resist, or two or more can be used in combination.

In the present invention, the component (A1) preferably contains a structural unit derived from an acrylate ester.

Here, the term "structural unit derived from an acrylate ester" in the present specification and claims represents a structural unit formed by cleavage of the ethylenic double bond of an acrylate ester.

The term "acrylate ester" is a concept containing an acrylate ester in which a hydrogen atom is bonded with a carbon atom at the α-position, and an α-substituted acrylate ester in which a hydrogen atom bonded with a carbon atom at the α-position is substituted with another substituent group (an atom or group other than a hydrogen atom). Examples of the substituent group include a lower alkyl group, and a halogenated lower alkyl group.

The term "α-position (carbon atom at the α-position)" in a structural unit derived from an acrylate ester means a carbon atom with which a carbonyl group is bonded, if not otherwise specified.

In the acrylate ester, specific examples of the lower alkyl group as the substituent group at the α-position include linear or branched lower alkyl groups such as a methyl group, an ethyl group, a propyl group, an isopropyl group, an n-butyl group, an isobutyl group, a tert-butyl group, a pentyl group, an isopentyl group, or a neopentyl group.

Specific examples of the halogenated lower alkyl group include groups in which a part or all of the hydrogen atoms of the aforementioned "lower alkyl group for the substituent group at the α-position" are substituted with halogen atoms. Examples of the halogen atom include a fluorine atom, a chlorine atom, an iodine atom, and a bromine atom. Of these, a fluorine atom is preferable.

In the present invention, the group which is bonded with the α-position is preferably a hydrogen atom, a lower alkyl group or a halogenated lower alkyl group; more preferably a hydrogen atom, a lower alkyl group or a fluorinated lower alkyl group; and still more preferably a hydrogen atom or a methyl group, in terms of industrial availability.

The component (A1) particularly preferably includes a structural unit (a1) derived from an acrylate ester which has an acid dissociable, dissolution inhibiting group.

Also, it is preferable that the component (A1) further includes a structural unit (a2) derived from an acrylate ester which has a lactone-containing cyclic group, in addition to the structural unit (a1).

Also, it is preferable that the component (A1) further include a structural unit (a3) derived from an acrylate ester which contains a polar group-containing aliphatic hydrocarbon group, in addition to the structural unit (a1), or the structural units (a1) and (a2).

Structural Unit (a1)

As the acid dissociable, dissolution inhibiting group in the structural unit (a1), any of the groups that have been proposed as acid dissociable, dissolution inhibiting groups for the base resins of chemically amplified resists can be used, provided the group has an alkali dissolution-inhibiting effect that renders the entire component (A1) alkali-insoluble prior to dissociation, and then following dissociation by action of acid, causes the entire component (A1) to change to an alkali-soluble state. Generally, groups that form either a cyclic or chain-like tertiary alkyl ester with the carboxyl group of the (meth)acrylic acid; and acetal-type acid dissociable, dissolution inhibiting groups such as alkoxyalkyl groups are widely known.

Here, the term "tertiary alkyl ester" means a structure in which an ester is formed by substituting the hydrogen atom of a carboxyl group with a chain-like or cyclic alkyl group, and a tertiary carbon atom within the chain-like or cyclic alkyl group is bonded with the oxygen atom at the terminal of the carbonyloxy group (—C(O)—O—). In the tertiary alkyl ester, the bond of the oxygen atom with the tertiary carbon atom is cleaved by the action of acid.

Here, the chain-like or cyclic alkyl group may contain a substituent group.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of the tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

The term "aliphatic branched" means a branched structure having no aromaticity.

The "aliphatic branched, acid dissociable, dissolution inhibiting group" is not limited to groups (hydrocarbon groups) composed of carbon atoms and hydrogen atoms, and is preferably a hydrocarbon group. Further, the "hydrocarbon group" may be either saturated or unsaturated, and is preferably saturated.

Examples of aliphatic branched, acid dissociable, dissolution inhibiting groups include tertiary alkyl groups of 4 to 8 carbon atoms, and specific examples include a tert-butyl group, a tert-pentyl group and a tert-heptyl group.

The term "aliphatic cyclic group (alicyclic group)" means a monocyclic or polycyclic group which has no aromaticity.

The "aliphatic cyclic group" within the structural unit (a1) may or may not contain a substituent group. Examples of substituent groups include a lower alkyl group of 1 to 5 carbon atoms, a fluorine atom, a fluorinated lower alkyl group of 1 to 5 carbon atoms, and an oxygen atom (=O).

The basic ring of the "aliphatic cyclic group" exclusive of substituent groups is not limited to groups (hydrocarbon groups) composed of carbon atoms and hydrogen atoms, and is preferably a hydrocarbon group. Further, the "hydrocarbon group" may be either saturated or unsaturated, and is preferably saturated. The "aliphatic cyclic group" is preferably a polycyclic group.

Examples of the aliphatic cyclic groups include groups in which one or more hydrogen atoms have been removed from a monocycloalkane or a polycycloalkane such as a bicycloalkane, tricycloalkane or tetracycloalkane in which a lower alkyl group, a fluorine atom or a fluorinated lower alkyl group may or may not be included as a substituent group. Specific examples include groups in which at least one hydrogen atom has been removed from a monocycloalkane such as cyclopentane and cyclohexane; and groups in which at least one hydrogen atom has been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cycloalkyl group can be mentioned. Specific examples thereof include a 2-methyl-2-adamantyl group and a 2-ethyl-2-adamantyl group. Further, in the structural units represented by general formulae (a1″-1) to (a1″-6) shown below, groups bonded with the oxygen atom of the carbonyloxy group (—C(O)—O—), that is, groups having an aliphatic cyclic group such as an adamantyl group, a cyclohexyl group, a cyclopentyl group, a norbornyl group, a tricyclodecanyl group or a tetracyclodecanyl group, and a branched alkylene group having a tertiary carbon atom bonded thereto, can be mentioned.

[Chemical Formula 12]

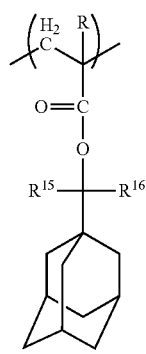

(a1″-1)

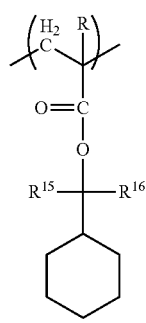

(a1″-2)

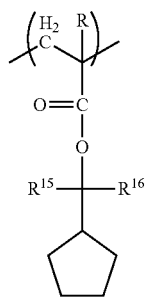

(a1″-3)

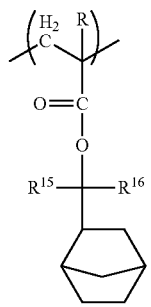

(a1″-4)

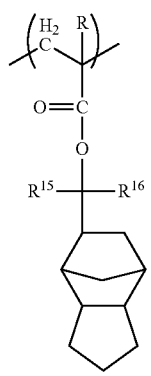

(a1″-5)

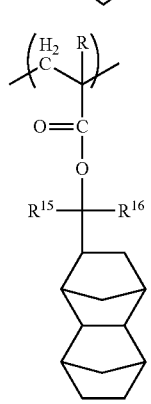

(a1″-6)

(In the formula, R represents a hydrogen atom, a lower alkyl group or a halogenated lower alkyl group; and $R^{15}$ and $R^{16}$ each independently represents an alkyl group (which may be linear or branched, and is preferably an alkyl group of 1 to 5 carbon atoms).)

In the general formulae (a1″-1) to (a1″-6), the lower alkyl group or halogenated lower alkyl group for R are the same as the lower alkyl group or halogenated lower alkyl group which can be bonded with the α-position of the aforementioned acrylate ester.

An "acetal-type acid dissociable, dissolution inhibiting group" generally replaces a hydrogen atom at the terminal of an alkali-soluble group such as a carboxy group or a hydroxyl group, so as to be bonded with an oxygen atom. When acid is generated upon exposure, the generated acid acts to break the bond between the acetal-type acid dissociable, dissolution inhibiting group and the oxygen atom with which the acetal-type, acid dissociable, dissolution inhibiting group is bonded.

Examples of the acetal-type acid dissociable, dissolution inhibiting groups include groups represented by a general formula (p1) shown below.

[Chemical Formula 13]

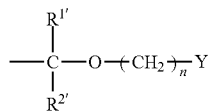

(p1)

(In the formula, $R^{1\prime}$ and $R^{2\prime}$ each independently represents a hydrogen atom or a lower alkyl group; n represents an integer of 0 to 3; and Y represents a lower alkyl group or an aliphatic cyclic group.)

In the above formula, n is preferably an integer of 0 to 2, more preferably 0 or 1, and most preferably 0.

As the lower alkyl group for $R^{1\prime}$ or $R^{2\prime}$, the same lower alkyl groups as those described above in R can be mentioned. As the lower alkyl group of $R^{1\prime}$ or $R^{2\prime}$, a methyl group or an ethyl group is preferable, and a methyl group is most preferable.

In the present invention, at least one of $R^{1\prime}$ and $R^{2\prime}$ is preferably a hydrogen atom. That is, it is preferable that the acid dissociable, dissolution inhibiting group (p1) be a group represented by a general formula (p1-1) shown below.

[Chemical Formula 14]

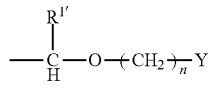

(p1-1)

(In the formula, $R^{1\prime}$, n, and Y are as defined above.)

As the lower alkyl group for Y, the same lower alkyl groups as those described above in R can be mentioned.

As the aliphatic cyclic group for Y, any of the aliphatic monocyclic or polycyclic groups which have been proposed for conventional ArF resists and the like can be used by being appropriately selected. For example, the same groups described above in the "aliphatic cyclic group" can be mentioned.

Further, as the acetal-type, acid dissociable, dissolution inhibiting group, groups represented by general formula (p2) shown below can also be mentioned.

[Chemical Formula 15]

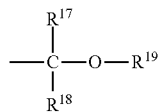

(p2)

(In the formula, $R^{17}$ and $R^{18}$ each independently represents a linear or branched alkyl group or a hydrogen atom; and $R^{19}$ represents a linear, branched, or cyclic alkyl group. Alternately, $R^{17}$ and $R^{19}$ each independently represents a linear or branched alkylene group, wherein the terminal of $R^{17}$ may be bonded with the terminal of $R^{19}$ thereby forming a ring.)

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

Particularly, it is preferable that one of $R^{17}$ and $R^{18}$ be a hydrogen atom, and the other be a methyl group.

$R^{19}$ represents a linear, branched or cyclic alkyl group which preferably has 1 to 15 carbon atoms, and may be linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cyclic alkyl group, it preferably has 4 to 15 carbon atoms, more preferably 4 to 12 carbon atoms, and most preferably 5 to 10 carbon atoms. Specific examples of the cyclic alkyl group include groups in which one or more hydrogen atoms have been removed from a monocycloalkane or a polycycloalkane such as a bicycloalkane, tricycloalkane or tetracycloalkane, in which a fluorine atom or a fluorinated alkyl group may or may not be included as a substituent group. Specific examples thereof include groups in which one or more hydrogen atoms have been removed from a monocycloalkane such as cyclopentane and cyclohexane, and a polycycloalkane such as adamantane, norbornane, isobornane, tricyclodecane, and tetracyclododecane. Of these, a group in which one or more hydrogen atoms have been removed from adamantane is preferable.

In the general formula (p2), $R^{17}$ and $R^{19}$ may each independently represent a linear or branched alkylene group (preferably an alkylene group of 1 to 5 carbon atoms), and the terminal of $R^{19}$ may be bonded with the terminal of $R^{17}$.

In such a case, a cyclic group is formed by $R^{17}$, $R^{19}$, the oxygen atom with which $R^{19}$ is bonded, and the carbon atom with which the oxygen atom and $R^{17}$ are bonded. Such a cyclic group is preferably a 4- to 7-membered ring, and more preferably a 4- to 6-membered ring. Specific examples of the cyclic group include a tetrahydropyranyl group and a tetrahydrofuranyl group.

As the structural unit (a1), it is preferable to use at least one member selected from the group consisting of structural units represented by a general formula (a1-0-1) shown below and structural units represented by a general formula (a1-0-2) shown below.

[Chemical Formula 16]

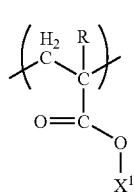

(a1-0-1)

(In the formula, R represents a hydrogen atom, a lower alkyl group or a halogenated lower alkyl group; and $X^1$ represents an acid dissociable, dissolution inhibiting group.)

[Chemical Formula 17]

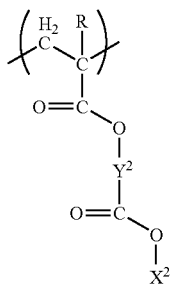
(a1-0-2)

(In the formula, R represents a hydrogen atom, a lower alkyl group or a halogenated lower alkyl group; $X^2$ represents an acid dissociable, dissolution inhibiting group; and $Y^2$ represents an alkylene group or an aliphatic cyclic group.)

In the general formula (a1-0-1), the lower alkyl group or halogenated lower alkyl group for R are the same as the lower alkyl group or halogenated lower alkyl group which can be bonded with the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In the general formula (a1-0-2), R is as defined above.

$X^2$ is the same as $X^1$ described in the general formula (a1-0-1).

$Y^2$ is preferably an alkylene group of 1 to 10 carbon atoms or a bivalent aliphatic cyclic group. As the aliphatic cyclic group, the same aliphatic cyclic groups as those described in the explanation of "aliphatic cyclic group" can be used, with the exception that two or more hydrogen atoms are removed.

When $Y^2$ represents an alkylene group of 1 to 10 carbon atoms, it is more preferable that the number of carbon atoms be 1 to 6, still more preferably 1 to 4, and most preferably 1 to 3.

When $Y^2$ represents a bivalent aliphatic cyclic group, it is particularly preferable that the bivalent aliphatic cyclic group be a group in which two or more hydrogen atoms have been removed from a cyclopentane, a cyclohexane, a norbornane, an isobornane, an adamantane, a tricyclodecane or a tetracyclododecane.

Specific examples of the structural unit (a1) include structural units represented by the general formulae (a1-1) to (a1-4) shown below.

[Chemical Formula 18]

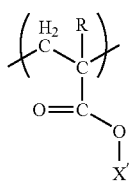
(a1-1)

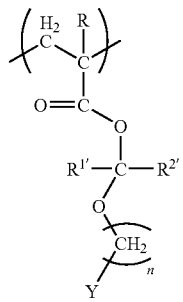
(a1-2)

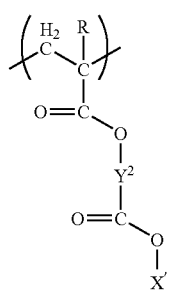
(a1-3)

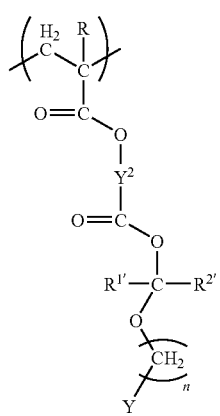
(a1-4)

(In the formula, X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents an alkylene group or an aliphatic cyclic group; R is as defined above; $R^{1\prime}$ and $R^{2\prime}$ each independently represents a hydrogen atom or a lower alkyl group of 1 to 5 carbon atoms.)

In the formula, as X', the same tertiary alkyl ester-type acid dissociable, dissolution inhibiting group as those described in $X^1$ can be mentioned.

$R^{1\prime}$, $R^{2\prime}$, n, and Y are the same as $R^{1\prime}$, $R^{2\prime}$, n, and Y in the general formula (p1) shown above in "acetal-type acid dissociable, dissolution inhibiting group".

$Y^2$ is the same as $Y^2$ in the general formula (a1-0-2).

Specific examples of structural units represented by the general formulae (a1-1) to (a1-4) shown above include the following.

[Chemical Formula 19]
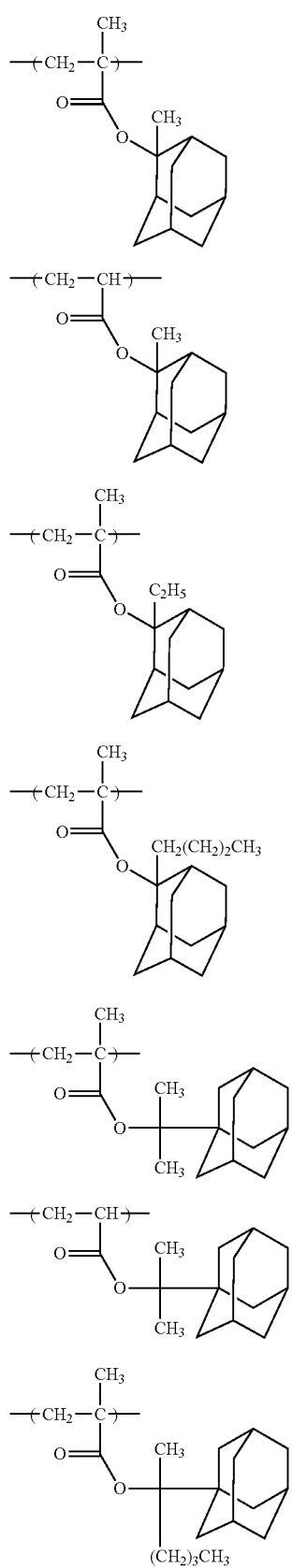
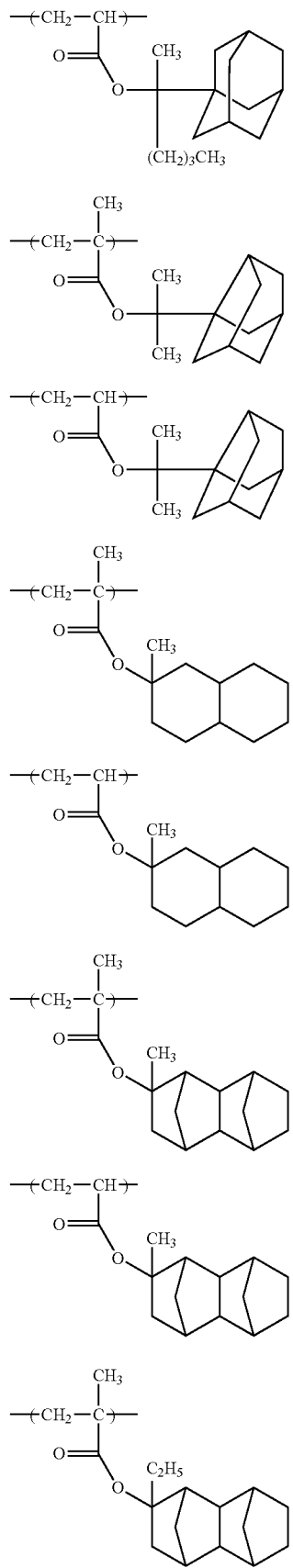

(a1-1-16)
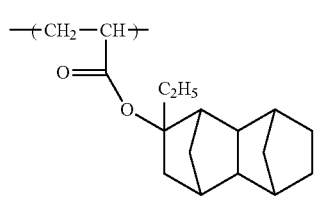
[Chemical Formula 20]
(a1-1-17)
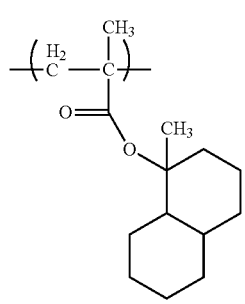
(a1-1-18)
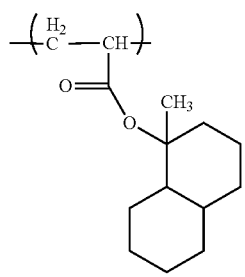
(a1-1-19)
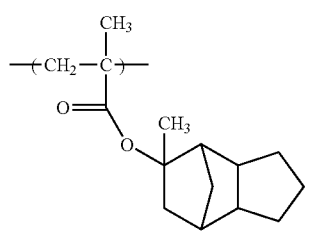
(a1-1-20)
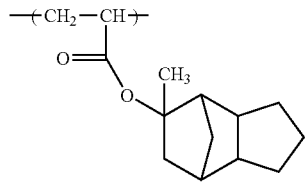
(a1-1-21)
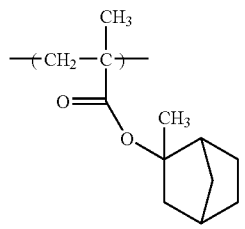
(a1-1-22)
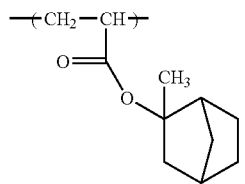
(a1-1-23)
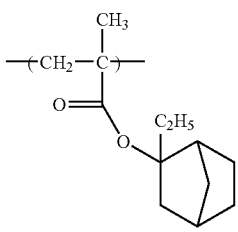
(a1-1-24)
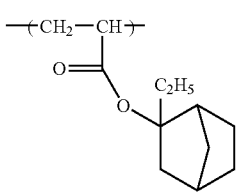
(a1-1-25)
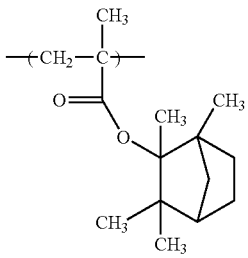
(a1-1-26)
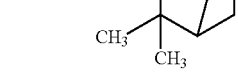
(a1-1-27)
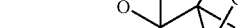
(a1-1-28)

(a1-1-29)
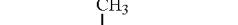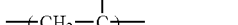

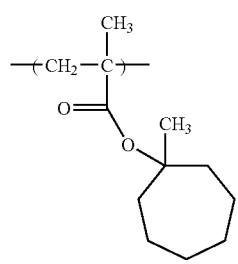 (a1-1-30)
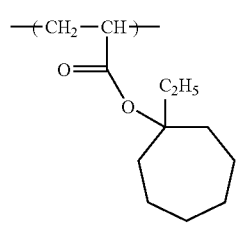 (a1-1-31)
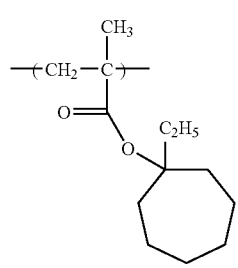 (a1-1-32)
[Chemical Formula 21]
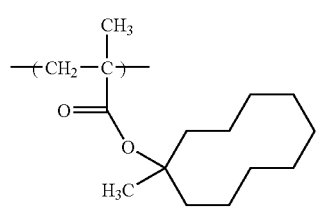 (a1-1-33)
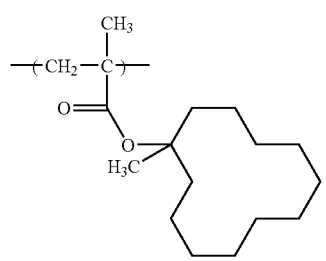 (a1-1-34)
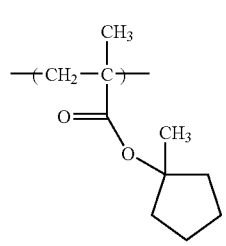 (a1-1-35)
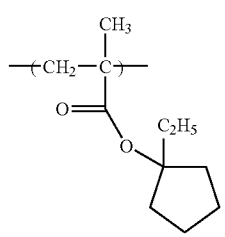 (a1-1-36)
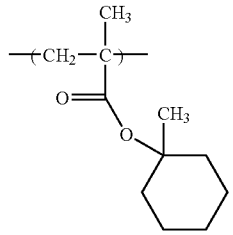 (a1-1-37)
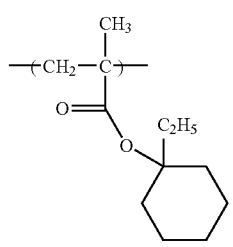 (a1-1-38)
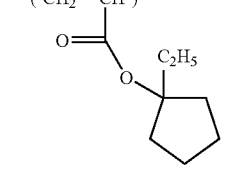 (a1-1-39)
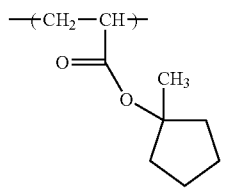 (a1-1-40)
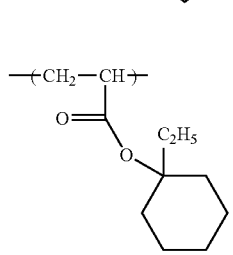 (a1-1-41)
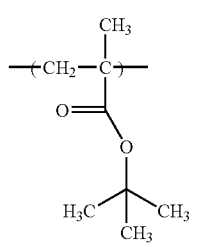 (a1-1-42)

(a1-1-43) 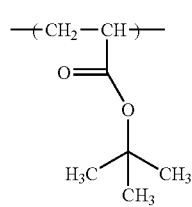
(a1-1-44) 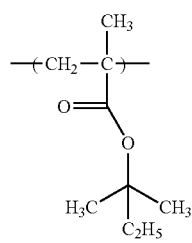
(a1-1-45) 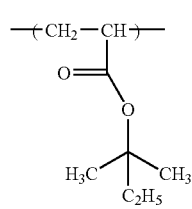
[Chemical Formula 22]
(a1-2-1) 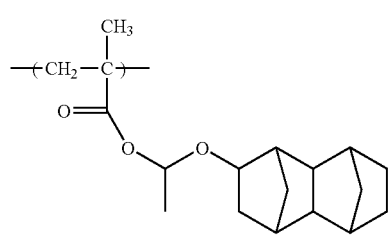
(a1-2-2) 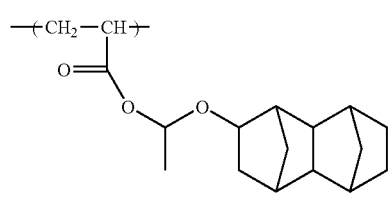
(a1-2-3) 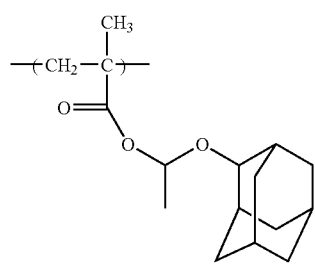
(a1-2-4) 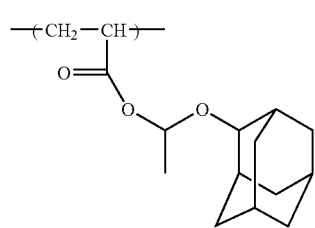
(a1-2-5) 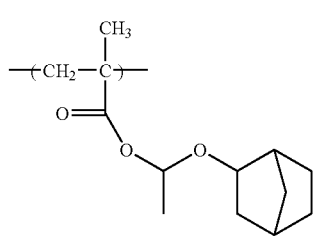
(a1-2-6) 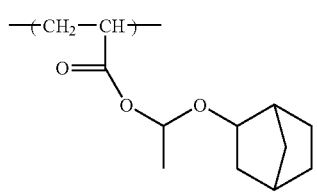
[Chemical Formula 23]
(a1-2-7) 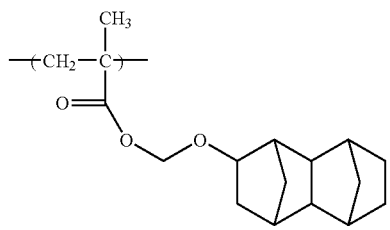
(a1-2-8) 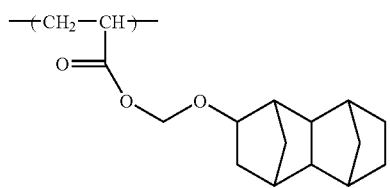
(a1-2-9) 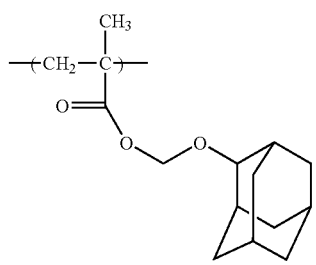
(a1-2-10) 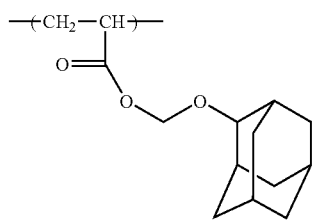
(a1-2-11)

(a1-2-12) 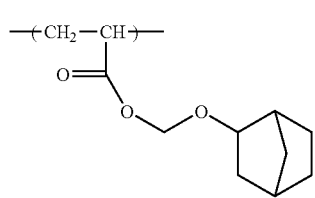
(a1-2-13) 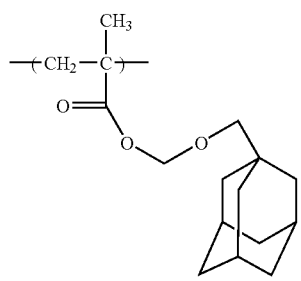
(a1-2-14) 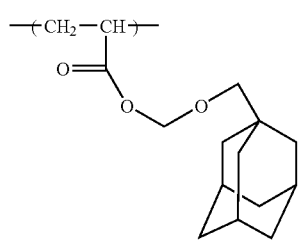
(a1-2-15) 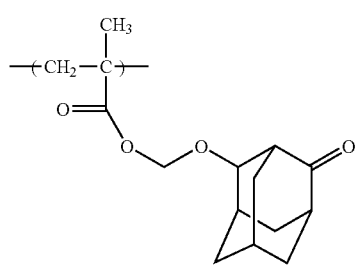
(a1-2-16) 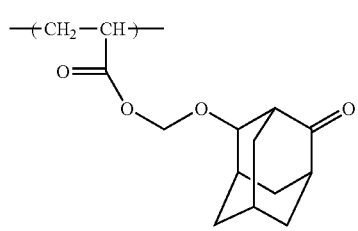
(a1-2-17) 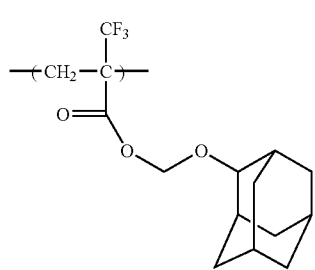
(a1-2-18) 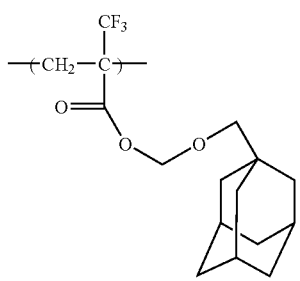
(a1-2-19) 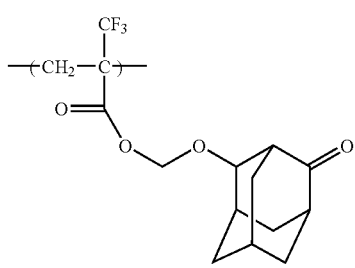
(a1-2-20) 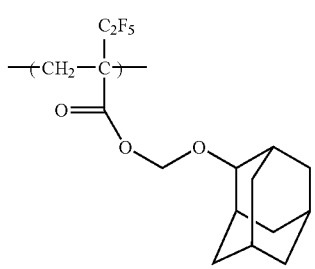
[Chemical Formula 24]
(a1-2-21) 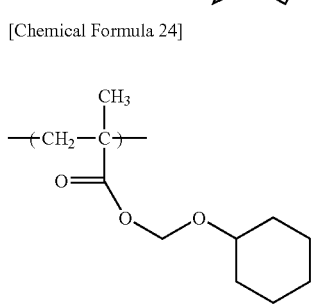
(a1-2-22) 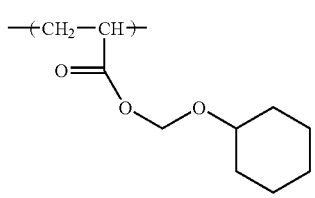
(a1-2-23) 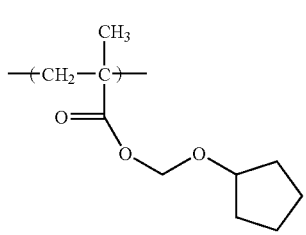

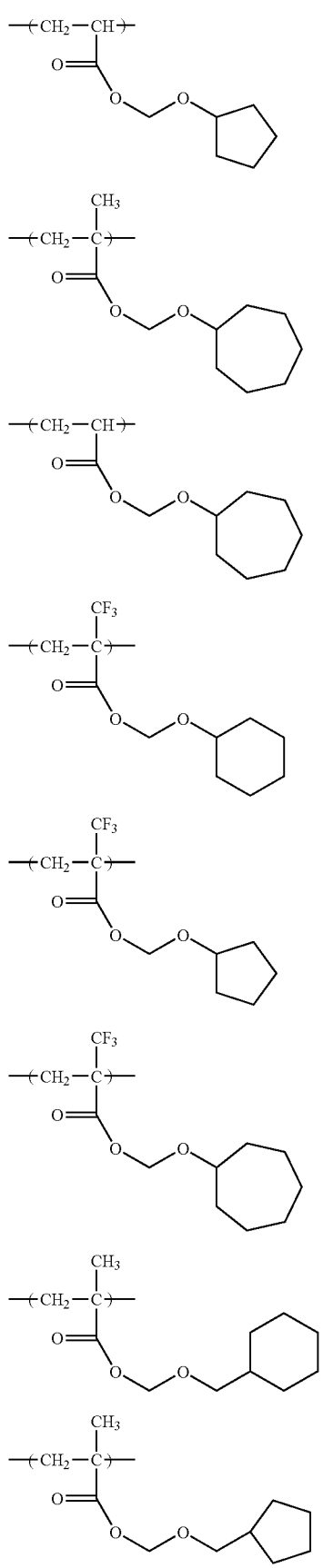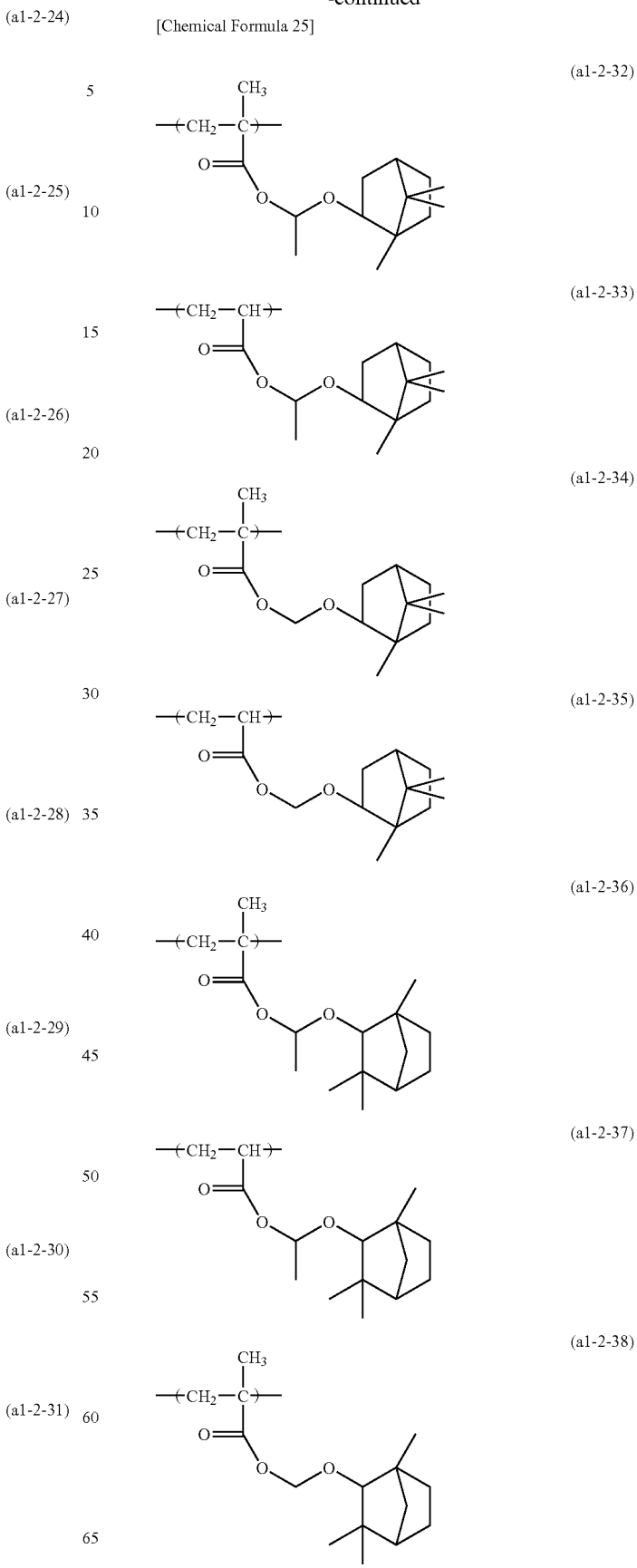

(a1-2-39)
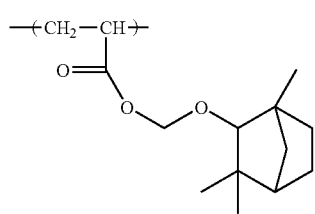
[Chemical Formula 26]
(a1-3-1)
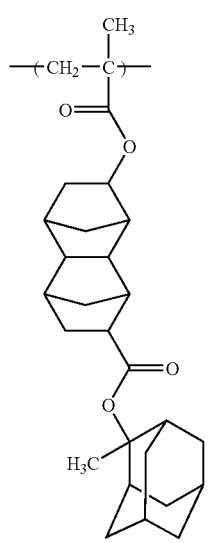
(a1-3-2)
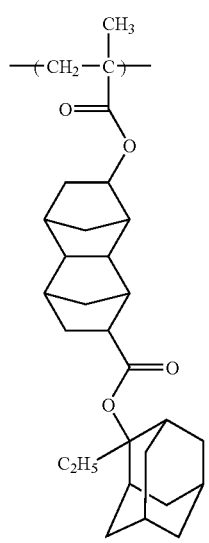
(a1-3-3)
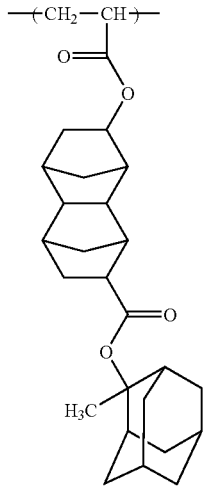
(a1-3-5)
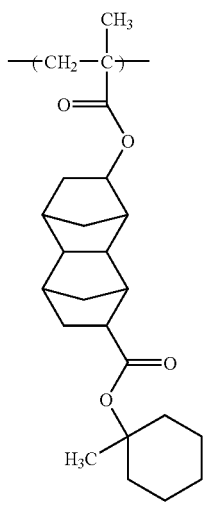
(a1-3-6)
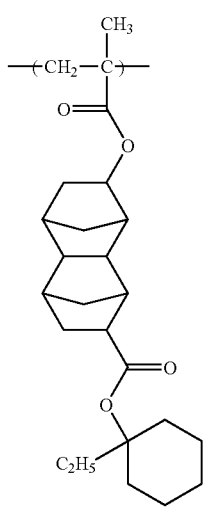

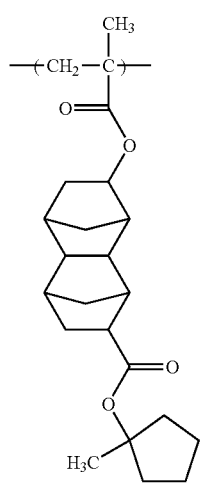
(a1-3-7)
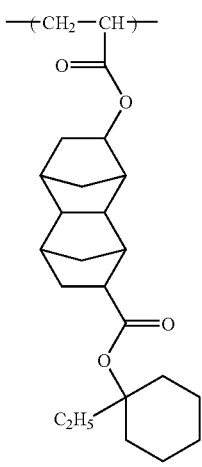
(a1-3-10)
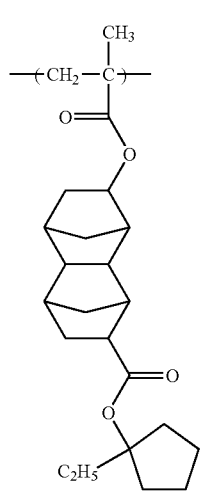
(a1-3-8)
(a1-3-11)
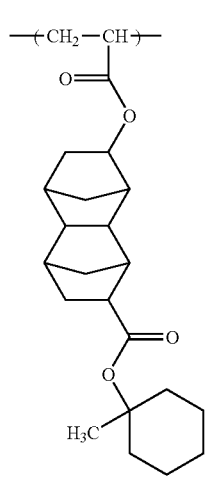
(a1-3-9)
(a1-3-12)

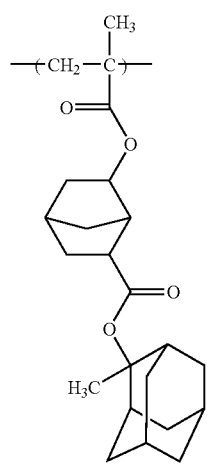
(a1-3-13)
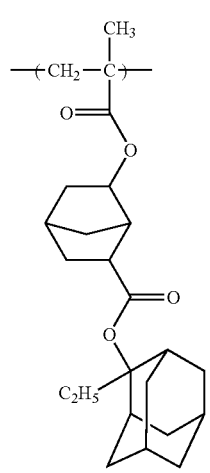
(a1-3-14)
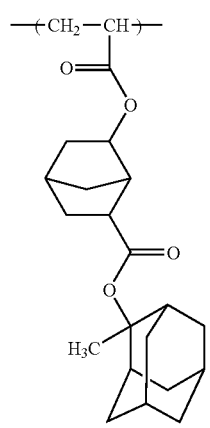
(a1-3-15)
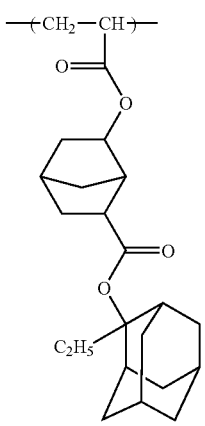
(a1-3-16)
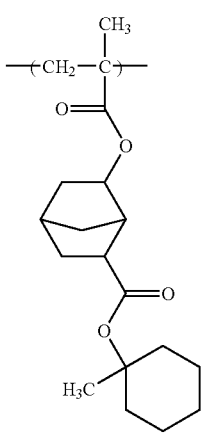
(a1-3-17)
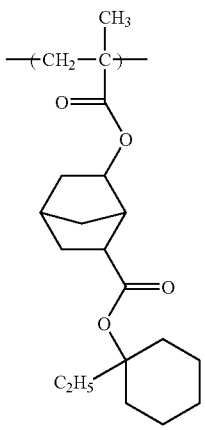
(a1-3-18)

[Chemical Formula 27]
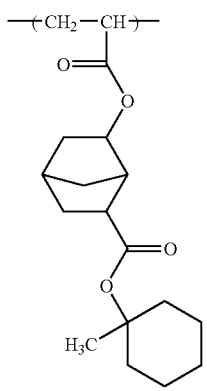
(a1-3-19)
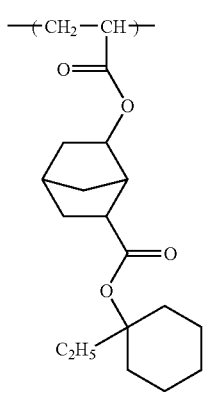
(a1-3-20)
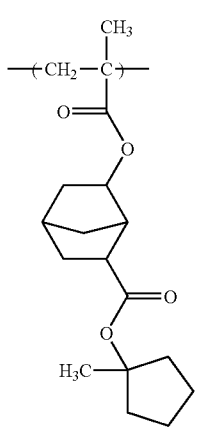
(a1-3-21)
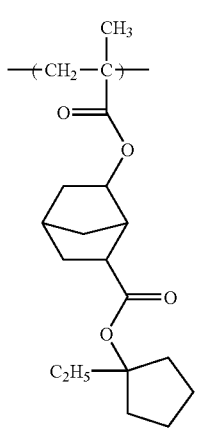
(a1-3-22)
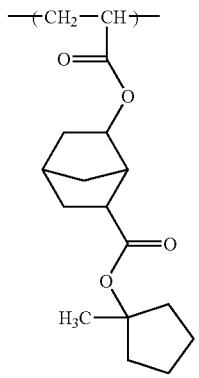
(a1-3-23)
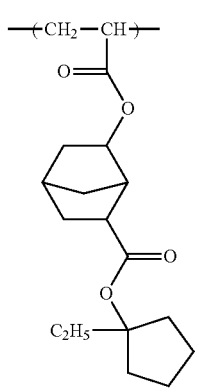
(a1-3-24)
[Chemical Formula 28]
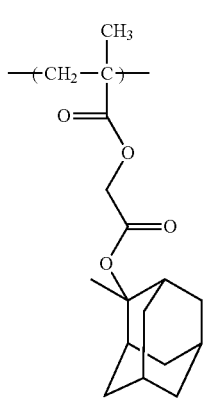
(a1-3-25)
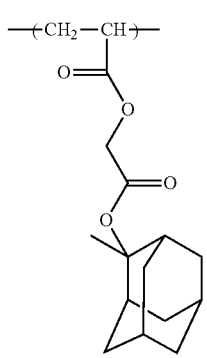
(a1-3-26)

(a1-3-27)
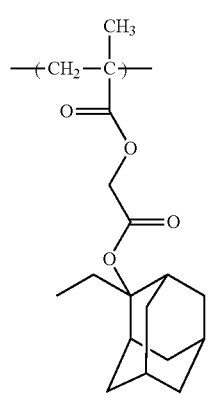
(a1-3-28)
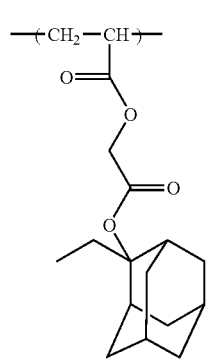
(a1-3-29)
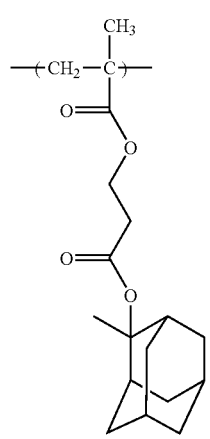
(a1-3-30)
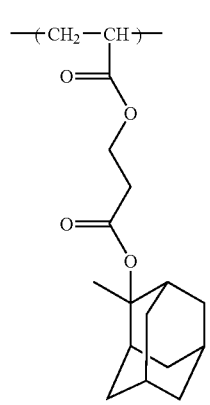
(a1-3-31)
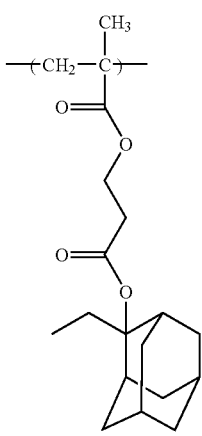
(a1-3-32)
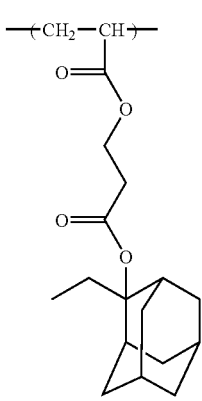
(a1-3-33)
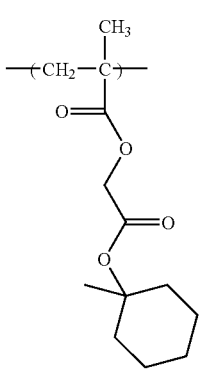
(a1-3-34)

(a1-3-35) 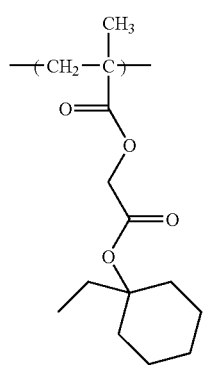
(a1-3-36) 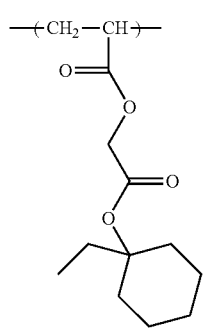
[Chemical Formula 29]
(a1-3-37) 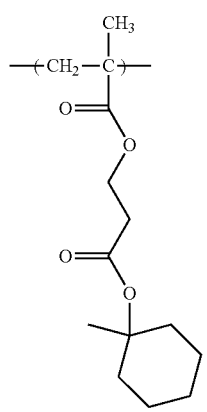
(a1-3-38) 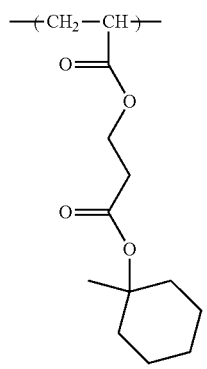
(a1-3-39) 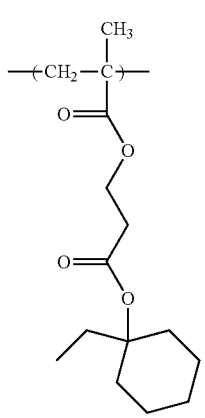
(a1-3-40) 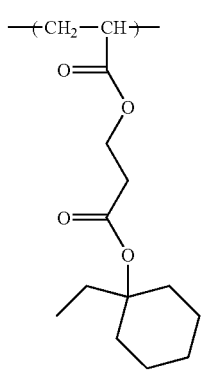
(a1-3-41) 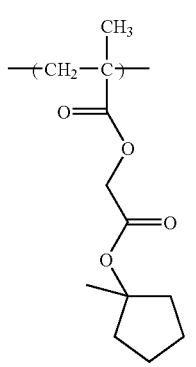
(a1-3-42) 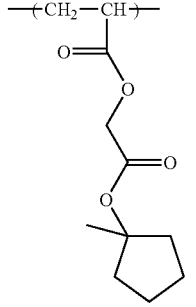

(a1-3-43)
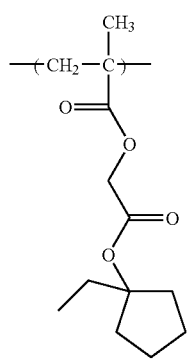
(a1-3-44)
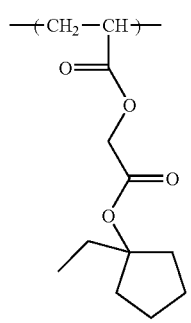
(a1-3-45)
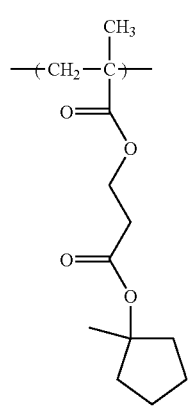
(a1-3-46)
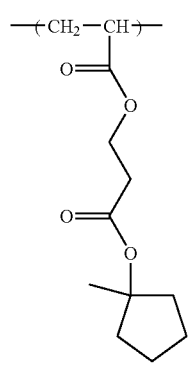
(a1-3-47)
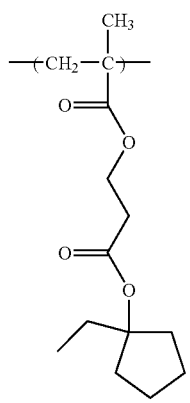
(a1-4-48)
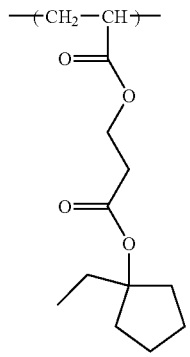
[Chemical Formula 30]
(a1-4-1)
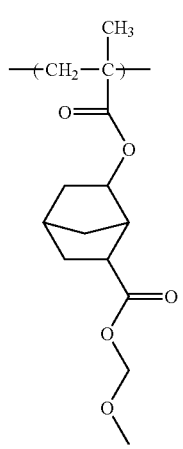
(a1-4-2)
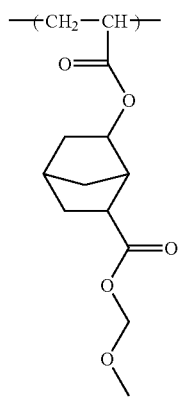

-continued
(a1-4-3)
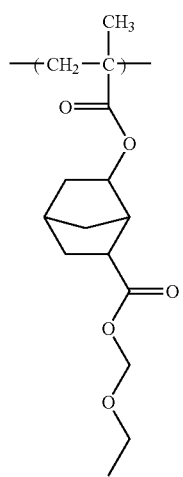
(a1-4-4)
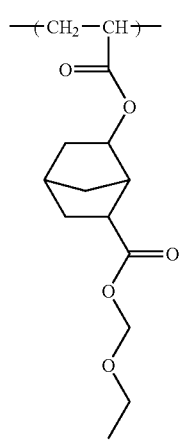
(a1-4-5)
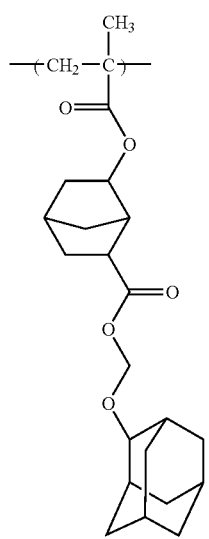
-continued
(a1-4-6)
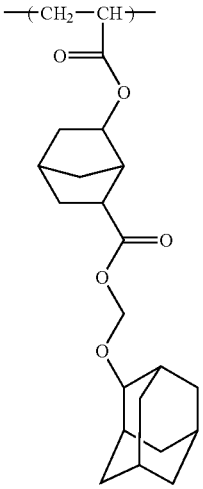
(a1-4-7)
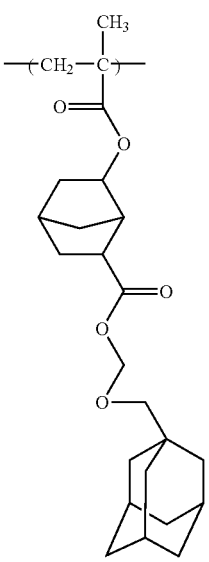
(a1-4-8)
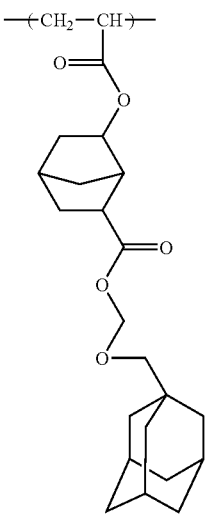

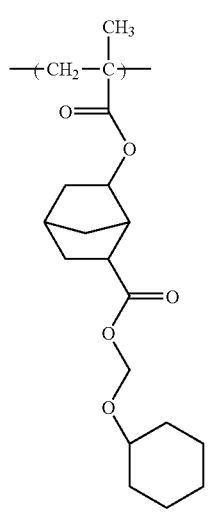
(a1-4-9)
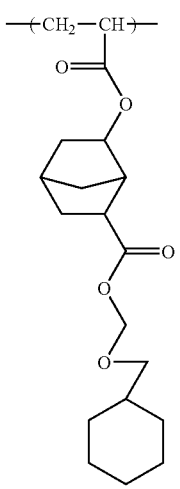
(a1-4-12)
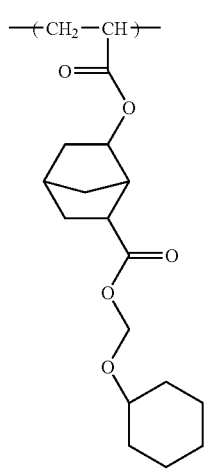
(a1-4-10)
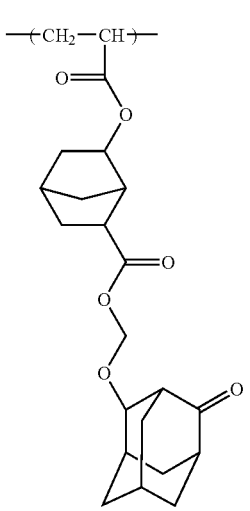
(a1-4-13)
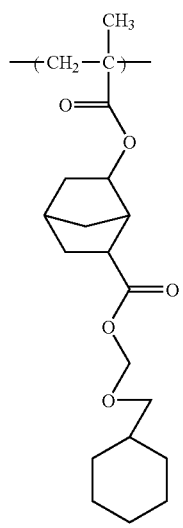
(a1-4-11)
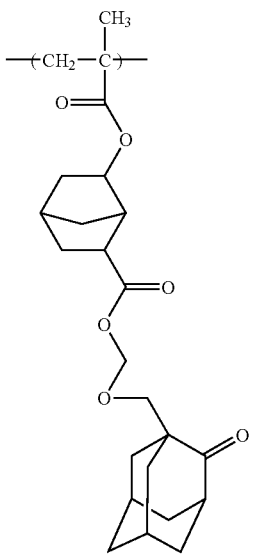
(a1-4-14)

(a1-4-15)
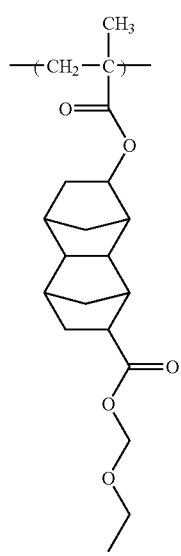
(a1-4-16)
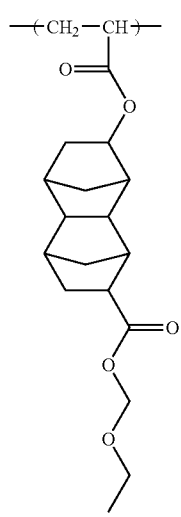
(a1-4-17)
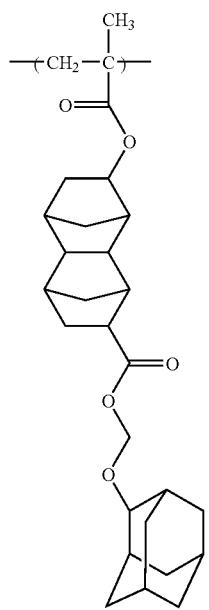
[Chemical Formula 31]
(a1-4-18)
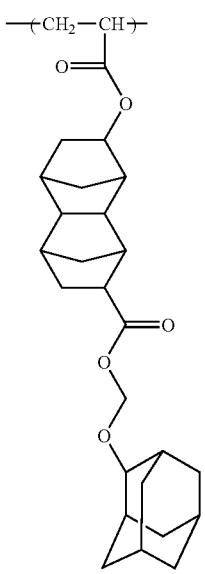
(a1-4-19)
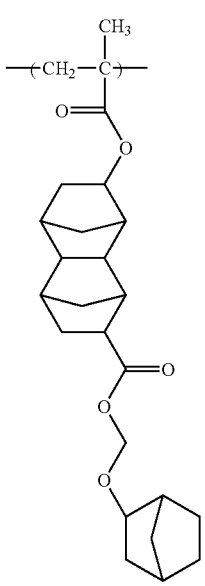

(a1-4-20)
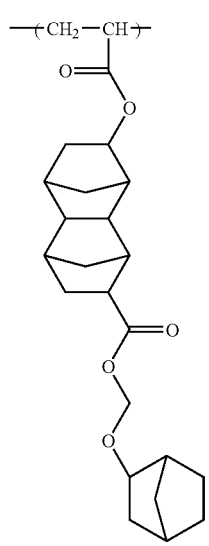
(a1-4-21)
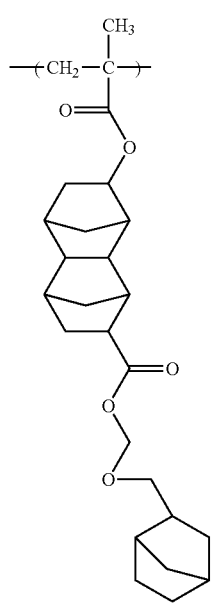
(a1-4-22)
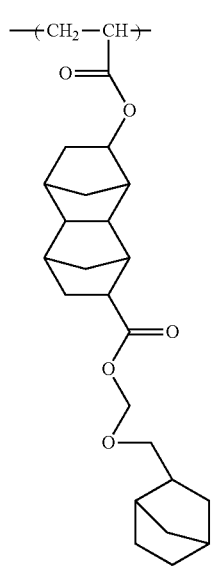
(a1-4-23)
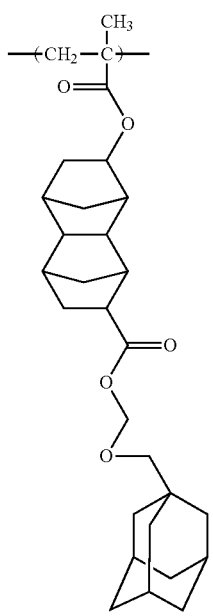
(a1-4-24)
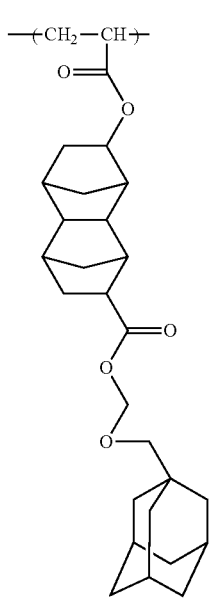

(a1-4-25)
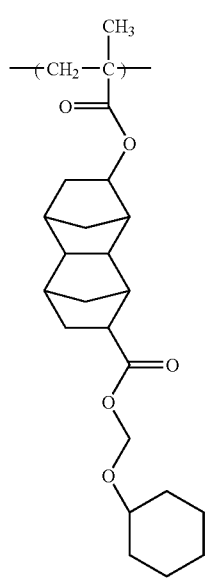
(a1-4-26)
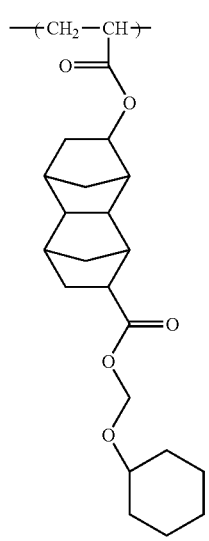
(a1-4-27)
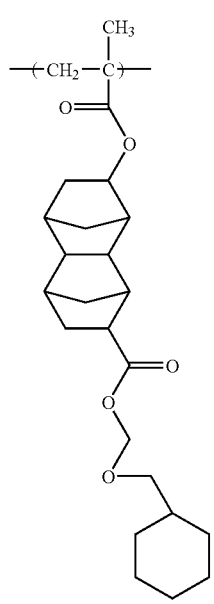
(a1-4-28)
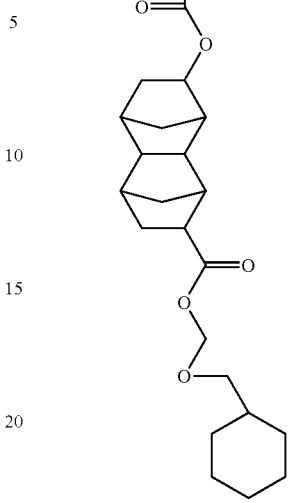
(a1-4-29)
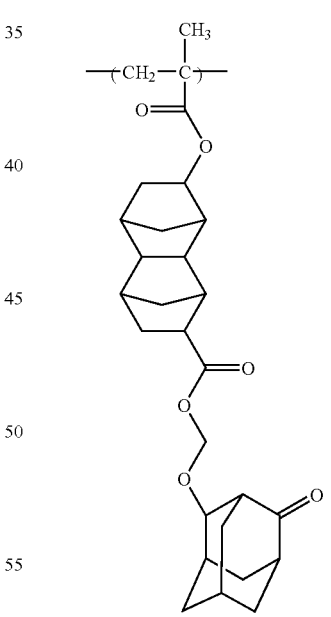

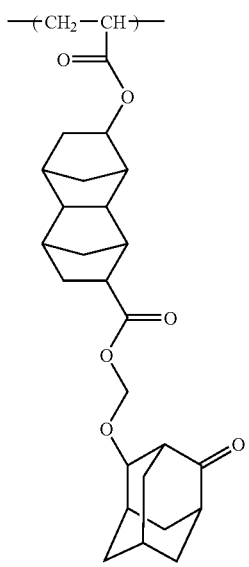

(a1-4-30)

The structural unit (a1) can be used alone, or in combinations of two or more different units.

Of these, a structural unit represented by the general formula (a1-1) is preferable, and it is more preferable to use at least one selected from the group consisting of the general formulae (a1-1-1) to (a1-1-6), and (a1-1-35) to (a1-1-41).

Further, as the structural unit (a1), structural units represented by a general formula (a1-1-01) shown below which includes the structural units represented by formulae (a1-1-1) to (a1-1-4), and structural units represented by a general formula (a1-1-02) shown below which includes the structural units represented by formulae (a1-1-35) to (a1-1-41) are also preferable.

[Chemical Formula 32]

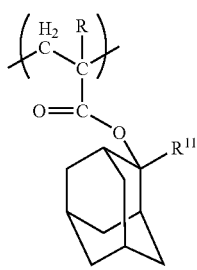

(a1-1-01)

(In the formula, R represents a hydrogen atom, a lower alkyl group or a halogenated lower alkyl group; and $R^{11}$ represents a lower alkyl group.)

[Chemical Formula 33]

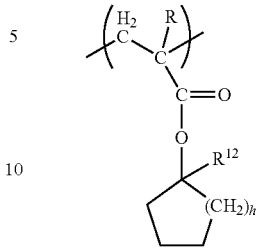

(a1-1-02)

(In the formula, R represents a hydrogen atom, a lower alkyl group, or a halogenated lower alkyl group; $R^{12}$ represents a lower alkyl group; and h represents an integer of 1 to 3.)

In the general formula (a1-1-01), R is as defined above.
The lower alkyl group for $R^{11}$ is the same as the lower alkyl group described above in R, and is preferably a methyl group or an ethyl group.

In the general formula (a1-1-02), R is as defined above.
The lower alkyl group for $R^{12}$ is the same as the lower alkyl group described above in R. $R^{12}$ is preferably a methyl group or an ethyl group, and most preferably an ethyl group. h is preferably 1 or 2, and most preferably 2.

As the structural unit (a1), one type can be used alone, or two or more different types can be used in combination.

In the component (A1), the amount of the structural unit (a1) is preferably 10 to 80 mol %, more preferably 20 to 70 mol %, and still more preferably 25 to 50 mol %, based on the combined total of all structural units constituting the component (A1). When this proportion is not less than the lower limit in the above range, then a pattern can be easily formed using a positive resist composition which includes the structural unit (a1), whereas when the proportion is not more than the upper limit in the above range, a good quantitative balance with the other structural units can be attained.

Structural Unit (a2)

Structural unit (a2) is a structural unit derived from an acrylate ester which has a lactone-containing cyclic group.

Here, the term "lactone-containing cyclic group" means a cyclic group containing a single ring (lactone ring) which has a "—O—C(O)—" structure. This lactone ring is counted as the first ring, and groups that contain only the lactone ring are referred to as monocyclic groups, whereas groups that also contain other ring structures are described as polycyclic groups regardless of the structure of the other rings.

In the case of using the component (A1) to form a resist film, the lactone-containing cyclic group of the structural unit (a2) is effective at improving the adhesion between the resist film and a substrate, and improving compatibility with the aqueous developing solution.

The structural unit (a2) can be used arbitrarily without any particular restriction.

Specific examples of the lactone-containing monocyclic group include a group in which one hydrogen atom is eliminated from γ-butyrolactone. Furthermore, specific examples of the lactone-containing polycyclic group include a group in which one hydrogen atom is eliminated from a bicycloalkane, a tricycloalkane, or a tetracycloalkane which contains a lactone ring.

Specific examples of the structural unit (a2) include structural units represented by the general formulae (a2-1) to (a2-5) shown below.

[Chemical Formula 34]

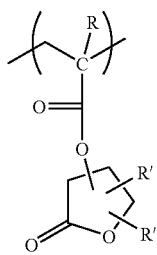
(a2-1)

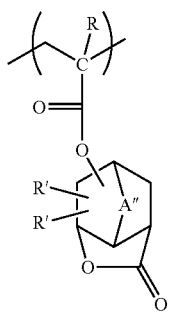
(a2-2)

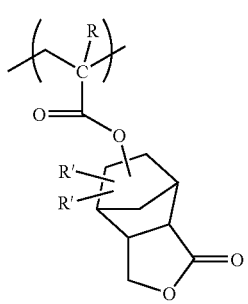
(a2-3)

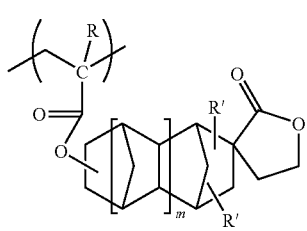
(a2-4)

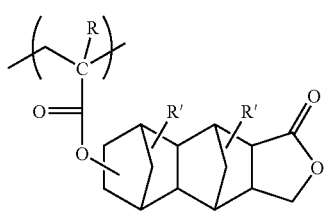
(a2-5)

(In the formula, R represents a hydrogen atom, a lower alkyl group, or a halogenated lower alkyl group; R' represents a hydrogen atom, a lower alkyl group, an alkoxy group of 1 to 5 carbon atoms, or a group of —COOR" (wherein R" represents a hydrogen atom, or a linear, branched, or cyclic alkyl group of 1 to 15 carbon atoms); m represents an integer of 0 or 1; A" represents an oxygen atom, a sulfur atom, or an alkylene group of 1 to 5 carbon atoms which may contain an oxygen atom or a sulfur atom.)

R in the general formula (a2-1) to (a2-5) is the same as R described above in the structural unit (a1).

As the lower alkyl group for R', the same lower alkyl groups as those for R described above in the structural unit (a1) can be mentioned.

In the case that R" is a linear or branched alkyl group, the number of carbon atoms is preferably 1 to 10, and more preferably 1 to 5.

In the case that R" is a cyclic alkyl group, the number of carbon atoms is preferably 3 to 15, more preferably 4 to 12, and most preferably 5 to 10. Specific examples of the cyclic alkyl group include groups in which one or more hydrogen atoms have been removed from a monocycloalkane or a polycycloalkane such as a bicycloalkane, tricycloalkane or tetracycloalkane, in which a fluorine atom or a fluorinated alkyl group may or may not be included as a substituent group. Specific examples thereof include groups in which one or more hydrogen atoms have been removed from a monocycloalkane such as cyclopentane and cyclohexane, and a polycycloalkane such as adamantane, norbornane, isobornane, tricyclodecane, and tetracyclododecane.

In the general formula (a2-1) to (a2-5), R' is preferably a hydrogen atom in terms of industrial availability.

As the alkylene group of 1 to 5 carbon atoms which may contain an oxygen atom or a sulfur atom, a methylene group, an ethylene group, an n-propylene group, an isopropylene group, —O—$CH_2$—, —$CH_2$—O—$CH_2$—, —S—$CH_2$—, and —$CH_2$—S—$CH_2$— can be mentioned.

Specific examples of the structural units represented by the general formulae (a2-1) to (a2-5) include the following.

[Chemical Formula 35]

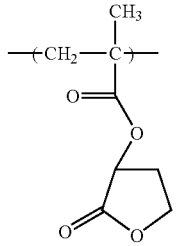
(a2-1-1)

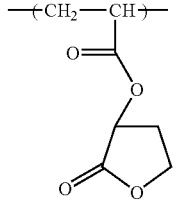
(a2-1-2)

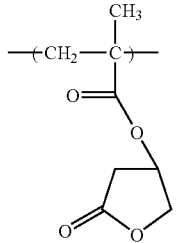
(a2-1-3)

(a2-1-4) 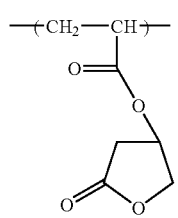
(a2-1-5) 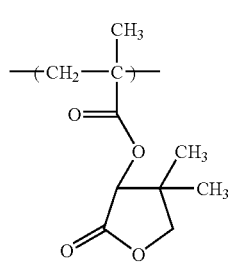
(a2-1-6) 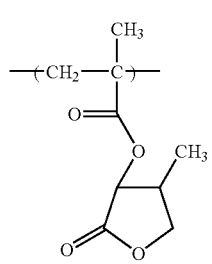
[Chemical Formula 36]
(a2-2-1) 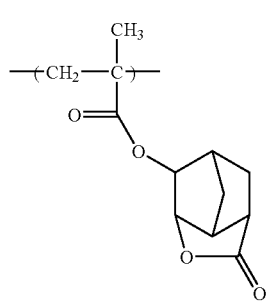
(a2-2-2) 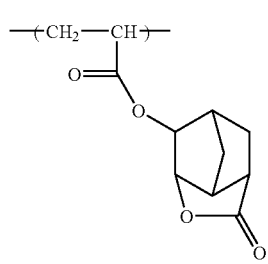
(a2-2-3) 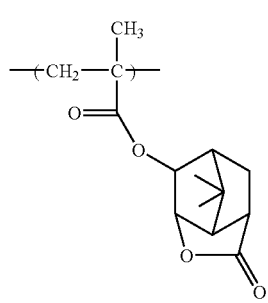
(a2-2-4) 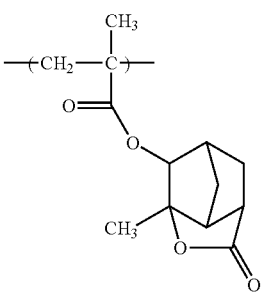
(a2-2-5) 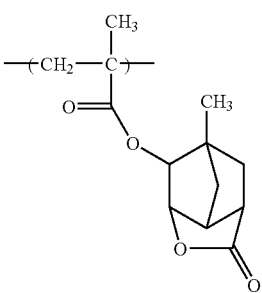
(a2-2-6) 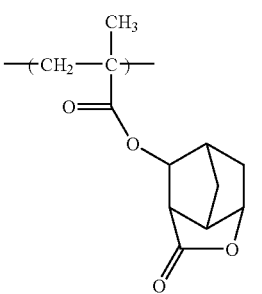
(a2-2-7) 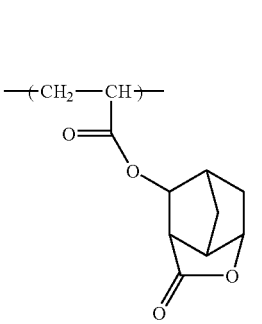
(a2-2-8) 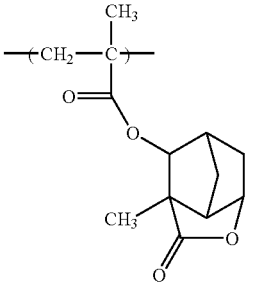

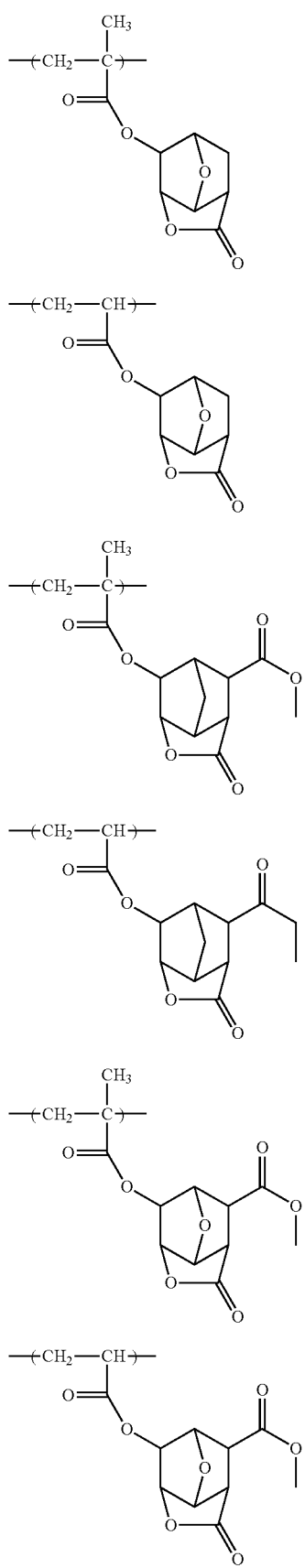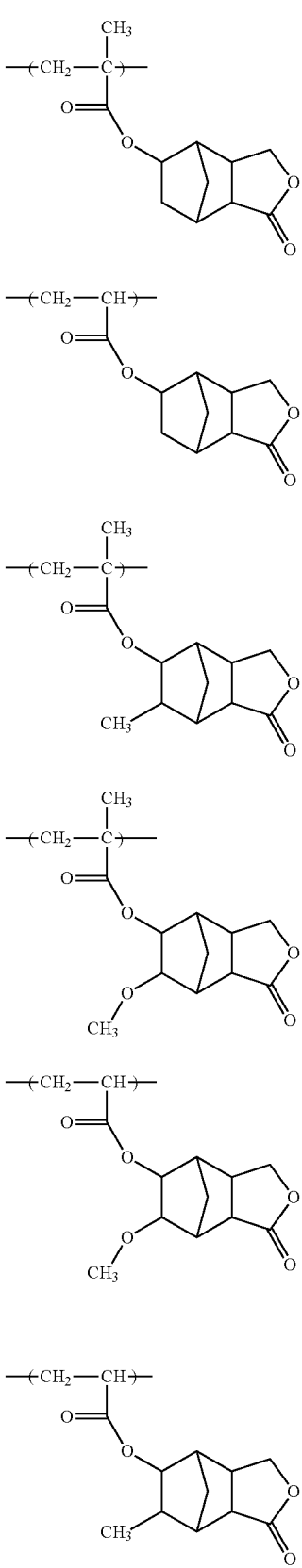

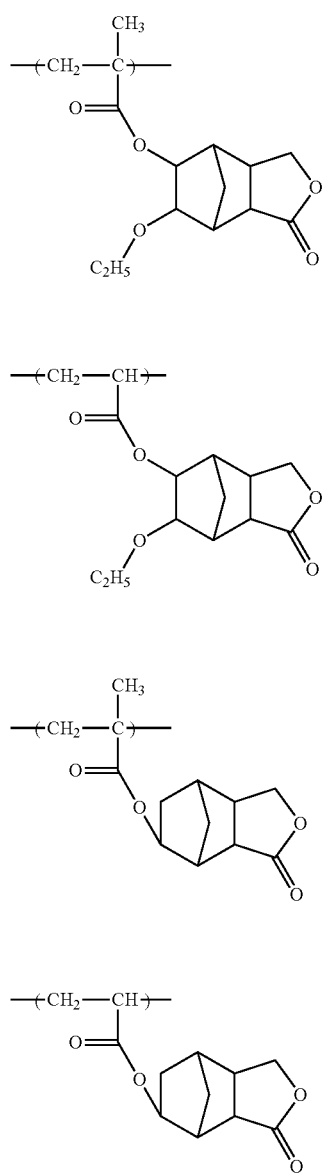
(a2-3-7)
(a2-3-8)
(a2-3-9)
(a2-3-10)
[Chemical Formula 38]
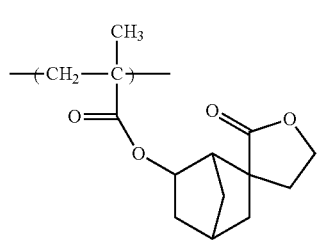
(a2-4-1)
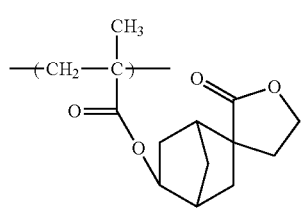
(a2-4-2)
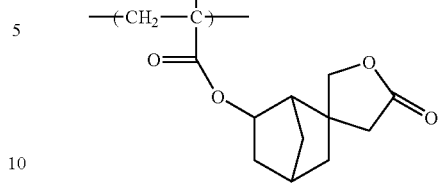
(a2-4-3)
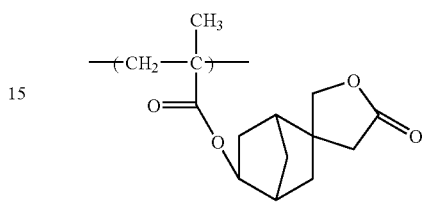
(a2-4-4)
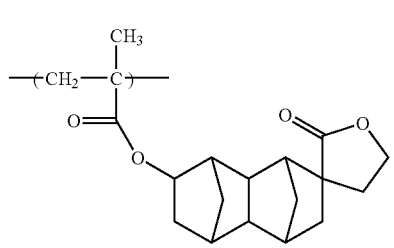
(a2-4-5)
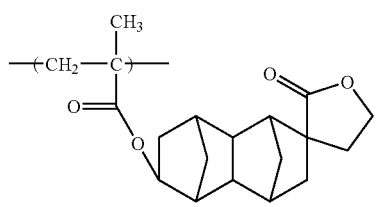
(a2-4-6)
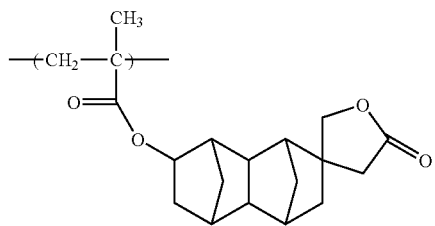
(a2-4-7)
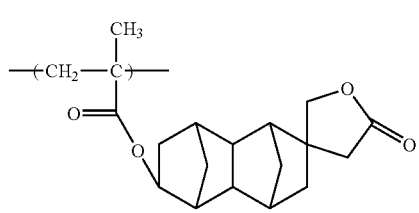
(a2-4-8)
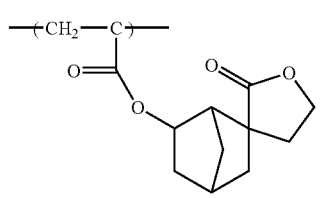
(a2-4-9)

-continued (a2-4-10)
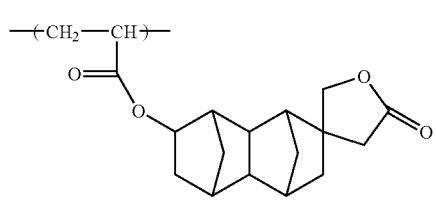

(a2-4-11)
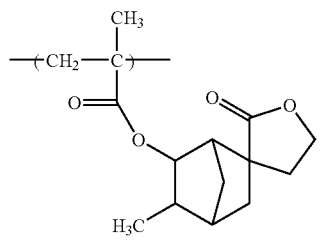

(a2-4-12)
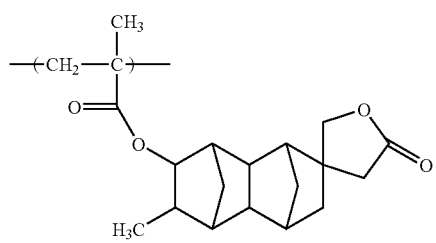

[Chemical Formula 39]

(a2-5-1)
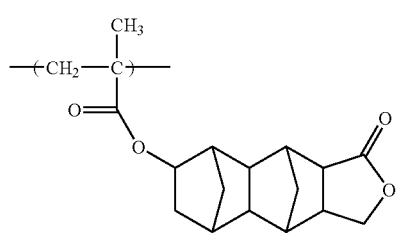

(a2-5-2)
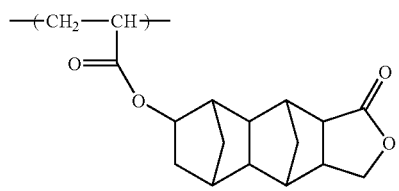

(a2-5-3)
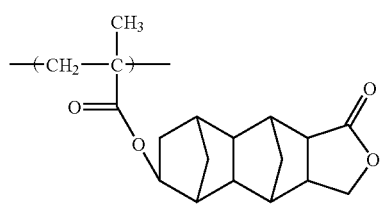

(a2-5-4)
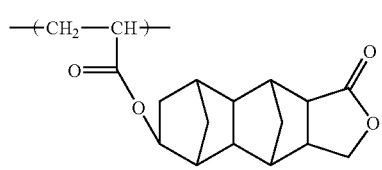

-continued (a2-5-5)
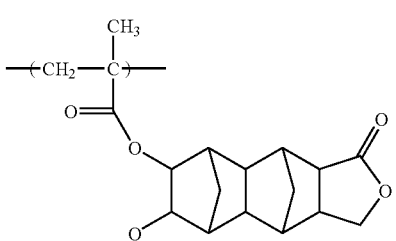

(a2-5-6)
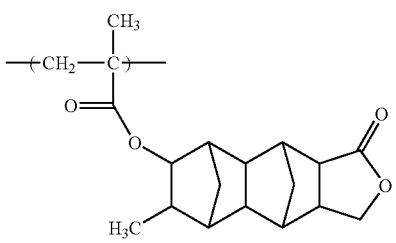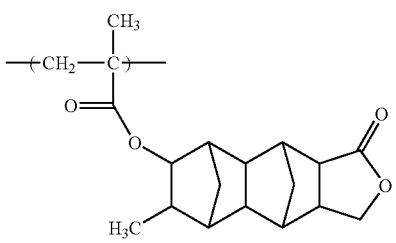

The structural unit (a2) is preferably at least one kind selected from the group consisting of the structural units represented by the general formulae (a2-1) to (a2-5), and more preferably at least one kind selected from the group consisting of the structural units represented by the general formulae (a2-1) to (a2-3). Of these, at least one kind selected from the group consisting of the structural units represented by the formulae (a2-1-1), (a2-1-2), (a2-2-1), (a2-2-2), (a2-2-9), (a2-2-10), (a2-3-1), (a2-3-2), (a2-3-9) and (a2-3-10) is particularly preferable.

As the structural unit (a2), one type can be used alone, or two or more different types can be used in combination.

In the component (A1), the amount of the structural unit (a2) is preferably 5 to 60 mol %, more preferably 10 to 50 mol %, and still more preferably 20 to 50 mol %, based on the combined total of all structural units constituting the component (A1). When this proportion is not less than the lower limit in the above range, then the effect made by containing the structural unit (a2) can be sufficiently obtained. When the proportion is not more than the upper limit in the above range, a good quantitative balance with the other structural units can be attained.

Structural Unit (a3)

Structural unit (a3) is a structural unit derived from an acrylate ester which has a polar group-containing aliphatic hydrocarbon group.

By including the structural unit (a3), the hydrophilicity of the component (A1) is improved, and hence, the compatibility of the component (A1) with the developing solution is improved. As a result, the solubility of the exposed portions in an alkali developing solution improves, which contributes to favorable improvements in the resolution.

Examples of the polar group include a hydroxyl group, a cyano group, a carboxyl group, and a hydroxyalkyl group in which a part of the hydrogen atoms in an alkyl group is substituted with fluorine atoms. Of these, a hydroxyl group is particularly preferable.

Examples of the aliphatic hydrocarbon group include a linear or branched hydrocarbon group (preferably an alkylene group) of 1 to 10 carbon atoms, and a polycyclic aliphatic hydrocarbon group (polycyclic group). The polycyclic group can be appropriately selected from the multitude of structural units proposed as resins in resist compositions for ArF excimer lasers and the like. The polycyclic group preferably has 7 to 30 carbon atoms.

Of these, a structural unit derived from an acrylate ester having the polycyclic aliphatic group which contains a hydroxyl group, cyano group, a carboxyl group, or a hydroxyalkyl group in which a part of the hydrogen atoms within an alkyl group has been substituted with fluorine atoms is more preferable. Examples of the polycyclic group include groups in which two or more hydrogen atoms have been removed from a bicycloalkane, a tricycloalkane, a tetracycloalkane, or the like. Specific examples include groups in which two or more hydrogen atoms have been removed from a polycycloalkane such as adamantane, norbornane, isobornane, tricyclodecane, or tetracyclododecane. Of these polycyclic groups, a group in which two or more hydrogen atoms have been removed from adamantane, norbornane, or tetracyclododecane is industrially preferable.

As the structural unit (a3), for example, a structural unit derived from a hydroxyethyl ester of acrylic acid is preferable, when the hydrocarbon group within the polar group-containing aliphatic hydrocarbon group is a linear or branched hydrocarbon group of 1 to 10 carbon atoms. On the other hand, a structural unit represented by a general formula (a3-1), (a3-2), or (a3-3) shown below is preferable, when the hydrocarbon group is a polycyclic group.

[Chemical Formula 40]

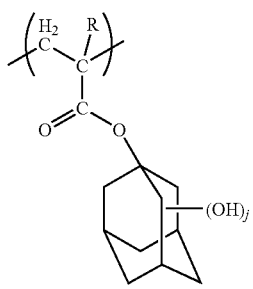
(a3-1)

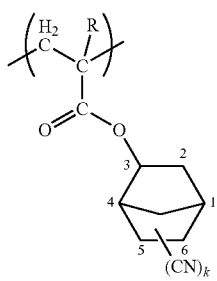
(a3-2)

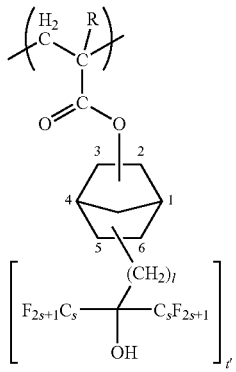
(a3-3)

(In the formulae, R is as defined above; j represents an integer of 1 to 3; k represents an integer of 1 to 3; t' represents an integer of 1 to 3; l represents an integer of 1 to 5; and s represents an integer of 1 to 3.)

In the general formula (a3-1), j is preferably 1 or 2, and more preferably 1. In the case that j is 2, a structural unit in which a hydroxyl group is bonded with the 3-position and 5-position of the adamantyl group is preferable. In the case that j is 1, a structural unit in which a hydroxyl group is bonded with the 3-position of the adamantyl group is preferable.

Of these, j is preferably 1, and a structural unit in which the hydroxyl group is bonded with the 3-position of adamantyl group is particularly preferable.

In the general formula (a3-2), k is preferably 1. In the general formula (a3-2), a cyano group is preferably bonded with the 5-position or 6-position of the norbornyl group.

In the general formula (a3-3), t' is preferably 1. l is preferably 1. s is preferably 1. Further, in the general formula (a3-3), it is preferable that a 2-norbonyl group or 3-norbonyl group be bonded at the terminal of the carboxy group of the acrylic acid. It is preferable that a fluorinated alkyl alcohol within brackets [ ] in the formula (a3-3) be bonded with the 5-position or 6-position of the norbornyl group.

As the structural unit (a3), one type can be used alone, or two or more different types can be used in combination.

In the component (A1), the amount of the structural unit (a3) is preferably 5 to 50 mol %, more preferably 5 to 40 mol %, and still more preferably 5 to 25 mol %, based on the combined total of all structural units constituting the component (A1). When this proportion is not less than the lower limit in the above range, then the effect made by containing the structural unit (a3) can be sufficiently obtained, whereas when the proportion is not more than the upper limit in the above range, good quantitative balance with the other components can be attained.

Structural Unit (a4)

The component (A1) may also have a structural unit (a4) which is different from the above-mentioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

The structural unit (a4) is preferably, for example, a structural unit derived from an acrylate ester containing a non-acid-dissociable aliphatic polycyclic group. Examples of the polycyclic group include the same polycyclic groups as those described above in the structural unit (a1), and any of the multitude of conventional polycyclic groups used within the resin component of resist compositions for ArF excimer lasers or KrF excimer lasers (and preferably for ArF excimer lasers) can be used.

In particular, at least one group selected from a tricyclodecanyl group, an adamantyl group, a tetracyclododecanyl group, an isobornyl group, and a norbornyl group are preferable in terms of industrial availability and the like. These polycyclic groups may contain a linear or branched alkyl group of 1 to 5 carbon atoms as a substituent group.

Specific examples of the structural unit (a4) include a structural unit represented by general formulae (a4-1) to (a4-5) shown below.

[Chemical Formula 41]

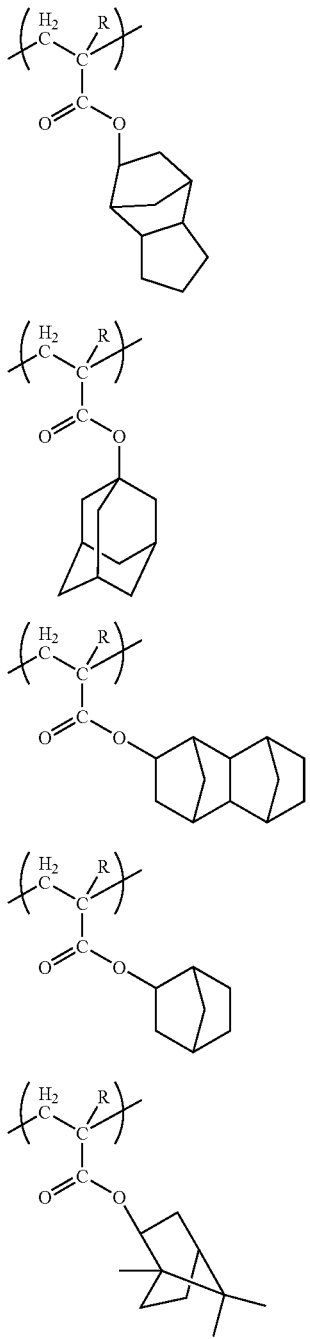

(a4-1)

(a4-2)

(a4-3)

(a4-4)

(a4-5)

(In the formula, R is as defined above.)

When the structural unit (a4) is included in the component (A1), the amount of the structural unit (a4) is preferably within the range from 1 to 30 mol %, and more preferably from 10 to 20 mol %, based on the combined total of all the structural units that constitute the component (A1).

In the present invention, the component (A1) preferably includes a copolymer which contains the structural units (a1), (a2) and (a3). Examples of the copolymer include a copolymer consisting of the structural units (a1), (a2) and (a3); and a copolymer consisting of the structural units (a1), (a2), (a3) and (a4).

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). When a hydroxyalkyl group in which a part of the hydrogen atoms of the alkyl group has been substituted with fluorine atoms is introduced into a copolymer in this manner, the copolymer thus obtained can have an advantageous effect of reducing the levels of developing defects and LER (line edge roughness: non-uniform irregularities within the line side walls).

The weight average molecular weight (Mw) (the polystyrene equivalent value determined by gel permeation chromatography) of the component (A1) is not particularly limited, and is preferably 2,000 to 50,000, more preferably 3,000 to 30,000, and most preferably 5,000 to 20,000. By ensuring that the weight average molecular weight of the polymer compound (A1) is no more than the upper limit, solubility sufficient for a resist relative to a resist solvent can be obtained. By ensuring that it is no less than the lower limit, excellent dry-etching resistance and excellent cross-sectional shape of the resist pattern can be obtained.

Further, the dispersity (Mw/Mn) is preferably within a range from 1.0 to 5.0, more preferably from 1.0 to 3.0, and most preferably from 1.2 to 2.5. Herein, Mn represents the number average molecular weight.

[Component (A2)]

It is preferable that the component (A2) has a molecular weight within a range of 500 to less than 2000, and contains an acid dissociable, dissolution inhibiting group exemplified above in the component (A1) and a hydrophilic group. Specific examples thereof include compounds wherein a portion of the hydrogen atoms of the hydroxyl groups within a compound containing a plurality of phenol structures have been substituted with an aforementioned acid dissociable, dissolution inhibiting group.

The component (A2) is preferably low molecular weight phenol compounds known as sensitizers or heat resistance improvement agents for non-chemically amplified g-line or i-line resists in which a part of hydrogen atoms of hydroxyl groups are substituted with the above acid dissociable, dissolution inhibiting group, and can be used arbitrarily selected from those.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3', 4'-trihydroxyphenyl)propane, tris(4-hydroxyphenyl) methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, and 1-[1-(4-hydroxyphenyl) isopropyl]-4-[1,1-bis(4-hydroxyphenyl)ethyl]benzene; and dimers, trimers and tetramers of formalin condensation products of phenols such as phenol, m-cresol, p-cresol and xylenol. Of course, the low molecular weight phenol compounds are not restricted to these examples.

There is no particular restriction on the acid dissociable, dissolution inhibiting group, and examples thereof include those described above.

As the component (A), one kind can be used alone, or two or more kinds can be used in combination.

In the resist composition of the present invention, the content of the component (A) may be adjusted according to the thickness of the resist film to be formed.

<Component (B)>

The component (B) includes an acid generator (B1) represented by the general formula (b1-1) (hereinafter, sometimes referred to as component (B1)). The component (B1) is the same as the compound (B1) in the present invention.

As the component (B1), one kind can be used alone, or two or more kinds can be used in combination.

In the resist composition of the present invention, the amount of the component (B1) in the component (B) is preferably not less than 40% by weight, more preferably not less than 70% by weight, and may be 100% by weight. The amount of the component (B1) is most preferably 100% by weight. When the amount is not less than the lower limit of the above range, the lithography properties such as resolution, mask reproducibility, and line width roughness (LWR) can be improved in the formation of the resist pattern using the resist composition of the present invention.

In the component (B), an acid generator (B2) (hereinafter, referred to as component (B2)) other than the component (B1) may be used in combination with the component (B1).

There is no particular restriction on the component (B2) as long as it is a component other than the component (B1), and those proposed as acid generators for chemically-amplified resists can be used as the component (B2).

Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzyl sulfonate-based acid generators; iminosulfonate-based acid generators; and disulfone-based acid generators.

As an onium salt-based acid generator, for example, an acid generator represented by a general formula (b-1) or (b-2) shown below can be used.

[Chemical Formula 42]

(In the formula, $R^{1\prime\prime}$ to $R^{3\prime\prime}$, $R^{5\prime\prime}$ and $R^{6\prime\prime}$ each independently represents an aryl group or an alkyl group; two of $R^{1\prime\prime}$ to $R^{3\prime\prime}$ may mutually be bonded to form a ring together with the sulfur atom; $R^{4\prime\prime}$ represents a linear, branched or cyclic alkyl group, or a linear, branched or cyclic fluorinated alkyl group; at least one of $R^{1\prime\prime}$ to $R^{3\prime\prime}$ represents an aryl group; and at least one of $R^{5\prime\prime}$ and $R^{6\prime\prime}$ represents an aryl group.)

In the general formula (b-1), $R^{1\prime\prime}$ to $R^{3\prime\prime}$ each independently represents an aryl group or an alkyl group. Here, two of $R^{1\prime\prime}$ to $R^{3\prime\prime}$ in the formula (b-1) may mutually be bonded to form a ring together with the sulfur atom.

Also, at least one of $R^{1\prime\prime}$ to $R^{3\prime\prime}$ represents an aryl group. Two or more of $R^{1\prime\prime}$ to $R^{3\prime\prime}$ are preferably aryl groups, and all of $R^{1\prime\prime}$ to $R^{3\prime\prime}$ are most preferably aryl groups.

There is no particular restriction on the aryl group for $R^{1\prime\prime}$ to $R^{3\prime\prime}$. For example, the aryl group may be an aryl group of 6 to 20 carbon atoms, and a part of or all of hydrogen atoms in the aryl group may be substituted with an alkyl group, an alkoxy group, a halogen atom, a hydroxyl group and the like, or may not be substituted. The aryl group is preferably an aryl group of 6 to 10 carbon atoms because it can be synthesized inexpensively. Specific examples thereof include a phenyl group and a naphthyl group.

In the aryl group, the alkyl group with which hydrogen atoms may be substituted is preferably an alkyl group of 1 to 5 carbon atoms, and most preferably a methyl group, an ethyl group, a propyl group, an n-butyl group, and a tert-butyl group.

In the aryl group, the alkoxy group with which hydrogen atoms may be substituted is preferably an alkoxy group of 1 to 5 carbon atoms, and most preferably a methoxy group, an ethoxy group, an n-propoxy group, an iso-propoxy group, an n-butoxy group, and a tert-butoxy group.

In the aryl group, the alkoxy group with which hydrogen atoms may be substituted is preferably an alkoxy group of 1 to 5 carbon atoms, and most preferably a methoxy group or an ethoxy group.

In the aryl group, the halogen atom with which hydrogen atoms may be substituted is preferably a fluorine atom.

There is no restriction on the alkyl groups for $R^{1\prime\prime}$ to $R^{3\prime\prime}$. Examples thereof include a linear, branched, or cyclic alkyl group of 1 to 10 carbon atoms. The number of carbon atoms is preferably 1 to 5, in terms of excellent resolution. Specific examples include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group. Of these, a methyl group is preferable, because it excels in resolution, and can be synthesized inexpensively.

Of these, it is most preferable that $R^{1\prime\prime}$ to $R^{3\prime\prime}$ each independently represents a phenyl group or a naphthyl group.

If two of $R^{1\prime\prime}$ to $R^{3\prime\prime}$ in the general formula (b-1) are mutually bonded to form a ring together with the sulfur atom, the ring including the sulfur atom preferably forms a 3- to 10-membered ring, and more preferably forms a 5- to 7-membered ring.

Also, if two of $R^{1\prime\prime}$ to $R^{3\prime\prime}$ in the general formula (b-1) are mutually bonded to form a ring together with the sulfur atom, the other of $R^{1\prime\prime}$ to $R^{3\prime\prime}$ is preferably an aryl group. As the aryl group, the same aryl groups as those described above in $R^{1\prime\prime}$ to $R^{3\prime\prime}$ can be mentioned.

$R^{4\prime\prime}$ represents a linear, branched or cyclic alkyl group, or a linear, branched or cyclic fluorinated alkyl group.

The number of carbon atoms in the linear or branched alkyl group for $R^{4\prime\prime}$ is preferably 1 to 10, more preferably 1 to 8, and most preferably 1 to 4.

The cyclic alkyl group for $R^{4\prime\prime}$ is the same as the cyclic group described above in $R^{1\prime\prime}$. The number of carbon atoms in the cyclic alkyl group of $R^{4\prime\prime}$ is preferably 4 to 15, more preferably 4 to 10, and most preferably 6 to 10.

The number of carbon atoms in the fluorinated alkyl group is preferably 1 to 10, more preferably 1 to 8, and most preferably 1 to 4.

Furthermore, the fluorination rate of the fluorinated alkyl group (proportion of fluorine atoms in the alkyl group) is preferably within a range of 10 to 100%, more preferably 50 to 100%, and those wherein all hydrogen atoms are substituted with fluorine atoms (perfluoroalkyl groups) are particularly preferable, because the strength of the acid increases.

$R^{4\prime\prime}$ is most preferably a linear or cyclic alkyl group, or a linear or cyclic fluorinated alkyl group.

In the general formula (b-2), $R^{5\prime\prime}$ and $R^{6\prime\prime}$ each independently represents an aryl group or an alkyl group. At least one of $R^{5\prime\prime}$ and $R^{6\prime\prime}$ represents an aryl group. Both of $R^{5\prime\prime}$ and $R^{6\prime\prime}$ preferably represent aryl groups.

As the aryl groups for $R^{5\prime\prime}$ and $R^{6\prime\prime}$, the same aryl groups as those described above in $R^{1\prime\prime}$ to $R^{3\prime\prime}$ can be mentioned.

As the alkyl groups for $R^{5\prime\prime}$ and $R^{6\prime\prime}$, the same alkyl groups as those described above in $R^{1\prime\prime}$ to $R^{3\prime\prime}$ can be mentioned.

Of these, it is most preferable that both of $R^{5\prime\prime}$ and $R^{6\prime\prime}$ be phenyl groups.

$R^{4\prime\prime}$ in the general formula (b-2) may be the same as those described in $R^{4\prime\prime}$ in the general formula (b-1) shown above.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

Also, onium salts whose anion moiety is substituted with a methansulfonate, an n-propanesulfonate, an n-butanesulfonate, or an n-octanesulfonate can be used.

Further, an onium salt-based acid generator in which the anion moiety in the general formula (b-1) or (b-2) is substituted with an anion moiety represented by a general formula (b-3) or (b-4) shown below can also be used. Here, the cation moiety is the same as those described in the general formula (b-1) or (b-2).

[Chemical Formula 43]

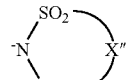

(b-3)

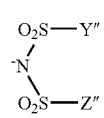

(b-4)

(In the formula, X" represents an alkylene group of 2 to 6 carbon atoms in which at least one hydrogen atom is substituted with a fluorine atom; and Y" and Z" each independently represents an alkyl group of 1 to 10 carbon atoms in which at least one hydrogen atom is substituted with a fluorine atom.)

X" represents a linear or branched alkylene group in which at least one hydrogen atom is substituted with a fluorine atom. The number of carbon atoms in the alkylene group for X" is 2 to 6, preferably 3 to 5, and most preferably 3.

Y" and Z" each independently represents a linear or branched alkyl group in which at least one hydrogen atom is substituted with a fluorine atom. The number of carbon atoms in the alkyl group for Y" and Z" is 1 to 10, preferably 1 to 7, and more preferably 1 to 3.

Lower numbers of carbon atoms within the alkylene group for X" or the alkyl groups for Y" and Z" result in better solubility within the resist solvent, and are consequently preferred.

Furthermore, in the alkylene group for X" or the alkyl groups for Y" and Z", higher numbers of hydrogen atoms that have been substituted with fluorine atoms results in increasing the strength of an acid and also improving the transparency relative to high energy light beams of 200 nm or less, or electron beams, and is consequently preferred. The proportion of fluorine atoms in the alkylene group or alkyl group, that is, the fluorination rate is preferably within a range of 70 to 100%, and more preferably 90 to 100%. A perfluoroalkylene group or a perfluoroalkyl group wherein all hydrogen atoms are substituted with fluorine atoms is most preferable.

Furthermore, a sulfonium salt that contains a cation moiety represented by a general formula (b-5') or (b-6') shown below can be used as an onium salt-based acid generator.

[Chemical Formula 44]

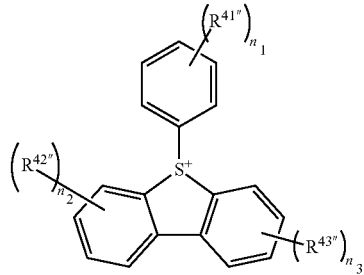

(b-5')

(b-6')

[Structure: a benzothiophene sulfonium cation with substituents $(R^{44''})_{n_4}$ on a phenyl ring attached to $S^+$, $(R^{45''})_{n_5}$ on the benzo ring, and $(R^{46''})_{n_6}$ on the thiophene ring]

(In the formula, $R^{41''}$ to $R^{46''}$ each independently represents an alkyl group, an acetyl group, an alkoxy group, a carboxyl group, a hydroxyl group or a hydroxyalkyl group; $n_1$ to $n_5$ each independently represents an integer of 0 to 3; and $n_6$ represents an integer of 0 to 2.)

The alkyl group for $R^{41''}$ to $R^{46''}$ is preferably an alkyl group of 1 to 5 carbon atoms. Of these, it is more preferably a linear or branched alkyl group, and still more preferably a methyl group, an ethyl group, a propyl group, an isopropyl group, an n-butyl group, or a tert-butyl group.

The alkoxy group for $R^{41}$ to $R^{46}$ is preferably an alkoxy group of 1 to 5 carbon atoms, more preferably a linear or branched alkoxy group, and particularly preferably a methoxy group or an ethoxy group.

The hydroxyalkyl group for $R^{41''}$ to $R^{46''}$ is preferably a group in which one or more hydrogen atoms in the alkyl group for $R^{41''}$ to $R^{46''}$ are substituted with hydroxyl groups, and examples thereof include a hydroxymethyl group, a hydroxyethyl group, and a hydroxypropyl group.

If there are two or more, as indicated by the corresponding value of $n_1$ to $n_6$, of an individual $R^{41''}$ to $R^{46''}$, group, then the two or more of the individual $R^{41''}$ to $R^{46''}$ group may be the same or different from each other.

$n_1$ is preferably 0 to 2, more preferably 0 or 1, and still more preferably 0.

It is preferable that $n_2$ and $n_3$ be each independently 0 or 1, and it is more preferable that they be 0.

$n_4$ is preferably 0 to 2, and more preferably 0 or 1.

$n_5$ is preferably 0 or 1, and more preferably 0.

$n_6$ is preferably 0 or 1, and more preferably 1.

There is no particular restriction on an anion moiety of a sulfonium salt that contains the cation moiety represented by the general formula (b-5') or (b-6'), and anion moieties of onium salt-based acid generators which have been proposed can be used as the anion moiety. Examples of the anion moiety include a fluorinated alkylsulfonate ion such as the anion moiety ($R^{4''}SO_3^-$) of the onium salt-based acid generator represented by the general formula (b-1) or (b-2); and an anion moiety represented by the general formula (b-3) or (b-4). Of these, a fluorinated alkylsulfonate ion is preferable, a fluorinated alkylsulfonate ion of 1 to 4 carbon atoms is more preferable, and a linear perfluoroalkylsulfonate ion of 1 to 4 carbon atoms is particularly preferable. Specific examples thereof include a trifluoromethylsulfonate ion, a heptafluoro-n-propylsulfonate ion, and a nonafluoro-n-butylsulfonate ion.

In the present specification, the term "oxime sulfonate-based acid generator" means a compound which has at least one of the groups represented by a general formula (B-1) shown below, and has a property that generates an acid upon exposure to radiation. These kinds of oxime sulfonate-based acid generators are widely used for a chemically-amplified resist composition, so any oxime sulfonate-based acid generator, arbitrarily selected from these, can be used.

[Chemical Formula 45]

$$-\underset{R^{32}}{\underset{|}{C}}=N-O-SO_2-R^{31} \quad (B-1)$$

(In the general formula (B-1), $R^{31}$ and $R^{32}$ each independently represents an organic group.)

The organic group for $R^{31}$ or $R^{32}$ is a group containing carbon atoms, and may further contain atoms other than carbon atoms (for example, a hydrogen atom, an oxygen atom, a nitrogen atom, a sulfur atom and a halogen atom (a fluorine atom, a chlorine atom and the like)).

The organic group for $R^{31}$ is preferably a linear, branched or cyclic alkyl group or an aryl group. The alkyl group or aryl group may contain a substituent group. There is no particular restriction on the substituent group, and examples thereof include a fluorine atom, and a linear, branched or cyclic alkyl group of 1 to 6 carbon atoms. Here, the term "containing a substituent group" means that a part or all of hydrogen atoms in the alkyl group or aryl group are substituted with substituent groups.

The number of carbon atoms in the alkyl group for $R^{31}$ is preferably 1 to 20, more preferably 1 to 10, still more preferably 1 to 8, still more preferably 1 to 6, and most preferably 1 to 4. The alkyl group for $R^{31}$ is particularly preferably an alkyl group which is partially or completely halogenated (hereinafter, sometimes referred to as a halogenated alkyl group). Here, a partially halogenated alkyl group means an alkyl group in which a part of the hydrogen atoms is substituted with halogen atoms, and a completely halogenated alkyl group means an alkyl group in which all of the hydrogen atoms are substituted with halogen atoms. Examples of the halogen atoms include a fluorine atom, a chlorine atom, a bromine atom and an iodine atom. Of these, a fluorine atom is preferable. That is, the halogenated alkyl group is preferably a fluorinated alkyl group.

The number of carbon atoms in the aryl group for $R^{31}$ is preferably 4 to 20, more preferably 4 to 10, and most preferably 6 to 10. The aryl group is particularly preferably an aryl group which is partially or completely halogenated. Here, a partially halogenated aryl group means an aryl group in which a part of the hydrogen atoms is substituted with halogen atoms, and a completely halogenated aryl group means an aryl group in which all of the hydrogen atoms are substituted with halogen atoms.

$R^{31}$ is particularly preferably an alkyl group of 1 to 4 carbon atoms containing no substituent group, or a fluorinated alkyl group of 1 to 4 carbon atoms.

The organic group for $R^{32}$ is preferably a linear, branched or cyclic alkyl group, an aryl group, or a cyano group. As the alkyl group or the aryl group for $R^{32}$, the same alkyl groups or aryl groups as those described above in $R^{31}$ can be mentioned.

$R^{32}$ is particularly preferably a cyano group, an alkyl group of 1 to 8 carbon atoms containing no substituent group, or a fluorinated alkyl group of 1 to 8 carbon atoms.

The oxime sulfonate-based acid generator is more preferably a compound represented by a general formula (B-2) or (B-3) shown below.

[Chemical Formula 46]

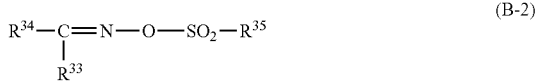

(B-2)

(In the general formula (B-2), $R^{33}$ represents a cyano group, an alkyl group containing no substituent group, or a halogenated alkyl group; $R^{34}$ represents an aryl group; and $R^{35}$ represents an alkyl group containing no substituent group, or a halogenated alkyl group.)

[Chemical Formula 47]

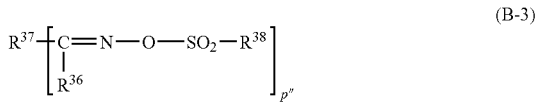

(B-3)

(In the general formula (B-3), $R^{36}$ represents a cyano group, an alkyl group containing no substituent group, or a halogenated alkyl group; $R^{37}$ represents a bivalent or trivalent aromatic hydrocarbon group; $R^{38}$ represents an alkyl group containing no substituent group, or a halogenated alkyl group; and p" represents an integer of 2 or 3.)

In the general formula (B-2), the number of carbon atoms in the alkyl group containing no substituent group or the halogenated alkyl group for $R^{33}$ is preferably 1 to 10, more preferably 1 to 8, and most preferably 1 to 6.

$R^{33}$ is preferably a halogenated alkyl group, and more preferably a fluorinated alkyl group.

The fluorinated alkyl group for $R^{33}$ is preferably a group in which 50% or more of the hydrogen atoms in the alkyl group are fluorinated, more preferably a group in which 70% or more of the hydrogen atoms in the alkyl group are fluorinated, and still more preferably a group in which 90% or more of the hydrogen atoms in the alkyl group are fluorinated.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group; and heteroaryl groups in which a part of the carbon atoms which constitute the rings of these groups are substituted with heteroatoms such as an oxygen atom, a sulfur atom, and a nitrogen atom. Of these, a fluorenyl group is preferable.

The aryl group for $R^{34}$ may contain a substituent group such as an alkyl group of 1 to 10 carbon atoms, a halogenated alkyl group of 1 to 10 carbon atoms, and an alkoxy group of 1 to 10 carbon atoms. The number of carbon atoms of the alkyl group or halogenated alkyl group in the substituent group is preferably 1 to 8, and more preferably 1 to 4. Also, the halogenated alkyl group is preferably a fluorinated alkyl group.

The number of carbon atoms in the alkyl group containing no substituent group or the halogenated alkyl group for $R^{35}$ is preferably 1 to 10, more preferably 1 to 8, and most preferably 1 to 6.

$R^{35}$ is preferably a halogenated alkyl group, and more preferably a fluorinated alkyl group.

The fluorinated alkyl group for $R^{35}$ is preferably a group in which 50% or more of the hydrogen atoms in the alkyl group are fluorinated, more preferably a group in which 70% or more of the hydrogen atoms in the alkyl group are fluorinated, and still more preferably a group in which 90% or more of the hydrogen atoms in the alkyl group are fluorinated, because the strength of the generated acid increases. The fluorinated alkyl group for $R^{35}$ is most preferably a completely fluorinated alkyl group in which 100% of the hydrogen atoms are substituted with fluorine atoms.

In the general formula (B-3), as the alkyl group containing no substituent group or the halogenated alkyl group for $R^{36}$, the same alkyl group containing no substituent group or halogenated alkyl group as those described above in $R^{33}$ can be mentioned.

Examples of the bivalent or trivalent aromatic hydrocarbon group for $R^{37}$ include aryl groups of $R^{34}$ in which one or two hydrogen atoms are further removed.

As the alkyl group containing no substituent group or the halogenated alkyl group for $R^{38}$, the same alkyl group containing no substituent group or halogenated alkyl group as those described above in $R^{35}$ can be mentioned.

p" is preferably 2.

Specific examples of the oxime sulfonate-based acid generator include α-(p-toluenesulfonyloxyimino)-benzylcyanide, α-(p-chlorobenzenesulfonyloxyimino)-benzylcyanide, α-(4-nitrobenzenesulfonyloxyimino)-benzylcyanide, α-(4-nitro-2-trifluoromethylbenzenesulfonyloxyimino)-benzylcyanide, α-(benzenesulfonyloxyimino)-4-chlorobenzylcyanide, α-(benzenesulfonyloxyimino)-2,4-dichlorobenzylcyanide, α-(benzenesulfonyloxyimino)-2,6-dichlorobenzylcyanide, α-(benzenesulfonyloxyimino)-4-methoxybenzylcyanide, α-(2-chlorobenzenesulfonyloxyimino)-4-methoxybenzylcyanide, α-(benzenesulfonyloxyimino)-thien-2-ylacetonitrile, α-(4-dodecylbenzenesulfonyloxyimino)-benzylcyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienylcyanide, α-(methylsulfonyloxyimino)-1-cyclopentenylacetonitrile, α-(methylsulfonyloxyimino)-1-cyclohexenylacetonitrile, α-(methylsulfonyloxyimino)-1-cycloheptenylacetonitrile, α-(methylsulfonyloxyimino)-1-cyclooctenylacetonitrile, α-(trifluoromethylsulfonyloxyimino)-1-cyclopentenylacetonitrile, α-(trifluoromethylsulfonyloxyimino)-cyclohexylacetonitrile, α-(ethylsulfonyloxyimino)-ethylacetonitrile, α-(propylsulfonyloxyimino)-propylacetonitrile, α-(cyclohexylsulfonyloxyimino)-cyclopentylacetonitrile, α-(cyclohexylsulfonyloxyimino)-cyclohexylacetonitrile, α-(cyclohexylsulfonyloxyimino)-1-cyclopentenylacetonitrile, α-(ethylsulfonyloxyimino)-1-cyclopentenylacetonitrile, α-(isopropylsulfonyloxyimino)-1-cyclopentenylacetonitrile, α-(n-butylsulfonyloxyimino)-1-cyclopentenylacetonitrile, α-(ethylsulfonyloxyimino)-1-cyclohexenylacetonitrile, α-(isopropylsulfonyloxyimino)-1-cyclohexenylacetonitrile, α-(n-butylsulfonyloxyimino)-1-cyclohexenylacetonitrile, α-(methylsulfonyloxyimino)-phenylacetonitrile, α-(methylsulfonyloxyimino)-p-methoxyphenylacetonitrile, α-(trifluoromethylsulfonyloxyimino)-phenylacetonitrile, α-(trifluoromethylsulfonyloxyimino)-p-methoxyphenylacetonitrile, α-(ethylsulfonyloxyimino)-p-methoxyphenylacetonitrile, α-(propylsulfonyloxyimino)-p-methylphenylacetonitrile, and α-(methylsulfonyloxyimino)-p-bromophenylacetonitrile.

Also, oxime sulfonate-based acid generators disclosed in Japanese Unexamined Patent Application, First Publication No. Hei9-208554 ([Formula 18] and [Formula 19] in paragraphs [0012] to [0014]), and International Publication WO 2004/074242 (Examples 1 to 40 on pages 65 to 85) can be preferably used.

Further, suitable examples thereof include the following.

[Chemical Formula 48]

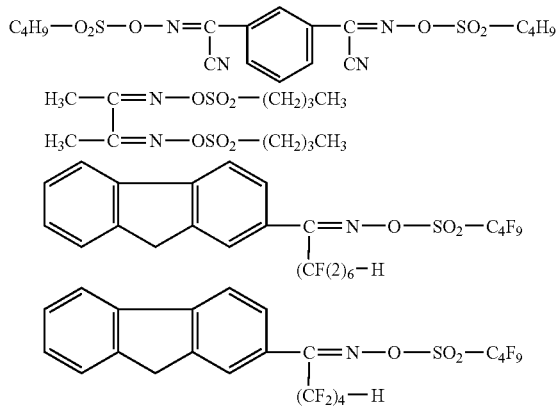

Among the diazomethane-based acid generators, specific examples of bisalkyl- or bisarylsulfonyldiazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2, 4-dimethylphenylsulfonyl)diazomethane.

Also, diazomethane-based acid generators disclosed in Japanese Unexamined Patent Application, First Publication No. Hei11-035551, Japanese Unexamined Patent Application, First Publication No. Hei11-035552, and Japanese Unexamined Patent Application, First Publication No. Hei11-035573 can be preferably used.

Examples of the poly(bissulfonyl)diazomethanes include 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, which are disclosed in Japanese Unexamined Patent Application, First Publication No. Hei11-322707.

As the component (B2), one kind selected from the above acid generators may be used alone, or two or more kinds may be used in combination.

The amount of the component (B) in the resist composition of the present invention is preferably within a range of 0.5 to 30 parts by mass, and more preferably 1 to 20 parts by mass, relative to 100 parts by mass of the component (A). When the amount is within the range, a pattern can be sufficiently formed. Also, a uniform solution and excellent storage stability can be obtained. Therefore, an amount within the above range is preferable.

<Component (D)>

In order to improve the resist pattern shape and the post exposure stability of the latent image formed by the pattern-wise exposure of the resist layer, the resist composition of the present invention preferably further includes a nitrogen-containing organic compound (D) (hereinafter, referred to as component (D)).

Since a multitude of these components (D) have already been proposed, any of these known compounds can be arbitrarily used. Of these, an aliphatic amine, particularly a secondary aliphatic amine or tertiary aliphatic amine is preferred. An aliphatic amine is an amine having one or more aliphatic groups, and the aliphatic groups preferably have 1 to 12 carbon atoms.

Examples of the aliphatic amine include an amine (alkylamine or alkylalcoholamine) wherein at least one of the hydrogen atoms of NH3 is substituted with an alkyl or hydroxyalkyl group having 12 or less carbon atoms; and a cyclic amine.

Specific examples of the alkylamines or alkylalcoholamines include monoalkylamines such as n-hexylamine, n-heptylamine, n-octylamine, n-nonylamine, or n-decylamine; dialkylamines such as diethylamine, di-n-propylamine, di-n-heptylamine, di-n-octylamine, or dicyclohexylamine; trialkylamines such as trimethylamine, triethylamine, tri-n-propylamine, tri-n-butylamine, tri-n-pentylamine, tri-n-hexylamine, tri-n-heptylamine, tri-n-octylamine, tri-n-nonylamine, tri-n-decanylamine, or tri-n-dodecylamine; and alkylalcoholamines such as diethanolamine, triethanolamine, diisopropanolamine, triisopropanolamine, di-n-octanolamine, or tri-n-octanolamine. Among these amines, trialkylamines in which three alkyl groups of 5 to 10 carbon atoms are bonded with a nitrogen atom are preferable, and tri-n-pentylamine is most preferable.

Examples of the cyclic amine include a heterocyclic compound containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amines include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

These may be used either alone, or in combination of two or more different compounds.

The component (D) is typically used in a quantity within a range of 0.01 to 5.0 parts by weight, relative to 100 parts by weight of the component (A).

<Optional Components>

[Component (E)]

In the positive resist composition of the present invention, in order to prevent any deterioration in sensitivity, and improve the resist pattern shape and the post exposure stability of the latent image formed by the pattern-wise exposure of the resist layer, at least one compound (E) selected from the group consisting of organic carboxylic acids and phosphorus oxo acids or derivatives thereof (hereinafter, referred to as component (E)) can also be added as an optional component.

Suitable examples of organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly preferable.

Examples of phosphorus oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphate esters such as di-n-butyl phosphate and diphenyl phosphate.

Examples of phosphonic acid derivatives include phosphonate esters such as dimethyl phosphonate, di-n-butyl phosphonate, phenylphosphonic acid, diphenyl phosphonate and dibenzyl phosphonate.

Examples of phosphinic acid derivatives include phosphinic esters such as phenylphosphinic acid.

As the component (E), one type may be used alone, or two or more types may be used in combination.

As the component (E), an organic carboxylic acid is preferable, and salicylic acid is particularly preferable.

The component (E) is used in a quantity within a range of 0.01 to 5.0 parts by weight, relative to 100 parts by weight of the component (A).

In the positive resist composition of the present invention, if desired, additives having miscibility, for example, additive resins for improving performance of a resist film, surfactants for improving coatability, dissolution inhibitors, plasticizers, stabilizers, colorants, antihalation agents, and dyes can be appropriately added.

[Organic Solvent (S)]

The resist composition of the present invention can be prepared by dissolving materials in an organic solvent (S) (hereinafter, sometimes referred to as component (S)).

The component (S) may be an organic solvent which can dissolve the respective components used in the present invention to give a uniform solution, and one or more kinds of organic solvents can be used, appropriately selected from those which have been conventionally known as a solvent for a chemically-amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols such as ethylene glycol, diethylene glycol, propylene glycol, dipropylene glycol; derivatives of the polyhydric alcohols, including compounds having ester bonds such as ethylene glycol monoacetate, diethylene glycol monoacetate, propylene glycol monoacetate and dipropylene glycol monoacetate, and compounds having ether bonds such as monoalkyl ethers (for example, monomethyl ether, monoethyl ether, monopropyl ether and monobutyl ether) and monophenyl ether of the above polyhydric alcohols or the above compounds having ester bonds (of these, propylene glycol monomethyl ether acetate (PGMEA) or propylene glycol monomethyl ether (PGME) is preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, ethyl ethoxypropionate; and aromatic organic solvents such as anisole, ethylbenzyl ether, cresylmethyl ether, diphenyl ether, dibenzyl ether, phenetole, butylphenyl ether, ethylbenzene, diethylbenzene, pentylbenzene, isopropylbenzene, toluene, xylene, cymene, and mesitylene.

These organic solvents may be used either alone, or as a mixed solvent of two or more different solvents.

Of these, propylene glycol monomethyl ether acetate (PGMEA), propylene glycol monomethyl ether (PGME) or EL is preferable.

Also, a mixed solvent obtained by mixing PGMEA and a polar solvent is preferable. The mixing ratio (mass ratio) of PGMEA to the polar solvent may be appropriately decided taking account of compatibility, and is preferably adjusted within a range of 1:9 to 9:1, and more preferably 2:8 to 8:2.

More specifically, in the case of using EL as the polar solvent, the mass ratio PGMEA:EL is preferably within a range of 1:9 to 9:1, and more preferably 2:8 to 8:2. Furthermore, in those cases of using PGME as the polar solvent, the mass ratio PGMEA:PGME is preferably within a range of 1:9 to 9:1, more preferably 2:8 to 8:2, and still more preferably 3:7 to 7:3.

Furthermore, as the component (S), mixed solvents of at least one of PGMEA and EL with γ-butyrolactone are also preferred. In such cases, the mass ratio of the former and latter components in the mixed solvents is preferably within a range of 70:30 to 95:5.

There is no particular restriction on the quantity of the component (S), and the quantity should be set in accordance with the required coating film thickness within a concentration that enables favorable application of the solution to a substrate or the like. Typically, the quantity is set so that the solid fraction concentration within the resist composition falls within a range of 2 to 20% by weight, and still more preferably 5 to 15% by weight.

<<Method of Forming Resist Pattern>>

The method of forming a resist pattern according to the fifth aspect of the present invention includes: forming a resist film on a substrate using a resist composition according to the fourth aspect of the present invention; exposing the resist film; and developing the resist film with alkali to form a resist pattern.

The method of forming a resist pattern of the present invention can be performed, for example, in the following manner.

Namely, the resist composition described above is first applied to a substrate using a spinner or the like, a prebake (post apply bake (PAB)) is then conducted under temperature conditions of 80 to 150° C. for 40 to 120 seconds, preferably for 60 to 90 seconds, followed by selective exposure of the thus obtained film with an ArF exposure apparatus or the like, by irradiating ArF excimer laser light through a desired mask pattern, and then PEB (post exposure baking) is conducted under temperature conditions of 80 to 150° C. for 40 to 120 seconds, preferably for 60 to 90 seconds. Subsequently, a developing treatment is conducted using an alkali developing solution such as 0.1 to 10% by weight aqueous solution of tetramethylammonium hydroxide, and a water rinse treatment is preferably conducted using pure water, and then a drying treatment is performed. Also, according to circumstances, a bake treatment (post bake) may be conducted after the above developing treatment. In this manner, a resist pattern that is faithful to the mask pattern can be obtained.

The substrate is not specifically limited and a conventionally known substrate can be used. For example, substrates for electronic components, and such substrates having prescribed wiring patterns formed thereon can be mentioned. Specific examples thereof include a silicon wafer; a substrate made of a metal such as copper, chromium, iron and aluminum; and a substrate made of glass. As materials for the wiring pattern, for example, copper, aluminum, nickel and gold can be used.

Further, as the substrate, any one of the above-mentioned substrates provided with an inorganic and/or organic film on the surface thereof may be used. As the inorganic film, an inorganic anti-reflection film (inorganic BARC) can be mentioned. As the organic film, an organic anti-reflection film (organic BARC) can be mentioned.

There is no particular restriction on the wavelength used for the exposure, and the exposure can be conducted using radiation such as ArF excimer lasers, KrF excimer lasers, $F_2$ excimer lasers, extreme ultraviolet rays (EUV), vacuum ultraviolet rays (VUV), electron beams (EB), X-rays, and soft X-rays. The resist composition is effective for KrF excimer lasers, ArF excimer lasers, EB or EUV, and particularly effective for ArF excimer lasers.

The exposure of the resist film may be a usual exposure conducted in an air or an inactive gas such as a nitrogen gas (dry exposure), or may be an immersion exposure (liquid immersion lithography).

As described above, the immersion exposure is conventionally conducted under the condition where the region between a lens and a resist film on a wafer is filled with a solvent (immersion solvent) that has a larger refractive index than the refractive index of air.

More specifically, the immersion exposure is performed in the following manner. First, the region between the resist film obtained in the above manner and the lens at the lowermost point of the exposure apparatus is pre-filled with a solvent (immersion solvent) that has a larger refractive index than the refractive index of air, and then, while maintaining such a condition, the exposure (immersion exposure) is conducted through the desired mask pattern.

The immersion solvent is preferably a solvent that has a refractive index larger than the refractive index of air but smaller than the refractive index of the resist film exposed by the immersion exposure. There is no restriction on the refractive index of the immersion solvent, as long as the solvent has a refractive index within the above range.

Examples of the solvent which has a refractive index larger than that of air but smaller than that of a resist film include water, fluorine-based inactive liquid, a silicon-based solvent, and a hydrocarbon-based solvent.

Specific examples of the fluorine-based inactive liquid include a liquid which has a fluorine-based compound as a main component, such as $C_3HCl_2F_5$, $C_4F_9OCH_3$, $C_4F_9OC_2H_5$, and $C_5H_3F_7$. The fluorine-based inactive liquid preferably has a boiling point within a range of 70 to 180° C., and more preferably 80 to 160° C. If the fluorine-based inactive liquid has a boiling point within the above range, the solvent used for the immersion exposure can be removed by a convenient method after exposure, and consequently it is preferable.

The fluorine-based inactive liquid is particularly preferably a perfluoroalkyl compound in which all hydrogen atoms of the alkyl groups are substituted with fluorine atoms. Examples of these perfluoroalkyl compounds include perfluoroalkylether compounds and perfluoroalkylamine compounds.

Specific examples of the perfluoroalkylether compounds include a perfluoro(2-butyl-tetrahydrofuran) (boiling point: 102° C.), and specific examples of the perfluoroalkylamine compounds include a perfluorotributylamine (boiling point: 174° C.).

The resist composition of the present invention is a novel resist composition which has not been known conventionally.

Also, according to the resist composition of the present invention, a resist pattern can be formed with excellent lithography properties such as the improvement of the mask reproduction (for example, the mask linearity), the collapse margin, and the resist pattern shape in the formation of the resist pattern. Although the reason is not clear, it can be speculated about as follows.

In the resist composition of the present invention, the component (B1) is used as the acid generator.

The anion moiety of the abovementioned component (B1) has a structure in which an aromatic cyclic group of 5 to 30 carbon atoms which contains a fluorine atom is bonded with the skeleton of "$Y^1$—$SO_3$—" through a group of "—$Q^1$—"".

Therefore, when compared with a fluorinated alkylsulfonate ion which has conventionally been used as an anion, the anion moiety of the present invention has high polarity and a sterically-bulky structure. It is speculated that, since the anion moiety of the present invention has the intermolecular interaction caused by high polarity and has the sterically-bulky structure, the diffusion of the anion moiety in the resist film can chemically and physically be suppressed when compared with an anion moiety of conventional acid generators such as nonafluorobutane sulfonate. Therefore, it is speculated that the diffusion of the acid generated in the exposed region toward the non-exposed region can be suppressed by using the component (B1), and consequently, the difference (solubility contrast) of the solubility in an alkali between non-exposed region and exposed region can be increased, thereby improving the resolution and the resist pattern shape.

For the same reasons, it is also expected that the exposure margin (EL margin) can be improved. The EL margin is the range of the exposure dose at which a resist pattern can be formed with a size which enables the variation for the target size to be kept within a prescribed range, when the exposure is performed changing the exposure dose. That is, the EL margin is the range of the exposure dose at which a resist pattern faithful to the mask pattern can be obtained. The larger the value of the EL margin, the smaller the variation of the pattern size depending on the change in the exposure dose becomes, and the more the process margin can be improved. Consequently, a larger value of the EL margin is preferable.

Also, the alkyl chain of the alkylene group which may contain a substituent group, or fluorinated alkylene group which may contain a substituent group for $Y^1$ has an excellent degradation property when compared with a perfluoroalkyl chain of 6 to 10 carbon atoms which is persistent (hardly-degradable), and thus it can be handled more safely in terms of the bioaccumulation potential.

EXAMPLES

Next, the present invention will be described in more detail with reference to examples, but the scope of the present invention is not limited to the following examples.

Example 1

(i) 192.1 g of methyl fluorosulfonyl(difluoro)acetate and 480 g of pure water were maintained at 10° C. or lower in an ice bath, and 440 g of 30% by weight aqueous solution of sodium hydroxide was dropwise added thereto. Then, the resultant was refluxed at 100° C. for 3 hours, followed by cooling and neutralizing with 10% by weight hydrochloric acid. The resulting solution was dropwise added to 9,074 g of acetone, and the precipitate was collected by filtration and dried, thereby obtaining 257.6 g of compound (1) shown below in the form of a white solid (purity: 80.7%, yield: 94.5%)

[Chemical Formula 49]

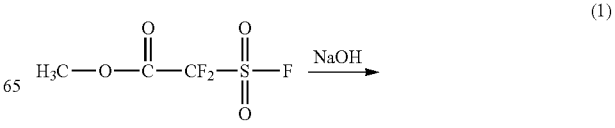

(1)

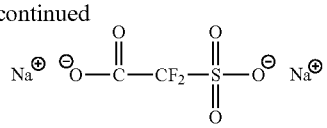

(ii) 56.2 g of compound (1) and 562.2 g of acetonitrile were prepared, and 77.4 g of p-toluenesulfonic acid hydrate was added thereto. The resultant was refluxed at 110° C. for 3 hours. Then, the reaction solution was filtered, and the filtrate was concentrated and dried to obtain a solid. 900 g of t-butyl methyl ether (TBME) was added to the obtained solid and stirred. Thereafter, the resultant was filtered, and the residue was dried, thereby obtaining 25.7 g of a compound (2) shown below in the form of a white solid (purity: 91.0%, yield: 52.0%).

[Chemical Formula 50]

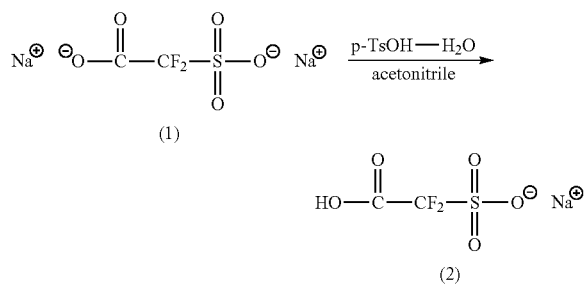

(iii) 5.00 g of the compound (2) (purity: 91.0%), 10.48 g of pentafluorophenoxyethanol (3) shown below, and 50.00 g of toluene were prepared, and 0.935 g of p-toluenesulfonic acid hydrate was added thereto. The resultant was refluxed at 110° C. for 15 hours. Then, the steps of filtering the reaction solution, adding 46.87 g of toluene to the residue, stirring the resulting solution at room temperature for 15 minutes, and filtering the solution were repeated twice, thereby obtaining a white powder. The white powder was dried under diminished pressure overnight. The next day, 46.87 g of acetonitrile was added to the white powder, and the solution was stirred at room temperature for 15 minutes, and then filtered. The filtrate obtained was dropwide added to 468.7 g of TBME, and the precipitated solid was collected by filtration and dried, thereby obtaining 6.69 g of a compound (4) shown below in the form of a white powder (purity: 99.5%, yield: 71.0%).

[Chemical Formula 51]

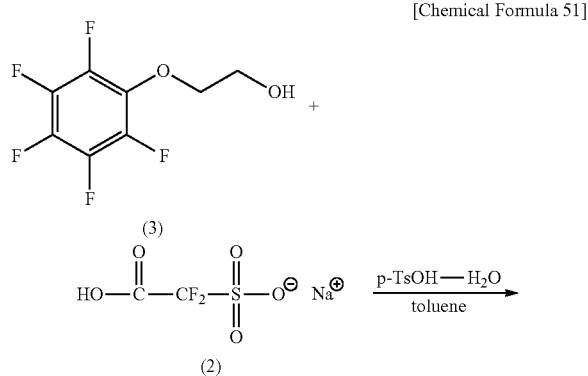

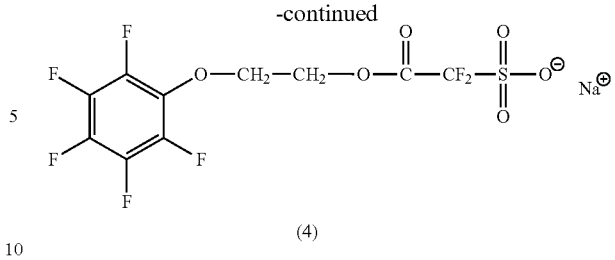

(4)

The compound (4) was analyzed by $^1$H-NMR and $^{19}$F-NMR.

$^1$H—NMR (DMSO-d6, 400 MHz): δ(ppm)=4.4-4.5 (t, 4H,Ha, Hb)

$^{19}$F—NMR (DMSO-d6, 400 MHz): δ (ppm)=−106.7 (s, 2F, Fa), −154.0 (s, 2F, Fb), −160.0 to −161.5 (s, 3F, Fc) (here, the peak of hexafluorobenzene was regarded as −160 ppm.)

From the results described above, it could be confirmed that the compound (4) had a structure shown below.

[Chemical Formula 52]

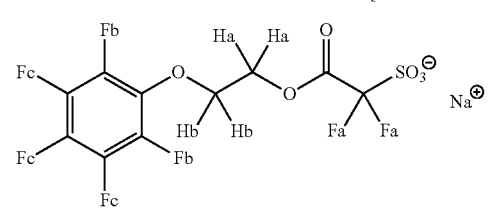

Example 2

(iv) 0.726 g of the compound (4) was dissolved in 5.30 g of pure water, and then 0.53 g of triphenylsulfoniumbromide (TPS-Br) was added thereto. The solution was stirred at room temperature for 1 hour. Thereafter, 5.30 g of methylene chloride was added thereto, and the organic layer was collected by fractionation. The organic layer was washed three times with 1% by weight aqueous solution of HCl, washed four times with pure water, and then concentrated, thereby obtaining 0.84 g of a compound (5) shown below in the form of a transparent and colorless viscous liquid (purity: 98.2%, yield: 85.7%).

[Chemical Formula 53]

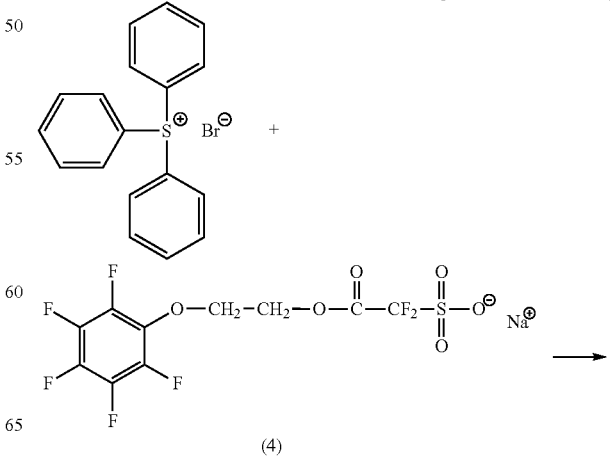

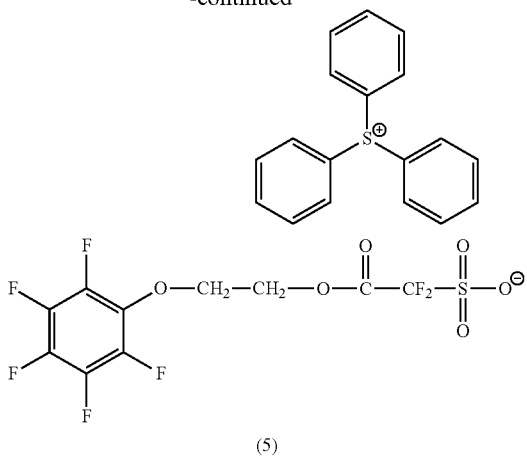

(5)

The compound (5) was analyzed by $^1$H-NMR and $^{19}$F-NMR.

$^1$H—NMR (DMSO-d6, 400 MHz): δ(ppm)=4.4-4.5 (t, 4H, Ha, Hb), 7.7-7.9 (m, 15H, Hc)

$^{19}$F—NMR (DMSO-d6, 400 MHz): δ(ppm)=−106.7 (s, 2F, Fa), −154.0 (s, 2F, Fb), −160.0 to −161.5 (s, 3F, Fc) (herein, the peak of hexafluorobenzene was regarded as −160 ppm).

From the results described above, it could be confirmed that the compound (5) had a structure shown below.

[Chemical Formula 54]

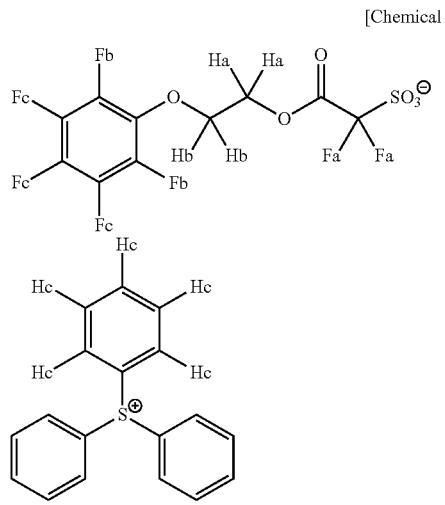

Comparative Example 1

(v) 5.00 g of the compound (2) (purity: 91.0%), 6.35 g of phenoxyethanol (6) shown below, and 50.00 g of toluene were prepared, and 0.935 g of p-toluenesulfonic acid hydrate was added thereto. The solution was refluxed at 110° C. for 15 hours. Then, the steps of filtering the reaction solution, adding 46.87 g of toluene to the residue, stirring the solution obtained at room temperature for 15 minutes, and filtering the solution were repeated twice, thereby obtaining a white powder. The white powder was dried under diminished pressure overnight. The next day, 46.87 g of acetonitrile was added to the white powder, and the solution was stirred at room temperature for 15 minutes, and then filtered. The filtrate obtained was dropwide added to 468.7 g of TBME, and the precipitated solid was collected by filtration and dried, thereby obtaining 5.87 g of a compound (7) shown below in the form of a white solid (purity: 98.1%, yield: 78.8%).

[Chemical Formula 55]

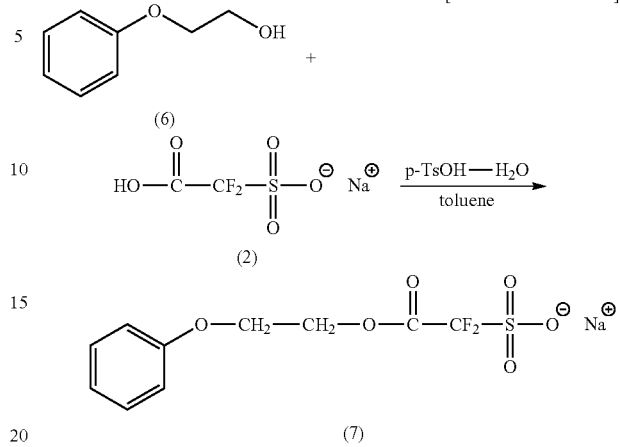

(vi) 1.00 g of the compound (7) was dissolved in 9.00 g of pure water, and 0.890 g of TPS-Br was added thereto. The solution was stirred at room temperature for 1 hour. Thereafter, 9.00 g of methylene chloride was added thereto, and the organic layer was collected by fractionation. The organic layer was washed three times with 1% by weight aqueous solution of HCl, washed four times with pure water, and then concentrated, thereby obtaining 1.28 g of a compound (8) shown below in the form of a transparent and colorless viscous liquid (purity: 98.9%, yield: 90.1%).

[Chemical Formula 56]

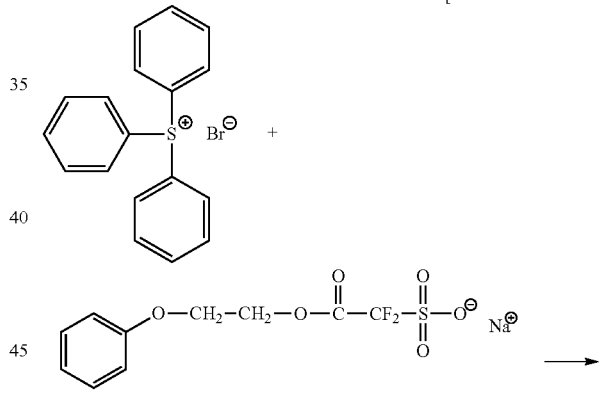

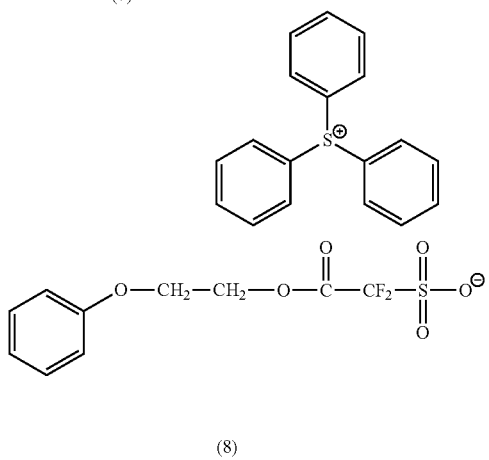

(8)

[Evaluation of Solubility of Acid Generator Component in Resist Solvent]

The solubility of the compounds (B)-1 to (B)-3 (acid generators) in a resist solvent was evaluated by the following procedure.

(B)-1: the above compound (5)
(B)-2: (4-methylphenyl)diphenylsulfonium nonafluoro-n-butanesulfonate
(B)-3: the above compound (8)

As the resist solvent, PGMEA, PGME, or EL was used.

Each of the compounds (B)-1 to (B)-3 was little by little added to 100 g of PGMEA, PGME, or EL (controlled at 23° C.), and the solubility of the acid generator components was evaluated. The results are shown in Table 1.

The values shown in Table 1 represents the amount of each of the compound (B)-1 to (B)-3 which was completely dissolved in each resist solvent. The term ">20" means that 20 g or more of a compound shown in Table 1 was completely dissolved in a resist solvent, and the term "1>" means that 1 g of a compound shown in Table 1 was not completely dissolved in a resist solvent.

TABLE 1

| Resist solvent | (B)-1 Mw: 599 | (B)-2 Mw: 577 | (B)-3 Mw: 509 |
|---|---|---|---|
| PGMEA | >20 | >20 | 1> |
| PGME | >20 | >20 | 1-3 |
| EL | >20 | >20 | 15-20 |

From the results shown above, it can be confirmed that the compound (B)-1 exhibits excellent solubility in each resist solvent at the same level as the compound (B)-2, and more excellent solubility in each resist solvent as compared with the compound (B)-3.

Example 3, Comparative Examples 2 and 3

As shown in Table 2, each component was mixed, and dissolved, thereby preparing a positive resist composition.

TABLE 2

|  | Component (A) | Component (B) | Component (D) | Component (E) | Component (S) | |
|---|---|---|---|---|---|---|
| Example 3 | (A)-1 [100] | (B)-1 [8.31] | (D)-1 [1.20] | (E)-1 [1.32] | (S)-1 [2000] | (S)-2 [10] |
| Comparative Example 2 | (A)-1 [100] | (B)-2 [8.00] | (D)-1 [1.20] | (E)-1 [1.32] | (S)-1 [2000] | (S)-2 [10] |
| Comparative Example 3 | (A)-1 [100] | (B)-3 [7.06] | (D)-1 [1.20] | (E)-1 [1.32] | (S)-1 [2000] | (S)-2 [10] |

In Table 2, the values within the brackets [ ] represent the blending amount (parts by weight). Also, the meanings of the abbreviations are described below. The blending amount of the components (B) in Example 3, and Comparative Examples 2 and 3 is a equimolar amount.

(A)-1: the copolymer represented by a general formula (A)-1 shown below (Mw=7,000; Mw/Mn=1.8) (in the formula, 1:m:n=45:35:20 (molar ratio))
(B)-1: the above compound (5)
(B)-2: (4-methylphenyl)diphenylsulfonium nonafluoro-n-butanesulfonate
(B)-3: the above compound (8)
(D)-1: tri-n-pentylamine
(E)-1: salicylic acid
(S)-1: a mixture solvent of PGMEA/EL=6/4 (mass ratio).
(S)-2: γ-butyrolactone

[Chemical Formula 57]

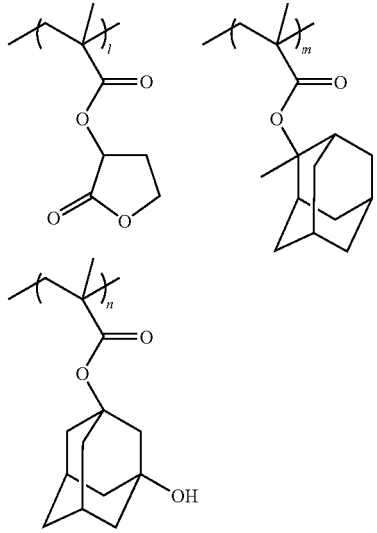

(A)-1

[Formation of Resist Pattern]

Each positive resist composition of Example 3, and Comparative Examples 2 and 3 obtained above was applied onto an 8-inch silicon wafer using a spinner, and the composition was then baked (PAB) at 110° C. for 60 seconds on a hotplate and dried, thereby forming a resist film having a film thickness of 150 nm.

Subsequently, the obtained resist film was selectively exposed by an ArF excimer laser (193 nm), using an ArF exposure apparatus "NSR-S302" (manufactured by Nikon; numerical aperture (NA)=0.60, ⅔ annual illumination) through a mask pattern (halftone).

Thereafter, a post exposure baking (PEB) treatment was conducted at 110° C. for 60 seconds, followed by a development treatment for 30 seconds at 23° C. in a 2.38% by weight aqueous solution of tetramethylammonium hydroxide (TMAH) (product name: NMD-3, manufactured by Tokyo Ohka Kogyo Co., Ltd.), followed by rinsing with pure water for 30 seconds and drying by shaking, thereby forming a line and space (1:1) resist pattern (L/S pattern).

[Sensitivity]

In the resist pattern formation described above, the optimum exposure "Eop" (mJ/cm$^2$; the sensitivity) for formation of the L/S pattern having a line width of 120 nm and a pitch of 240 nm was determined. The results are shown in Table 3.

[Evaluation of Mask Error Factor (MEF)]

With the above-mentioned Eop, a L/S pattern was formed in the same manner as the formation of resist pattern described above, in the case that the mask size was changed to 120 nm and 130 nm while the pitch was fixed at 260 nm, and also in the case that the size of the mask was changed to 110 nm and 120 nm while the pitch was fixed at 240 nm, thereby determining the mask error factor (MEF) in each case described above. Then, the average value of both cases described above was determined, and the value was used as the mask error factor (MEF) for evaluation.

Here, the value of mask error factor in each case described above is a slope of a straight line which connects plotted points, when points are plotted on a graph based on the target line width (nm) of the mask pattern as the abscissa axis, and an actual line width (nm) of the L/S pattern formed on the resist film by using each mask pattern as the longitudinal axis. A MEF value closer to 1 indicates that a resist pattern faithful to the mask pattern was formed (that is, the mask reproducibility was excellent). The results are shown in Table 3.

[Evaluation of Collapse Margin]

In the formation of a L/S pattern targeting a line width of 120 nm and a pitch of 240 nm, the exposure time of the selective exposure was gradually increased to make the exposure dose larger than the Eop, and the occurrence of pattern collapse was observed using a scanning electron microscope (SEM)

The exposure dose (%; Dose) and the line width (nm; CD) at which pattern collapse started to occur was respectively defined as T and L, and the collapse margin (Dose) and (CD) were determined by the following formulae. The results are shown in Table 3.

Collapse margin (Dose) (unit: %)=(T/Eop)×100

Collapse margin (CD) (unit; %)=(L/120 (nm))×100

[Resist Pattern Shape]

A line and space (L/S) pattern of a line width of 110 nm and a pitch of 300 nm was formed in the same manner as the formation of resist pattern described above. The L/S pattern was observed using a scanning electron microscope (SEM), thereby evaluating a cross-sectional shape of the L/S pattern. The results are shown in Table 3.

TABLE 3

|  |  | Example 3 | Comparative Example 2 | Comparative Example 3 |
|---|---|---|---|---|
| Eop (mJ/cm$^2$) |  | 25.7 | 31.2 | 26.5 |
| MEF |  | 2.35 | 2.52 | 2.30 |
| Collapse margin | Dose (%) | 1.48 | 1.41 | 1.39 |
|  | CD (%) | 1.58 | 1.46 | 1.54 |
| Resist pattern shape |  | Rectangular | Trapezoidal | Trapezoidal |

From the result described above, it can be confirmed that the resist composition of Example 3 exhibits excellent mask reproducibility as compared with Comparative Example 2, because it has a smaller MEF value than that of Comparative Example 2. Also, it can be confirmed that the resist composition of Example 3 exhibits excellent mask reproducibility at the same level as that of Comparative Example 3.

Also, it can be confirmed that the resist composition of Example 3 exhibits excellent collapse margin and resist pattern shape, as compared with Comparative Examples 2 and 3.

[Evaluation of Optical Property (Absorbance)]

Each of resist compositions of Example 3', and Comparative Examples 2' and 3', which were respectively the resist compositions of Example 3, and Comparative Examples 2 and 3 with the exception that the components (D) and (E) were not blended therein, was applied on a 1-inch quartz substrate using a spinner, and was then subjected to a bake treatment at 110° C. for 60 seconds, thereby forming a resist film with a film thickness of 150 nm. Then, an absorbance per 1,000 nm of the film thickness in the above resist film (film thickness: 150 nm) was measured at a wavelength within a range of 177 nm to 800 nm using a spectral ellipsometer (manufactured by Woollam Co., Ltd.), and was determined as the absorbance based on the following formula. The absorbance per 1,000 nm of the film thickness at 193 nm of the wavelength is shown in Table 3.

Formula: abs=0.434αL

Here, abs represents an absorbance, α represents an absorbance coefficient, and L represents a film thickness.

TABLE 4

|  | Absorbance per 1000 nm of film thickness at 193 nm of wavelength |
|---|---|
| Example 3' | 1.408 |
| Comparative Example 2' | 1.392 |
| Comparative Example 3' | 2.079 |

As is clear from the results described above, it can be confirmed that the resist composition of Example 3' has high transparency to a light with a wavelength of about 193 nm, as compared with the resist composition of Comparative Example 3'.

Also, the resist composition of Example 3' has transparency to a light with a wavelength of about 193 nm at approximately the same level as the resist composition of Comparative Example 2'.

INDUSTRIAL APPLICABILITY

According to the present invention, there can be provided a novel compound suitable as an acid generator for a resist composition, a compound suitable as a precursor of the novel compound, an acid generator, a resist composition, and a method of forming a resist pattern.

The invention claimed is:

1. A resist composition which comprises a base component (A) which exhibits changed solubility in an alkali developing solution under action of acid, and an acid generator component (B) which generates an acid upon exposure, wherein the acid generator component (B) comprises an acid generator (B1) represented by a general formula (b1-1) shown below:

[Chemical Formula 3]

$$X-Q^1-Y^1-SO_3^- A^+ \quad (b1\text{-}1)$$

(wherein, $Q^1$ represents a combination of an ether linkage with a group of $-R^{92}-O-C(=O)-$; $R^{92}$ represents an alkylene group; $Y^1$ represents an alkylene group which may contain a substituent group, or a fluorinated alkylene group which may contain a substituent group; X represents an aromatic cyclic group of 5 to 30 carbon atoms which contains a fluorine atom and may contain a substituent group; and $A^+$ represents an organic cation).

2. The resist composition according to claim 1, wherein the base component (A) is a base component which exhibits increased solubility in an alkali developing solution under action of acid.

3. The resist composition according to claim 2, wherein the base component (A) comprises a resin component (A1) which exhibits increased solubility in an alkali developing solution under action of acid, and the resin component (A1) comprises a structural unit (a1) derived from an acrylate ester which has an acid dissociable, dissolution inhibiting group.

4. The resist composition according to claim 3, wherein the resin component (A1) further comprises a structural unit (a2) derived from an acrylate ester which has a lactone-containing cyclic group.

5. The resist composition according to claim 3, wherein the resin component (A1) further comprises a structural unit (a3) derived from an acrylate ester which has a polar group-containing aliphatic hydrocarbon group.

6. The resist composition according to claim 4, wherein the resin component (A1) further comprises a structural unit (a3) derived from an acrylate ester which has a polar group-containing aliphatic hydrocarbon group.

7. The resist composition according to claim 1, which comprises a nitrogen-containing organic compound (D).

8. A method of forming a resist pattern, comprising: forming a resist film on a substrate using the positive resist composition described in any one of claims 1 to 7; exposing the resist film; and developing the resist film with an alkali to form a resist pattern.

9. A compound represented by a general formula (I) shown below:

[Chemical Formula 1]

$$X-Q^1-Y^1-SO_3^{31}M^+ \qquad (I)$$

(wherein, $Q^1$ represents a combination of an ether linkage with a group of $-R^{92}-O-C(=O)-$; $R^{92}$ represents an alkylene group; $Y^1$ represents an alkylene group which may contain a substituent group, or a fluorinated alkylene group which may contain a substituent group; X represents an aromatic cyclic group of 5 to 30 carbon atoms which contains a fluorine atom and may contain a substituent group; and $M^+$ represents an alkali metal ion).

10. A compound represented by a general formula (b1-1) shown below:

[Chemical Formula 2]

$$X-Q^1-Y^1-SO_3^{31}A^+ \qquad (b1\text{-}1)$$

(wherein, $Q^1$ represents a combination of an ether linkage with a group of $-R^{92}-O-C(=O)-$; $R^{92}$ represents an alkylene group; $Y^1$ represents an alkylene group which may contain a substituent group, or a fluorinated alkylene group which may contain a substituent group; X represents an aromatic cyclic group of 5 to 30 carbon atoms which contains a fluorine atom and may contain a substituent group; and $A^+$ represents an organic cation).

11. The compound according to claim 10, wherein the aromatic cyclic group of 5 to 30 carbon atoms which contain a fluorine atom for X is a group in which all of hydrogen atoms in the aromatic cyclic group are substituted with fluorine atoms.

12. The resist composition according to claim 1, wherein the aromatic cyclic group of 5 to 30 carbon atoms which contain a fluorine atom for X is a group in which all of hydrogen atoms in the aromatic cyclic group are substituted with fluorine atoms.

13. The compound according to claim 9, wherein the aromatic cyclic group of 5 to 30 carbon atoms which contain a fluorine atom for X is a group in which all of hydrogen atoms in the aromatic cyclic group are substituted with fluorine atoms.

14. An acid generator composed of the compound described in claim 10 or 11.

* * * * *

UNITED STATES PATENT AND TRADEMARK OFFICE
CERTIFICATE OF CORRECTION

PATENT NO. : 7,955,777 B2
APPLICATION NO. : 12/327549
DATED : June 7, 2011
INVENTOR(S) : Takehiro Seshimo et al.

It is certified that error appears in the above-identified patent and that said Letters Patent is hereby corrected as shown below:

At Title Page 1, Item 57 Abstract, Line 17, Change "cation.)." to --cation.)--.

At Column 5, Line 28, Change "Y1" to --$Y^1$--.

At Column 8, Line 44, Change "alkal," to --alkali,--.

At Column 22, Line 62, Change "atoms).)" to --atoms).--.

At Column 76, Line 20, Change "2-norbonyl" to --2-norbornyl--.

At Column 76, Line 20, Change "3-norbonyl" to --3-norbornyl--.

At Column 82, Line 2, Change "methansulfonate," to --methanesulfonate,--.

At Column 92, Line 58, After ")" insert --.--.

At Column 93, Line 47, Change "dropwide" to --dropwise--.

At Column 94, Line 15, Change "4H,Ha," to --4H, Ha,--.

At Column 95, Line 65-66, Change "dropwide" to --dropwise--.

At Column 99, Line 21, After ")" insert --.--.

At Column 100, Line 10-11, Change "absobance" to --absorbance--.

At Column 100, Line 57, In Claim 1, change "$A^+$represents" to --$A^+$ represents--.

Signed and Sealed this
Twenty-second Day of November, 2011

David J. Kappos
*Director of the United States Patent and Trademark Office*

CERTIFICATE OF CORRECTION (continued)
U.S. Pat. No. 7,955,777 B2

At Column 101, Line 23, In Claim 9, change " 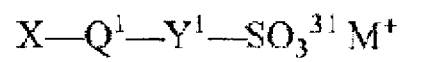 "

to -- 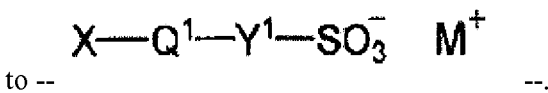 --.

At Column 102, Line 4, In Claim 10, change " 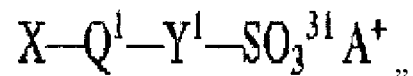 "

to -- 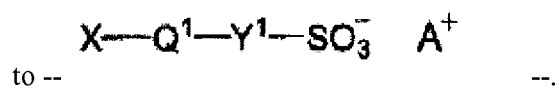 --.

At Column 102, Line 13, In Claim 10, change "A$^+$represents" to --A$^+$ represents--.